(12) United States Patent
Tyers et al.

(10) Patent No.: US 6,426,205 B1
(45) Date of Patent: Jul. 30, 2002

(54) METHODS AND COMPOSITIONS FOR MODULATING UBIQUITIN DEPENDENT PROTEOLYSIS

(75) Inventors: Mike Tyers; Andrew Willems, both of Toronto (CA)

(73) Assignee: Mount Sinai Hospital Corporation, Toronto (CA)

( * ) Notice: Subject to any disclaimer, the term of this patent is extended or adjusted under 35 U.S.C. 154(b) by 0 days.

(21) Appl. No.: 09/177,165

(22) Filed: Oct. 22, 1998

Related U.S. Application Data

(60) Provisional application No. 60/063,254, filed on Oct. 24, 1997, and provisional application No. 60/092,443, filed on Jul. 10, 1998.

(51) Int. Cl.$^7$ .............................. C12N 9/12; C07K 9/00; C07K 14/395
(52) U.S. Cl. ...................... 435/194; 530/325; 530/326; 530/327
(58) Field of Search .................. 514/13, 141; 424/94.5; 435/194; 530/325–327

(56) References Cited

PUBLICATIONS

Patton et al. (Mar. 1998) Genes & Development, vol. 12, pp. 692–705.*
Bai, C. et al. 1996. Cell 86:263–274.
Barral, Y. et al. 1995. Genes & Dev. 9:399–409.
Clurman, B.E. et al. 1996. Genes & Dev. 10:1979–1990.
Connelly, C. and P. Hieter. 1996. Cell 86: 275–285.
Willems, A.R. et al. 1996. Cell 86: 453–463.
Deschais, R.J. et al. 1995. EMBO J. 14:303–312.
Diehl, J.A. et al. Genes & Dev. 11: 957–972.
Durfee, T. et al. 1993. Genes & Dev. 7:555–569.
Erickson, J.R. and M. Johnson. 1994. Genetics 136: 1271–1278.
Flick, J.S. and M. Johnson. 1991. Mol. Cell. Biol. 11: 5101–5112.
Goebl, M.G. et al. 1998. Science 241: 1331–1335.
Won, K.A. and S.I. Reed. 1996. EMBO J. 15: 4182–4193.
Hochstrasser, M. 1996. Annu. Rev. Genet. 30: 405–439.
James, P. et al. 1996. Genetics 144: 1425–1436.
Yochem, J. and B. Byers. 1987. J. Mol. Biol. 195: 233–245.
King, R.W. et al. 1996. Science 274: 1652–1659.
Kipreos, E.T. et al. 1996. Cell 85: 829–839.
Kominami, K. and T. Toda 1997. Genes & Dev. 11: 1548–1560.
Kornitzer, D. et al. 1994. EMBO J. 13: 6012–6030.
Kumar, A. and J.V. Paietta. 1995. Proc. Natl. Acad. Sci. 92: 3343–3347.
Kuras, L et al. 1996. EMBO J. 15: 2519–2529.
Mathias, N. et al. 1996. Mol. Cell. Biol. 16: 6634–6643.
McKinney, J.D. et al. 1993. Genes & Dev. 7: 833–843.
Nasmyth, K. 1996. Trends. Genet. 12: 405–412.
Natorff, R. et al. 1993. Mol. Gen. Genet. 238: 185–192.
Nugroho, T. et al. 1994. Mol. Cell. Biol. 14: 3320–3328.
Zhang, H.R. et al. 1995. Cell 82: 915–925.
Pause, A. et al. 1997. Proc. Natl. Acad. Sci. 94: 2156–2161.
Piatti, S. et al. 1996. Genes & Dev. 10: 1516–1531.
Scheffner, M. et al. 1995. Nature 373: 81–83.
Schneider, B.L. et al. 1996. Science 272: 560–562.
Schwob, E. et al. 1994. Cell 79: 233–244.
Verma, R. et al. 1997. Mol. Biol. Cell. 8: 1427–1437.
Skowrya, D. et al. 1997. Cell 91:209–219, 1997.
Stemmann, O. and J. Lechner. 1996. EMBO J. 15: 3611–3620.
Thomas D. et al. 1995. Mol. Cell. Biol. 15: 6525–6534.
Thompson, J.D. et al. 1994. Nucleic Acid Research 22: 4673–4680.
Tyers, M. 1996. Proc. Natl. Acad. Sci. 93: 7772–7776.
Tyers, M. et al. 1992. EMBO J. 11: 1773–1784.
Vallier, L.G. et al. 1994. Genetics 136: 1279–1285.

* cited by examiner

*Primary Examiner*—Elizabeth Slobodyansky
(74) *Attorney, Agent, or Firm*—Merhant & Gould P.C.

(57) ABSTRACT

The invention relates to methods and compositions for modulating ubiquitin dependent proteolysis.

2 Claims, 29 Drawing Sheets

FIG. 7A

LOCUS       136642      295 aa                    01-FEB-1997
DEFINITION  UBIQUITIN-CONJUGATING ENZYME E2-34 KD (UBIQUITIN-
PROTEIN LIGASE)
            (UBIQUITIN CARRIER PROTEIN) (CELL DIVISION CONTROL PROTEIN
34).
ACCESSION   136642
PID         g136642
DBSOURCE    SWISS-PROT: locus UBC3_YEAST, accession P14682
            class: standard.
            created: Apr 1, 1990.
            sequence updated: Apr 1, 1990.
            annotation updated: Feb 1, 1997.
            xrefs: gi: 173123, gi: 173124, gi: 706817, gi: 706820, gi: 1431496,
            gi: 798897, gi: 798905, gi: 101249
            xrefs (non-sequence databases): HSSP P25865, SGD L0000271, PROSITE
            PS00183
KEYWORDS    UBIQUITIN CONJUGATION; LIGASE; DNA REPLICATION;
NUCLEAR PROTEIN;
            CELL CYCLE; CELL DIVISION; MULTIGENE FAMILY.
SOURCE      baker's yeast.
  ORGANISM  Saccharomyces cerevisiae
            Eukaryotae; Fungi; Ascomycota; Hemiascomycetes; Saccharomycetales;
            Saccharomycetaceae; Saccharomyces.
REFERENCE   1  (residues 1 to 295)
  AUTHORS   Goebl,M.G., Yochem,J., Jentsch,S., McGrath,J.P., Varshavsky,A. and
            Byers,B.
  TITLE     The yeast cell cycle gene CDC34 encodes a ubiquitin-conjugating
            enzyme
  JOURNAL   Science 241 (4871), 1331-1335 (1988)
  MEDLINE   88321694
  REMARK    SEQUENCE FROM N.A.
REFERENCE   2  (residues 1 to 295)
  AUTHORS   Brandt,P., Ramlow,S., Otto,B. and Bloecker,H.
  TITLE     Nucleotide sequence analysis of a 32,500 bp region of the right arm
            of Saccharomyces cerevisiae chromosome IV
  JOURNAL   Yeast 12 (1), 85-90 (1996)
  MEDLINE   96381250
  REMARK    SEQUENCE FROM N.A.
REFERENCE   3  (residues 1 to 295)
  AUTHORS   HUNT,S., BOWMAN,S., HARRIS,D., BARRELL,B. and
RAJANDREAM,M.A.

FIG. 7B

TITLE     Direct Submission
JOURNAL   Submitted (??-MAY-1995) TO EMBL/GENBANK/DDBJ DATA BANKS
  REMARK   SEQUENCE FROM N.A.
        STRAIN=S288C / AB972
COMMENT   [FUNCTION] CATALYSES THE COVALENT ATTACHMENT OF UBIQUITIN TO OTHER
        PROTEINS. CAPABLE, IN VITRO, TO UBIQUITINATE HISTONE H2A.
        [FUNCTION] MEDIATES THE INITIATION OF DNA REPLICATION (TRANSITION
        OF G1 TO S PHASE IN CELL CYCLE).
        [CATALYTIC ACTIVITY] ATP + UBIQUITIN + PROTEIN LYSINE = AMP + PYROPHOSPHATE + PROTEIN N-UBIQUITYLLYSINE.
        [PATHWAY] SECOND STEP IN UBIQUITIN CONJUGATION.
        A CYSTEINE RESIDUE IS REQUIRED FOR UBIQUITIN-THIOLESTER FORMATION.
        [DOMAIN] THE ACIDIC C-TERMINAL EXTENSION IS ESSENTIAL FOR THE CELL
        CYCLE FUNCTION.
        [SUBCELLULAR LOCATION] NUCLEAR.
        [SIMILARITY] TO THE OTHER UBIQUITIN-CONJUGATING ENZYMES.
FEATURES          Location/Qualifiers
    source       1..295
            /organism="Saccharomyces cerevisiae"
            1..295
    Protein      1..295
            /product="UBIQUITIN-CONJUGATING ENZYME E2-34 KD"
            /EC_number="6.3.2.19"
    Site         95
            /note="UBIQUITIN."
            /site_type="binding"
    Region       191..289
            /note="ASP/GLU-RICH (BASIC)."
            /region_name="Domain"
ORIGIN
    1 mssrkstass lllrqyrelt dpkkaipsfh ieleddsnif twnigvmvln edsiyhggff
   61 kaqmrfpedf pfsppqfrft paiyhpnvyr dgrlcisilh qsgdpmtdep daetwspvqt
  121 vesvlisivs lledpninsp anvdaavdyr knpeqykqrv kmeverskqd ipkgfimpts
  181 esayisqskl depesnkdma dnfwydsdld ddengsvilq dddyddgnnh ipfedddvyn
  241 yndndddder iefeddddddd ddsidndsvm drkqphkaed esedvedver vskki
//

FIG. 7C

```
LOCUS       388309      298 aa                    06-DEC-1993
DEFINITION  ubiquitin conjugating enzyme.
ACCESSION   388309
PID         g388309
DBSOURCE    GENBANK: locus HUMCDC34H, accession L22005
KEYWORDS    .
SOURCE      human.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (residues 1 to 298)
  AUTHORS   Plon,S.E., Leppig,K.A., Do,H.-N. and Groudine,M.
  TITLE     Cloning of the human homolog of the CDC34 cell cycle gene by
            complementation in yeast
  JOURNAL   Proc. Natl. Acad. Sci. U.S.A. 90, 10484-10488 (1993)
REFERENCE   2  (residues 1 to 298)
  AUTHORS   Plon,S.E.
  TITLE     Direct Submission
  JOURNAL   Submitted (31-AUG-1993) Sharon E. Plon, Texas Children's Hospital,
            MC3-3320, 6621 Fannin Street, Houston, TX 77030 USA
COMMENT     Method: conceptual translation.
FEATURES             Location/Qualifiers
     source          1..298
                     /organism="Homo sapiens"
                     /cell_line="U118"
                     /tissue_lib="AA2M, ADANS vector library of J. Collicelli"
                     /map="19p13.3"
     Protein         1..298
                     /product="ubiquitin conjugating enzyme"
     CDS             1..298
                     /function="complements a CDC34 mutation of S. cerevisiae"
                     /evidence=experimental
                     /coded_by="L22005:<1..897"
ORIGIN
     1 iaaapeller sgspgggga eeeagggpgg sppdgarpgp srelavvarp raaptpgpsa
    61 aamarplvps sqkalllelk glqeepvegf rvtlvdegdl ynwevaifgp pntyyeggyf
   121 karlkfpidy pysppafrfl tkmwhpniye tgdvcisilh ppvddpqsge lpserwnptq
   181 nvrtillsvi sllnepntfs panvdasvmy rkwkeskgkd reytdiirkq vlgtkvdaer
   241 dgvkvpttla eycvktkapa pdegsdlfyd dyyedgevee eadscfgdde ddsgtees
//
```

FIG. 8A

```
LOCUS       1736921    815 aa              17-DEC-1996
DEFINITION  Cdc53p.
ACCESSION   1736921
PID         g1736921
DBSOURCE    GENBANK: locus SCU43564, accession U43564
KEYWORDS    .
SOURCE      baker's yeast.
  ORGANISM  Saccharomyces cerevisiae
            Eukaryotae; mitochondrial eukaryotes; Fungi; Ascomycota;
            Hemiascomycetes; Saccharomycetales; Saccharomycetaceae;
            Saccharomyces.
REFERENCE   1  (residues 1 to 815)
  AUTHORS   Mathias,N., Johnson,S.L., Winey,M., Adams,A.E., Goetsch,L.,
            Pringle,J.R., Byers,B. and Goebl,M.G.
  TITLE     Cdc53p acts in concert with Cdc4p and Cdc34p to control the
            G1-to-S-phase transition and identifies a conserved family of
            proteins
  JOURNAL   Mol. Cell. Biol. 16 (12), 6634-6643 (1996)
  MEDLINE   97098640
REFERENCE   2  (residues 1 to 815)
  AUTHORS   Goebl,M.G.
  TITLE     Direct Submission
  JOURNAL   Submitted (18-DEC-1995) Mark G. Goebl, Biochemistry and Molecular
            Biology, Indiana University School of Medicine, 635 Barnhill Drive,
            Indianapolis, IN 46202, USA
COMMENT     Method: conceptual translation.
FEATURES             Location/Qualifiers
     source          1..815
                     /organism="Saccharomyces cerevisiae"
     Protein         1..815
                     /product="Cdc53p"
     CDS             1..815
                     /gene="CDC53"
                     /coded_by="U43564:540..2987"
ORIGIN
     1 msetlprsdd leatwnfiep ginqilgnek nqastskrvy kilsptmyme vytaiynycv
    61 nksrssghfs tdsrtgqsti lvgseiyekl knylknyiln fkqsnsetfl qfyvkrwkrf
   121 tigaiflnha fdymnrywvq kersdgkrhi fdvntlclmt wkevmfdpsk dvlinelldq
   181 vtlgregqii qrsnistaik slvalgidpq dlkklnlnvy iqvfekpfllk ktqeyytqyt
   241 ndylekhsvt eyifeaheii kreekamtiy wddhtkkpls malnkvlitd hieklenefv
   301 vlldardiek itslyalirr dftliprmas vfenyvkktg eneissllam hkhnimknen
   361 anpkklalmt ahslspkdyi kkllevhdif skifnesfpd diplakaldn acgafinine
```

FIG. 8B 421 falpagspks atsktsemla kysdillkka tkpevasdms dediitifky ltdkdafeth
481 yrrlfakrli hgtstsaede eniiqrlqaa nsmeytgkit kmfqdirlsk ileddfaval
541 knepdyskak ypdlqpfvla enmwpfsyqe vefklpkelv psheklkesy sqkhngrilk
601 wlwplcrgel kadigkpgrm pfnftvtlfq mailllynda dvltleniqe gtsltiqhia
661 aamvpfikfk liqqvppgld alvkpetqfk lsrpykalkt ninfasgvkn dilqslsggg
721 hdnhgnklgn krltederie kelnterqif leacivrimk akrnlphttl vneciaqshq
781 rfnakvsmvk raidsliqkg ylqrgddges yayla
//

LOCUS     1923243    745 aa             02-APR-1997
DEFINITION  CUL-2.
ACCESSION  1923243
PID        g1923243
DBSOURCE   GENBANK: locus HSU83410, accession U83410
KEYWORDS
SOURCE     human.
  ORGANISM  Homo sapiens
            Eukaryotae; mitochondrial eukaryotes; Metazoa; Chordata;
            Vertebrata; Mammalia; Eutheria; Primates; Catarrhini; Hominidae;
            Homo.
REFERENCE  1  (residues 1 to 745)
  AUTHORS  Pause,A., Lee,S., Worrel,R., Chen,D.Y.T., Burgess,W.H.,
           Linehan,W.M. and Klausner,R.D.
  TITLE    The VHL tumor suppressor gene product forms a stable complex with
           human CUL-2 a member of the Cdc53 family of proteins
  JOURNAL  Proc. Natl. Acad. Sci. U.S.A. 94, 2156-2161 (1997)
REFERENCE  2  (residues 1 to 745)
  AUTHORS  Pause,A.
  TITLE    Direct Submission
  JOURNAL  Submitted (30-DEC-1996) CBMB, NICHD, NIH, 18 Library Drive,
           Bethesda, MD 20892, USA
COMMENT    Method: conceptual translation supplied by author.
FEATURES           Location/Qualifiers
     source        1..745
                   /organism="Homo sapiens"
                   /tissue_type="kidney"
     Protein       1..745
                   /product="CUL-2"
     CDS           1..745
                   /gene="cul-2"
                   /note="VHL tumor suppressor protein binding protein"
                   /coded_by="U83410:147..2384"
ORIGIN
    1 mslkprvvdf detwnklltt ikavvmleyv eratwndrfs diyalcvayp eplgerlyte

FIG. 8C 421 lvfckhitsv pisavlrgck flqsvditgi rdvsddvfdt latycprvqg fyvpqarnvt
481 fdslrnfivh spmlkrikit annnmndelv ellankcpll vevditlspn vtdssllkll
541 trlvqlrefr ithntnitdn lfqelskvvd dmpslrlidl sgcenitdkt iesivnlapk
601 lrnvflgkcs ritdaslfql sklgknlqtv hfghcfnitd ngvralfhsc triqyvdfac
661 ctnltnrtly eladlpkllkr iglvkctqmt degllnmvsl rgrndtlerv hlsycsnlti
721 ypiyellmsc prlshlslta vpsflrpdit mycrpapsdf senqrqifcv fsgkgvhklr
781 hylvnltspa fgphvdvndv ltkyirsknl ifngetleda lrriitdlnq dsaaiiaatg
841 lnqinglnnd flfqninfer idevfswyln tfdgirmsse evnslllqvn ktfcedpfsd
901 vdddqdyvva pgvnreinse mchivrkfhe lndhiddfev nvaslvrvqf qftgfllhem
961 tqtymqmiel nrqiclvqkt vqesgnidyq kglliwrllf idkfimvvqk yklstvvlrl
1021 ylkdnitllt rqrelliahq rsawnnnndn danrnanniv nivsdagand tsnnetrngn
1081 ddnetenpnf wrqfgnrmqi spdqmrrnlqm glrnqnmvrn nnnntidesm pdtaidsqmd
1141 easgtpdedm l
//

FIG. 9

LOCUS       2133137    194 aa              23-AUG-1996
DEFINITION  SKP1 protein - yeast (Saccharomyces cerevisiae).
ACCESSION   2133137
PID         g2133137
DBSOURCE    PIR: locus S59793
            summary: #length 194 #molecular-weight 22330 #checksum 5937.
            genetic: #gene SKP1 #map_position 4R.
            PIR dates: 13-Jan-1996 #sequence_revision 01-Mar-1996 #text_change
            23-Aug-1996.
KEYWORDS    .
SOURCE      baker's yeast.
  ORGANISM  Saccharomyces cerevisiae
            Eukaryotae; mitochondrial eukaryotes; Fungi; Ascomycota;
            Hemiascomycetes; Saccharomycetales; Saccharomycetaceae;
            Saccharomyces.
REFERENCE   1 (residues 1 to 194)
  AUTHORS   Du, Z.
  TITLE     Direct Submission
  JOURNAL   Submitted (??-JUL-1995) to the EMBL Data Library
REFERENCE   2 (residues 1 to 194)
  AUTHORS   Connely, C.J. and Hieter, P.
  TITLE     Direct Submission
  JOURNAL   Submitted (??-DEC-1995) to the EMBL Data Library
FEATURES            Location/Qualifiers
     source          1..194
                     /organism="Saccharomyces cerevisiae"
     Protein         1..194
                     /note="protein D9798.14; protein YDR328c"
                     /product="SKP1 protein"
ORIGIN
        1 mvtsnvvlvs gegerftvdk kiaerslllk nylndmhdsn lqnnsdsesd sdsetnhksk
       61 dnnngdddde dddeivmpvp nvrssvlqkv iewaehhrds nfpdedddds rksapvdswd
      121 reflkvdqem lyeiilaany lnikplldag ckvvaemirg rspeeirrtf nivndftpee
      181 eaairrenew aedr
//

FIG. 10A

```
LOCUS       1168815    779 aa              01-NOV-1995
DEFINITION  CELL DIVISION CONTROL PROTEIN 4.
ACCESSION   1168815
PID         g1168815
DBSOURCE    SWISS-PROT: locus CC4_YEAST, accession P07834
            class: standard.
            created: Aug 1, 1988.
            sequence updated: Nov 1, 1995.
            annotation updated: Nov 1, 1995.
            xrefs: gi: 3502, gi: 3503, gi: 836685, gi: 836745, gi: 836814, gi:
            836815, gi: 559925, gi: 559926
            xrefs (non-sequence databases): LISTA SC00158, SGD L0000244,
            PROSITE PS00678
KEYWORDS    CELL DIVISION; MITOSIS; SPORULATION; REPEAT.
SOURCE      baker's yeast.
  ORGANISM  Saccharomyces cerevisiae
            Eukaryotae; mitochondrial eukaryotes; Fungi; Ascomycota;
            Hemiascomycetes; Saccharomycetales; Saccharomycetaceae;
            Saccharomyces.
REFERENCE   1  (residues 1 to 779)
  AUTHORS   Yochem,J. and Byers,B.
  TITLE     Structural comparison of the yeast cell division cycle gene CDC4
            and a related pseudogene
  JOURNAL   J. Mol. Biol. 195 (2), 233-245 (1987)
  MEDLINE   88011240
  REMARK    SEQUENCE FROM N.A.
REFERENCE   2  (residues 1 to 779)
  AUTHORS   MURAKAMI,Y., NAITOU,M., HAGIWARA,H., SHIBATA,T.,
OZAWA,M.,
            SASANUMA,S.-I., SASANUMA,M., TSUCHIYA,Y., SOEDA,E.,
YOKOYAMA,K.,
            YAMAZAKI,M., TASHIRO,H. and EKI,T.
  JOURNAL   NAT. GENET. 10, 261-268 (1995)
  REMARK    SEQUENCE FROM N.A.
            STRAIN=S288C / AB972
REFERENCE   3  (residues 1 to 779)
  AUTHORS   BARRELL,B.G., CHURCHER,C. and RAJANDREAM,M.A.
  TITLE     Direct Submission
  JOURNAL   Submitted (??-SEP-1994) TO EMBL/GENBANK/DDBJ DATA BANKS
  REMARK    SEQUENCE OF 1-579 FROM N.A.
            STRAIN=S288C / AB972
```

FIG. 10B

COMMENT    [FUNCTION] THIS PROTEIN IS ESSENTIAL FOR INITIATION OF DNA
         REPLICATION AND SEPARATION OF THE SPINDLE POLE BODIES TO FORM THE
         POLES OF THE MITOTIC SPINDLE. IT ALSO PLAYS A ROLE IN BUD
         DEVELOPMENT, FUSION OF ZYGOTIC NUCLEI AFTER CONJUGATION AND VARIOUS
         ASPECTS OF SPORULATION. REQUIRED FOR HTA1-HTB1 LOCUS TRANSCRIPTION
         ACTIVATION.
         [SIMILARITY] BELONGS TO THE BETA TRANSDUCIN FAMILY; CONTAINS 8
         TRP-ASP DOMAINS.
FEATURES         Location/Qualifiers
   source       1..779
           /organism="Saccharomyces cerevisiae"
           1..779
   Protein      1..779
           /product="CELL DIVISION CONTROL PROTEIN 4"
   Region       460
           /note="K -> E (IN REF. 1)."
           /region_name="Conflict"
ORIGIN
    1 mgsfplaefp lrdipvpysy rvsggiassg svtalvtaag thrnsstakt vetedgeedi
   61 deyqrkraag sgestpersd fkrvkhdnhk tlhpvnlqnt gaasvdndgl hnltdisnda
  121 ekllmsvddg saapstlsvn mgvashnvaa pttvnaatit gsdvsnnvns atinnpmeeg
  181 alplsptass pgtttplakt tktinnnnni adlieskdsi ispeylsdei fsainnnlph
  241 ayfknllfrl vanmdrsels dlgtlikdnl krdlitslpf eislkifnyl qfediinslg
  301 vsqnwnkiir kstslwkkll isenfvspkg fnslnlklsq kypklsqqdr lrlsflenif
  361 ilknwynpkf vpqrttlrgh mtsvitclqf ednyvitgad dkmirvydsi nkkfllqlsg
  421 hdggvwalky ahggilvsgs tdrtvrvwdi kkgccthvfk ghnstvrcld iveyknikyi
  481 vtgsrdntlh vwklpkessv pdhgeehdyp lvfhtpeenp yfvgvlrghm asvrtvsghg
  541 nivvsgsydn tlivwdvaqm kclyilsght driystiydh erkrcisasm dttiriwdle
  601 niwnngecsy atnsaspcak ilgamytlqg htalvgllrl sdkflvsaaa dgsirgwdan
  661 dysrkfsyhh tnlsaittfy vsdnilvsgs enqfniynlr sgklvhanil kdadqiwsvn
  721 fkgktlvaav ekdgqsflei ldfskaskin yvsnpvnsss sslesistsl gltrttiip
//

FIG. 10C

```
LOCUS       1078109    640 aa                01-MAR-1996
DEFINITION  MET30 protein - yeast (Saccharomyces cerevisiae).
ACCESSION   1078109
PID         g1078109
DBSOURCE    PIR: locus S49932
            summary: #length 640 #molecular-weight 72835 #checksum 2765.
            genetic: #gene MET30 #map_position 9L.
            PIR dates: 28-May-1993 #sequence_revision 24-Feb-1995 #text_change
            01-Mar-1996.
KEYWORDS    .
SOURCE      baker's yeast.
  ORGANISM  Saccharomyces cerevisiae
            Eukaryotae; mitochondrial eukaryotes; Fungi; Ascomycota;
            Hemiascomycetes; Saccharomycetales; Saccharomycetaceae;
            Saccharomyces.
REFERENCE   1 (residues 1 to 640)
  AUTHORS   Thomas, D., Cherest, H., Barbey, R. and Surdin-Kerjan, Y.
  TITLE     Direct Submission
  JOURNAL   Submitted (??-DEC-1993) to the EMBL Data Library
REFERENCE   2 (residues 1 to 640)
  AUTHORS   Odell, C. and Bowman, S.
  TITLE     Direct Submission
  JOURNAL   Submitted (??-DEC-1994) to the EMBL Data Library
FEATURES            Location/Qualifiers
     source         1..640
                    /organism="Saccharomyces cerevisiae"
     Protein        1..640
                    /note="protein YI9905.02; protein YIL046w"
                    /product="MET30 protein"
ORIGIN
        1 mrrerqrmms fedkdkddld nsnsnnssem tdtammpplk rllitgssdd laqgssgkkk
       61 mtmatrspss spdlatndsg trvqplpeyn ftkfcyrhnp diqfspthta cykqdlkrtq
      121 einaniaklp lqeqsdihhi iskysnsndk irklildgil stscfpqlsy isslvthmik
      181 idfisilpqe lslkilsyld cqslcnatrv crkwqkladd drvwyhmceq hidrkcpncg
      241 wglpllhmkr ariqqnstgs ssnadiqtqt trpwkviyre rfkvesnwrk ghcriqefkg
      301 hmdgvltlqf nyrllftgsy dstigiwdlf tgklirrlsg hsdgvktlyf ddrklitgsl
      361 dktirvwnyi tgecistyrg hsdsvlsvds yqkvivsgsa dktvkvwhve srtcytlrgh
      421 tewvncvklh pksfscfscs ddttirmwdi rtnsclkvfr ghvgqvqkii pltikdvenl
      481 atdntsdgss pqddptmtdg adesdtpsne qetvldenip ypthllscgl dntiklwdvk
      541 tgkcirtqfg hvegvwdiaa dnfriisgsh dgsikvwdlq sgkcmhtfng rrlqretqht
      601 qtqslgdkva piacvcigds ecfsgdefgc vkmykfdlnd
//
```

FIG. 10D

LOCUS    83041    1151 aa           13-SEP-1995
DEFINITION  GRR1 protein - yeast (Saccharomyces cerevisiae).
ACCESSION   83041
PID      g83041
DBSOURCE   PIR: locus A41529
         summary: #length 1151 #molecular-weight 132733 #checksum 1173.
         genetic: #gene LISTA:GRR1 #map_position 10R.
         PIR dates: 30-Jun-1992 #sequence_revision 30-Jun-1992 #text_change
         13-Sep-1995.
KEYWORDS   tandem repeat.
SOURCE    baker's yeast.
 ORGANISM  Saccharomyces cerevisiae
         Eukaryotae; mitochondrial eukaryotes; Fungi; Ascomycota;
         Hemiascomycetes; Saccharomycetales; Saccharomycetaceae;
         Saccharomyces.
REFERENCE  1  (residues 1 to 1151)
 AUTHORS   Flick,J.S. and Johnston,M.
 TITLE    GRR1 of Saccharomyces cerevisiae is required for glucose repression
         and encodes a protein with leucine-rich repeats
 JOURNAL  Mol. Cell. Biol. 11 (10), 5101-5112 (1991)
 MEDLINE  92017785
REFERENCE  2  (residues 1 to 1151)
 AUTHORS   Ramezani Rad, M., Kirchrath, L. and Hollenberg, C.P.
 TITLE    Direct Submission
 JOURNAL  Submitted (??-SEP-1995) to the Protein Sequence Database
REFERENCE  3  (residues 1 to 1151)
 AUTHORS   Manus, V., Huang, M.E. and Galibert, F.
 TITLE    Direct Submission
 JOURNAL  Submitted (??-SEP-1995) to the Protein Sequence Database
FEATURES         Location/Qualifiers
    source     1..1151
              /organism="Saccharomyces cerevisiae"
    Protein    1..1151
              /note="protein J1885; protein YJR090c"
              /product="GRR1 protein"
    Region     409..725
              /note="26-residue repeats"
              /region_name="region"
ORIGIN
    1 mdqdnnnhnd snrlhppdih pnlgpqlwln ssgdfddnnn nnnnnnnnns trpqmpsrtr
   61 etatsernas evrdatlnni frfdsiqret llptnngqpl nqnfsltfqp qqqtnalngi
  121 dintvntnlm ngvnvqidql nrllpnlpee erkqihefkl ivgkkiqefl vviekrrkki
  181 lneieldnlk lkelridnsp qaisylhklq rmrlralete nmeirnlrlk iltiieeykk
  241 slyaychskl rgqqvenptd nfiiwinsid ttessdlkeg lqdlsrysrq finnvlsnps
  301 nqnictsvtr rspvfalnml pseilhlild klnqkydivk fltvsklwae iivkilyyrp
  361 hinkksqldl flrtmkkltse etvfnyrlmi krlnfsfvgd ymhdtelnyf vgcknlerlt

FIG. 10E

```
 61 tkiflenhvr hlhkrvlese eqvlvmyhry weeyskgady mdclyrylst qfikknklte
121 adlqygyggv dmneplmeig elaldmwrkl mveplqaili rmllreiknd rggedpnqkv
181 ihgvinsfvh veqykkkfpl kfyqeifesp fltetgeyyk qeasnllqes ncsqymekvl
241 grlkdeeirc rkylhpssyt kvihecqqrm vadhlqflha echniirqek kndmanmyvl
301 lravstglph miqelqnhih deglratsnl tqenmptlfv esvlevhgkf vqlintvlng
361 dqhfmsaldk altsvvnyre pksvckapel lakycdnllk ksakgmtene vedrltsfit
421 vfkyiddkdv fqkfyarmla krlihglsms mdseeamink lkqacgyeft sklhrmytdm
481 svsadlnnkf nnfiknqdtv idlgisfqiy vlqagawplt qapsstfaip qeleksvqmf
541 elfysqhfsg rkltwlhylc tgevkmnylg kpyvamvtty qmavllafnn setvsykelq
601 dstqmnekel tktikslldv kminhdseke didaessfsl nmnfsskrtk fkittsmqkd
661 tpqemeqtrs avdedrkmyl qaaivrimka rkvlrhnali qevisqsrar fnpsismikk
721 cievlidkqy iersqasade ysyva
```

| | | | | |
|---|---|---|---|---|
| Sc Cdc53 | 42 | ILSPTM | YM | EVYTAIYNYCVNKS | 63 |
| Ce Cul1 | 32 | NMAPKD | YM | TLYTSVYDYCTSIT | 53 |
| Ce Cul6 | 22 | HMSKKY | YM | MLYDAVYNICTTTT | 43 |
| Dm Lin-19 | 36 | SLTRSQ | YM | RFYTHVYDYCTSVS | 57 |
| Hs Cul1 | 36 | SMAKSR | YM | ELYTHVYNYCTSVH | 57 |
| At cullin-like 1 | 33 | AFDSEQ | YM | MLYTTIYNMCTQKP | 54 |
| Sp C17G6.12 | 41 | GMTITK | YM | ELYTAIHNYCADAS | 62 |
| Sp C3A11.08 | 44 | LGLKTG | YQ | ELYSGVENLTRADQ | 65 |
| Ce Cul2 | 47 | PITNVQ | WH | HKFSDVYDICVSIP | 68 |
| Hs Cul2 | 29 | YVERAT | WN | DRFSDIYALCVAYP | 50 |
| Ce Cul3 | 25 | QYVTQT | WE | LLKRAIQEIQRKNN | 46 |
| Ce Cul4 | 79 | GSVGRD | WA | VLSDNVFAILEDRK | 100 |
| Ce Cul5 | 22 | SVTPAA | WQ | DLFYHVYKITSWVD | 43 |
| Hs Cul5 | 34 | SVTKQQ | WF | DLFSDVHAVCLWDD | 55 |
| Sp C24H6.03 | 41 | -TSQLS | FE | ELYRNAYILVLHKY | 61 |
| Sc Culb | 41 | -MADLS | FE | QVYKTIYTIVLNKK | 61 |

SEQUENCE LISTING

```
<160> NUMBER OF SEQ ID NOS: 50

<210> SEQ ID NO 1
<211> LENGTH: 11
<212> TYPE: PRT
<213> ORGANISM: Saccharomyces cerevisiae

<400> SEQUENCE: 1

Met Glu Val Thr Ala Ile Tyr Asn Tyr Cys Val
 1               5                  10

<210> SEQ ID NO 2
<211> LENGTH: 15
<212> TYPE: PRT
<213> ORGANISM: Saccharomyces cerevisiae

<400> SEQUENCE: 2

Tyr Met Glu Val Thr Ala Ile Tyr Asn Tyr Cys Val Asn Lys Ser
 1               5                  10                  15

<210> SEQ ID NO 3
<211> LENGTH: 22
<212> TYPE: PRT
<213> ORGANISM: Saccharomyces cerevisiae

<400> SEQUENCE: 3

Ile Leu Ser Pro Thr Met Tyr Met Glu Val Tyr Thr Ala Ile Tyr Asn
 1               5                  10                  15

Tyr Cys Val Asn Lys Ser
            20

<210> SEQ ID NO 4
<211> LENGTH: 13
<212> TYPE: PRT
<213> ORGANISM: Saccharomyces cerevisiae

<400> SEQUENCE: 4

Tyr Met Thr Leu Tyr Thr Ser Val Tyr Asp Tyr Cys Thr
 1               5                  10

<210> SEQ ID NO 5
<211> LENGTH: 16
<212> TYPE: PRT
```

```
<213> ORGANISM: Saccharomyces cerevisiae

<400> SEQUENCE: 5

Tyr Met Thr Leu Tyr Thr Ser Val Tyr Asp Tyr Cys Thr Ser Ile Thr
 1               5                  10                  15

<210> SEQ ID NO 6
<211> LENGTH: 21
<212> TYPE: PRT
<213> ORGANISM: Saccharomyces cerevisiae

<400> SEQUENCE: 6

Met Ala Pro Lys Asp Tyr Met Thr Leu Tyr Thr Ser Val Tyr Asp Tyr
 1               5                  10                  15

Cys Thr Ser Ile Thr
            20

<210> SEQ ID NO 7
<211> LENGTH: 13
<212> TYPE: PRT
<213> ORGANISM: Saccharomyces cerevisiae

<400> SEQUENCE: 7

Tyr Met Met Leu Tyr Asp Ala Val Tyr Asn Ile Cys Thr
 1               5                  10

<210> SEQ ID NO 8
<211> LENGTH: 16
<212> TYPE: PRT
<213> ORGANISM: Saccharomyces cerevisiae

<400> SEQUENCE: 8

Tyr Met Met Leu Tyr Asp Ala Val Tyr Asn Ile Cys Thr Thr Thr Thr
 1               5                  10                  15

<210> SEQ ID NO 9
<211> LENGTH: 22
<212> TYPE: PRT
<213> ORGANISM: Saccharomyces cerevisiae

<400> SEQUENCE: 9

His Met Ser Lys Lys Tyr Tyr Met Met Leu Tyr Asp Ala Val Tyr Asn
 1               5                  10                  15

Ile Cys Thr Thr Thr Thr
            20

<210> SEQ ID NO 10
<211> LENGTH: 13
<212> TYPE: PRT
<213> ORGANISM: Saccharomyces cerevisiae

<400> SEQUENCE: 10

Tyr Met Arg Phe Tyr Thr His Val Tyr Asp Tyr Cys Thr
 1               5                  10

<210> SEQ ID NO 11
<211> LENGTH: 16
<212> TYPE: PRT
<213> ORGANISM: Saccharomyces cerevisiae

<400> SEQUENCE: 11

Tyr Met Arg Phe Tyr Thr His Val Tyr Asp Tyr Cys Thr Ser Val Ser
 1               5                  10                  15
```

```
<210> SEQ ID NO 12
<211> LENGTH: 22
<212> TYPE: PRT
<213> ORGANISM: Saccharomyces cerevisiae

<400> SEQUENCE: 12

Ser Leu Thr Arg Ser Gln Tyr Met Arg Phe Tyr Thr His Val Tyr Asp
 1               5                  10                  15

Tyr Cys Thr Ser Val Ser
            20

<210> SEQ ID NO 13
<211> LENGTH: 13
<212> TYPE: PRT
<213> ORGANISM: Saccharomyces cerevisiae

<400> SEQUENCE: 13

Tyr Met Glu Leu Tyr Thr His Val Tyr Asn Tyr Cys Thr
 1               5                  10

<210> SEQ ID NO 14
<211> LENGTH: 16
<212> TYPE: PRT
<213> ORGANISM: Saccharomyces cerevisiae

<400> SEQUENCE: 14

Tyr Met Glu Leu Tyr Thr His Val Tyr Asn Tyr Cys Thr Ser Val His
 1               5                  10                  15

<210> SEQ ID NO 15
<211> LENGTH: 22
<212> TYPE: PRT
<213> ORGANISM: Saccharomyces cerevisiae

<400> SEQUENCE: 15

Ser Met Ala Lys Ser Arg Tyr Met Glu Leu Tyr Thr His Val Tyr Asn
 1               5                  10                  15

Tyr Cys Thr Ser Val His
            20

<210> SEQ ID NO 16
<211> LENGTH: 13
<212> TYPE: PRT
<213> ORGANISM: Saccharomyces cerevisiae

<400> SEQUENCE: 16

Tyr Met Met Leu Tyr Thr Thr Ile Tyr Asn Met Cys Thr
 1               5                  10

<210> SEQ ID NO 17
<211> LENGTH: 16
<212> TYPE: PRT
<213> ORGANISM: Saccharomyces cerevisiae

<400> SEQUENCE: 17

Tyr Met Met Leu Tyr Thr Thr Ile Tyr Asn Met Cys Thr Gln Lys Pro
 1               5                  10                  15

<210> SEQ ID NO 18
<211> LENGTH: 22
<212> TYPE: PRT
<213> ORGANISM: Saccharomyces cerevisiae

<400> SEQUENCE: 18
```

```
Ala Phe Asp Ser Glu Gln Tyr Met Met Leu Tyr Thr Thr Ile Tyr Asn
 1               5                  10                  15

Met Cys Thr Gln Lys Pro
            20
```

<210> SEQ ID NO 19
<211> LENGTH: 13
<212> TYPE: PRT
<213> ORGANISM: Saccharomyces cerevisiae

<400> SEQUENCE: 19

```
Tyr Met Glu Leu Tyr Thr Ala Ile His Asn Thr Cys Ala
 1               5                  10
```

<210> SEQ ID NO 20
<211> LENGTH: 16
<212> TYPE: PRT
<213> ORGANISM: Saccharomyces cerevisiae

<400> SEQUENCE: 20

```
Tyr Met Glu Leu Tyr Thr Ala Ile His Asn Thr Cys Ala Asp Ala Ser
 1               5                  10                  15
```

<210> SEQ ID NO 21
<211> LENGTH: 21
<212> TYPE: PRT
<213> ORGANISM: Saccharomyces cerevisiae

<400> SEQUENCE: 21

```
Gly Met Ile Thr Phe Tyr Met Glu Leu Tyr Thr Ala Ile His Asn Thr
 1               5                  10                  15

Cys Ala Asp Ala Ser
            20
```

<210> SEQ ID NO 22
<211> LENGTH: 295
<212> TYPE: PRT
<213> ORGANISM: Saccharomyces cerevisiae

<400> SEQUENCE: 22

```
Met Ser Ser Arg Lys Ser Thr Ala Ser Ser Leu Leu Leu Arg Gln Tyr
 1               5                  10                  15

Arg Glu Leu Thr Asp Pro Lys Lys Ala Ile Pro Ser Phe His Ile Glu
                20                  25                  30

Leu Glu Asp Asp Ser Asn Ile Phe Thr Trp Asn Ile Gly Val Met Val
            35                  40                  45

Leu Asn Glu Asp Ser Ile Tyr His Gly Gly Phe Phe Lys Ala Gln Met
        50                  55                  60

Arg Phe Pro Glu Asp Phe Pro Ser Pro Gln Phe Arg Phe Thr
 65                  70                  75                  80

Pro Ala Ile Tyr His Pro Asn Val Tyr Arg Asp Gly Arg Leu Cys Ile
                85                  90                  95

Ser Ile Leu His Gln Ser Gly Asp Pro Met Thr Asp Glu Pro Asp Ala
            100                 105                 110

Glu Thr Trp Ser Pro Val Gln Thr Val Glu Ser Val Leu Ile Ser Ile
        115                 120                 125

Val Ser Leu Leu Glu Asp Pro Asn Ile Asn Ser Pro Ala Asn Val Asp
    130                 135                 140

Ala Ala Val Asp Tyr Arg Lys Asn Pro Glu Gln Tyr Lys Gln Arg Val
```

```
145                 150                 155                 160
Lys Met Glu Val Glu Arg Ser Lys Gln Asp Ile Pro Lys Gly Phe Ile
                165                 170                 175
Met Pro Thr Ser Glu Ser Ala Tyr Ile Ser Gln Ser Lys Leu Asp Glu
                180                 185                 190
Pro Glu Ser Asn Lys Asp Met Ala Asp Asn Phe Trp Tyr Asp Ser Asp
                195                 200                 205
Leu Asp Asp Asp Glu Asn Gly Ser Val Ile Leu Gln Asp Asp Asp Tyr
            210                 215                 220
Asp Asp Gly Asn Asn His Ile Pro Phe Glu Asp Asp Val Tyr Asn
225                 230                 235                 240
Tyr Asn Asp Asn Asp Asp Asp Glu Arg Ile Glu Phe Glu Asp Asp
                245                 250                 255
Asp Asp Asp Asp Asp Asp Ser Ile Asp Asn Asp Ser Val Met Asp Arg
                260                 265                 270
Lys Gln Pro His Lys Ala Glu Asp Glu Ser Glu Asp Val Glu Asp Val
            275                 280                 285
Glu Arg Val Ser Lys Lys Ile
            290                 295

<210> SEQ ID NO 23
<211> LENGTH: 298
<212> TYPE: PRT
<213> ORGANISM: Saccharomyces cerevisiae

<400> SEQUENCE: 23

Ile Ala Ala Ala Pro Glu Leu Leu Glu Arg Ser Gly Ser Pro Gly Gly
1               5                   10                  15
Gly Gly Gly Ala Glu Glu Glu Ala Gly Gly Pro Gly Gly Ser Pro
                20                  25                  30
Pro Asp Gly Ala Arg Pro Gly Pro Ser Arg Glu Leu Ala Val Val Ala
            35                  40                  45
Arg Pro Arg Ala Ala Pro Thr Pro Gly Pro Ser Ala Ala Ala Met Ala
        50                  55                  60
Arg Pro Leu Val Pro Ser Ser Gln Lys Ala Leu Leu Leu Glu Leu Lys
65                  70                  75                  80
Gly Leu Gln Glu Glu Pro Val Glu Gly Phe Arg Val Thr Leu Val Asp
                85                  90                  95
Glu Gly Asp Leu Tyr Asn Trp Glu Val Ala Ile Phe Gly Pro Pro Asn
                100                 105                 110
Thr Tyr Tyr Glu Gly Gly Tyr Phe Lys Ala Arg Leu Lys Phe Pro Ile
            115                 120                 125
Asp Tyr Pro Tyr Ser Pro Pro Ala Phe Arg Phe Leu Thr Lys Met Trp
        130                 135                 140
His Pro Asn Ile Tyr Glu Thr Gly Asp Val Cys Ile Ser Ile Leu His
145                 150                 155                 160
Pro Pro Val Asp Asp Pro Gln Ser Gly Glu Leu Pro Ser Glu Arg Trp
                165                 170                 175
Asn Pro Thr Gln Asn Val Arg Thr Ile Leu Leu Ser Val Ile Ser Leu
                180                 185                 190
Leu Asn Glu Pro Asn Thr Phe Ser Pro Ala Asn Val Asp Ala Ser Val
            195                 200                 205
Met Tyr Arg Lys Trp Lys Glu Ser Lys Gly Lys Asp Arg Glu Tyr Thr
        210                 215                 220
```

-continued

```
Asp Ile Ile Arg Lys Gln Val Leu Gly Thr Lys Val Asp Ala Glu Arg
225                 230                 235                 240

Asp Gly Val Lys Val Pro Thr Thr Leu Ala Glu Tyr Cys Val Lys Thr
            245                 250                 255

Lys Ala Pro Ala Pro Asp Glu Gly Ser Asp Leu Phe Tyr Asp Asp Tyr
        260                 265                 270

Tyr Glu Asp Gly Glu Val Glu Glu Ala Asp Ser Cys Phe Gly Asp
    275                 280                 285

Asp Glu Asp Asp Ser Gly Thr Glu Ser
    290                 295
```

<210> SEQ ID NO 24
<211> LENGTH: 815
<212> TYPE: PRT
<213> ORGANISM: Saccharomyces cerevisiae

<400> SEQUENCE: 24

```
Met Ser Glu Thr Leu Pro Arg Ser Asp Asp Leu Glu Ala Thr Trp Asn
1               5                   10                  15

Phe Ile Glu Pro Gly Ile Asn Gln Ile Leu Gly Asn Glu Lys Asn Gln
            20                  25                  30

Ala Ser Thr Ser Lys Arg Val Tyr Lys Ile Leu Ser Pro Thr Met Tyr
        35                  40                  45

Met Glu Val Tyr Thr Ala Ile Tyr Asn Tyr Cys Val Asn Lys Ser Arg
    50                  55                  60

Ser Ser Gly His Phe Ser Thr Asp Ser Arg Thr Gly Gln Ser Thr Ile
65                  70                  75                  80

Leu Val Gly Ser Glu Ile Tyr Glu Lys Leu Lys Asn Tyr Leu Lys Asn
                85                  90                  95

Tyr Ile Leu Asn Phe Lys Gln Ser Asn Ser Glu Thr Phe Leu Gln Phe
            100                 105                 110

Tyr Val Lys Arg Trp Lys Arg Phe Thr Ile Gly Ala Ile Phe Leu Asn
        115                 120                 125

His Ala Phe Asp Tyr Met Asn Arg Tyr Trp Val Gln Lys Glu Arg Ser
    130                 135                 140

Asp Gly Lys Arg His Ile Phe Asp Val Asn Thr Leu Cys Leu Met Thr
145                 150                 155                 160

Trp Lys Glu Val Met Phe Asp Pro Ser Lys Asp Val Leu Ile Asn Glu
                165                 170                 175

Leu Leu Asp Gln Val Thr Leu Gly Arg Glu Gly Gln Ile Ile Gln Arg
            180                 185                 190

Ser Asn Ile Ser Thr Ala Ile Lys Ser Leu Val Ala Leu Gly Ile Asp
        195                 200                 205

Pro Gln Asp Leu Lys Lys Leu Asn Leu Asn Val Tyr Ile Gln Val Phe
    210                 215                 220

Glu Lys Pro Phe Leu Lys Lys Thr Gln Glu Tyr Tyr Thr Gln Tyr Thr
225                 230                 235                 240

Asn Asp Tyr Leu Glu Lys His Ser Val Thr Glu Tyr Ile Phe Glu Ala
                245                 250                 255

His Glu Ile Ile Lys Arg Glu Glu Lys Ala Met Thr Ile Tyr Trp Asp
            260                 265                 270

Asp His Thr Lys Lys Pro Leu Ser Met Ala Leu Asn Lys Val Leu Ile
        275                 280                 285

Thr Asp His Ile Glu Lys Leu Glu Asn Glu Phe Val Val Leu Leu Asp
    290                 295                 300
```

-continued

```
Ala Arg Asp Ile Glu Lys Ile Thr Ser Leu Tyr Ala Leu Ile Arg Arg
305                 310                 315                 320

Asp Phe Thr Leu Ile Pro Arg Met Ala Ser Val Phe Glu Asn Tyr Val
                325                 330                 335

Lys Lys Thr Gly Glu Asn Glu Ile Ser Ser Leu Leu Ala Met His Lys
                340                 345                 350

His Asn Ile Met Lys Asn Glu Asn Ala Asn Pro Lys Lys Leu Ala Leu
            355                 360                 365

Met Thr Ala His Ser Leu Ser Pro Lys Asp Tyr Ile Lys Lys Leu Leu
370                 375                 380

Glu Val His Asp Ile Phe Ser Lys Ile Phe Asn Glu Ser Phe Pro Asp
385                 390                 395                 400

Asp Ile Pro Leu Ala Lys Ala Leu Asp Asn Ala Cys Gly Ala Phe Ile
                405                 410                 415

Asn Ile Asn Glu Phe Ala Leu Pro Ala Gly Ser Pro Lys Ser Ala Thr
                420                 425                 430

Ser Lys Thr Ser Glu Met Leu Ala Lys Tyr Ser Asp Ile Leu Leu Lys
            435                 440                 445

Lys Ala Thr Lys Pro Glu Val Ala Ser Asp Met Ser Asp Glu Asp Ile
450                 455                 460

Ile Thr Ile Phe Lys Tyr Leu Thr Asp Lys Asp Ala Phe Glu Thr His
465                 470                 475                 480

Tyr Arg Arg Leu Phe Ala Lys Arg Leu Ile His Gly Thr Ser Thr Ser
                485                 490                 495

Ala Glu Asp Glu Glu Asn Ile Ile Gln Arg Leu Gln Ala Ala Asn Ser
            500                 505                 510

Met Glu Tyr Thr Gly Lys Ile Thr Lys Met Phe Gln Asp Ile Arg Leu
            515                 520                 525

Ser Lys Ile Leu Glu Asp Asp Phe Ala Val Ala Leu Lys Asn Glu Pro
            530                 535                 540

Asp Tyr Ser Lys Ala Lys Tyr Pro Asp Leu Gln Pro Phe Val Leu Ala
545                 550                 555                 560

Glu Asn Met Trp Pro Phe Ser Tyr Gln Glu Val Glu Phe Lys Leu Pro
                565                 570                 575

Lys Glu Leu Val Pro Ser His Glu Lys Leu Lys Glu Ser Tyr Ser Gln
                580                 585                 590

Lys His Asn Gly Arg Ile Leu Lys Trp Leu Trp Pro Leu Cys Arg Gly
            595                 600                 605

Glu Leu Lys Ala Asp Ile Gly Lys Pro Gly Arg Met Pro Phe Asn Phe
            610                 615                 620

Thr Val Thr Leu Phe Gln Met Ala Ile Leu Leu Leu Tyr Asn Asp Ala
625                 630                 635                 640

Asp Val Leu Thr Leu Glu Asn Ile Gln Glu Gly Thr Ser Leu Thr Ile
                645                 650                 655

Gln His Ile Ala Ala Met Val Pro Phe Ile Lys Phe Lys Leu Ile
            660                 665                 670

Gln Gln Val Pro Pro Gly Leu Asp Ala Leu Val Lys Pro Glu Thr Gln
            675                 680                 685

Phe Lys Leu Ser Arg Pro Tyr Lys Ala Leu Lys Thr Asn Ile Asn Phe
690                 695                 700

Ala Ser Gly Val Lys Asn Asp Ile Leu Gln Ser Leu Ser Gly Gly Gly
705                 710                 715                 720
```

```
His Asp Asn His Gly Asn Lys Leu Gly Asn Lys Arg Leu Thr Glu Asp
                725                 730                 735

Glu Arg Ile Glu Lys Glu Leu Asn Thr Glu Arg Gln Ile Phe Leu Glu
            740                 745                 750

Ala Cys Ile Val Arg Ile Met Lys Ala Lys Arg Asn Leu Pro His Thr
        755                 760                 765

Thr Leu Val Asn Glu Cys Ile Ala Gln Ser His Gln Arg Phe Asn Ala
    770                 775                 780

Lys Val Ser Met Val Lys Arg Ala Ile Asp Ser Leu Ile Gln Lys Gly
785                 790                 795                 800

Tyr Leu Gln Arg Gly Asp Asp Gly Glu Ser Tyr Ala Tyr Leu Ala
                805                 810                 815

<210> SEQ ID NO 25
<211> LENGTH: 745
<212> TYPE: PRT
<213> ORGANISM: Saccharomyces cerevisiae

<400> SEQUENCE: 25

Met Ser Leu Lys Pro Arg Val Val Asp Phe Asp Glu Thr Trp Asn Lys
  1               5                  10                  15

Leu Leu Thr Thr Ile Lys Ala Val Val Met Leu Glu Tyr Val Glu Arg
             20                  25                  30

Ala Thr Trp Asn Asp Arg Phe Ser Asp Ile Tyr Ala Leu Cys Val Ala
         35                  40                  45

Tyr Pro Glu Pro Leu Gly Glu Arg Leu Tyr Thr Glu Thr Lys Ile Phe
     50                  55                  60

Leu Glu Asn His Val Arg His Leu His Lys Arg Val Leu Glu Ser Glu
 65                  70                  75                  80

Glu Gln Val Leu Val Met Tyr His Arg Tyr Trp Glu Glu Tyr Ser Lys
                 85                  90                  95

Gly Ala Asp Tyr Met Asp Cys Leu Tyr Arg Tyr Leu Ser Thr Gln Phe
            100                 105                 110

Ile Lys Lys Asn Lys Leu Thr Glu Ala Asp Leu Gln Tyr Gly Tyr Gly
        115                 120                 125

Gly Val Asp Met Asn Glu Pro Leu Met Glu Ile Gly Glu Leu Ala Leu
    130                 135                 140

Asp Met Trp Arg Lys Leu Met Val Glu Pro Leu Gln Ala Ile Leu Ile
145                 150                 155                 160

Arg Met Leu Leu Arg Glu Ile Lys Asn Asp Arg Gly Gly Glu Asp Pro
                165                 170                 175

Asn Gln Lys Val Ile His Gly Val Ile Asn Ser Phe Val His Val Glu
            180                 185                 190

Gln Tyr Lys Lys Lys Phe Pro Leu Lys Phe Tyr Gln Glu Ile Phe Glu
        195                 200                 205

Ser Pro Phe Leu Thr Glu Thr Gly Glu Tyr Tyr Lys Gln Glu Ala Ser
    210                 215                 220

Asn Leu Leu Gln Glu Ser Asn Cys Ser Gln Tyr Met Glu Lys Val Leu
225                 230                 235                 240

Gly Arg Leu Lys Asp Glu Glu Ile Arg Cys Arg Lys Tyr Leu His Pro
                245                 250                 255

Ser Ser Tyr Thr Lys Val Ile His Glu Cys Gln Gln Arg Met Val Ala
            260                 265                 270

Asp His Leu Gln Phe Leu His Ala Glu Cys His Asn Ile Ile Arg Gln
        275                 280                 285
```

```
Glu Lys Lys Asn Asp Met Ala Asn Met Tyr Val Leu Leu Arg Ala Val
    290                 295                 300
Ser Thr Gly Leu Pro His Met Ile Gln Glu Leu Gln Asn His Ile His
305                 310                 315                 320
Asp Glu Gly Leu Arg Ala Thr Ser Asn Leu Thr Gln Glu Asn Met Pro
                325                 330                 335
Thr Leu Phe Val Glu Ser Val Leu Glu Val His Gly Lys Phe Val Gln
                340                 345                 350
Leu Ile Asn Thr Val Leu Asn Gly Asp Gln His Phe Met Ser Ala Leu
        355                 360                 365
Asp Lys Ala Leu Thr Ser Val Val Asn Tyr Arg Glu Pro Lys Ser Val
        370                 375                 380
Cys Lys Ala Pro Glu Leu Leu Ala Lys Tyr Cys Asp Asn Leu Leu Lys
385                 390                 395                 400
Lys Ser Ala Lys Gly Met Thr Glu Asn Glu Val Glu Asp Arg Leu Thr
                405                 410                 415
Ser Phe Ile Thr Val Phe Lys Tyr Ile Asp Asp Lys Asp Val Phe Gln
                420                 425                 430
Lys Phe Tyr Ala Arg Met Leu Ala Lys Arg Leu Ile His Gly Leu Ser
        435                 440                 445
Met Ser Met Asp Ser Glu Glu Ala Met Ile Asn Lys Leu Lys Gln Ala
        450                 455                 460
Cys Gly Tyr Glu Phe Thr Ser Lys Leu His Arg Met Tyr Thr Asp Met
465                 470                 475                 480
Ser Val Ser Ala Asp Leu Asn Asn Lys Phe Asn Asn Phe Ile Lys Asn
                485                 490                 495
Gln Asp Thr Val Ile Asp Leu Gly Ile Ser Phe Gln Ile Tyr Val Leu
                500                 505                 510
Gln Ala Gly Ala Trp Pro Leu Thr Gln Ala Pro Ser Ser Thr Phe Ala
        515                 520                 525
Ile Pro Gln Glu Leu Glu Lys Ser Val Gln Met Phe Glu Leu Phe Tyr
        530                 535                 540
Ser Gln His Phe Ser Gly Arg Lys Leu Thr Trp Leu His Tyr Leu Cys
545                 550                 555                 560
Thr Gly Glu Val Lys Met Asn Tyr Leu Gly Lys Pro Tyr Val Ala Met
                565                 570                 575
Val Thr Thr Tyr Gln Met Ala Val Leu Leu Ala Phe Asn Asn Ser Glu
                580                 585                 590
Thr Val Ser Tyr Lys Glu Leu Gln Asp Ser Thr Gln Met Asn Glu Lys
        595                 600                 605
Glu Leu Thr Lys Thr Ile Lys Ser Leu Leu Asp Val Lys Met Ile Asn
        610                 615                 620
His Asp Ser Glu Lys Glu Asp Ile Asp Ala Glu Ser Ser Phe Ser Leu
625                 630                 635                 640
Asn Met Asn Phe Ser Ser Lys Arg Thr Lys Phe Lys Ile Thr Thr Ser
                645                 650                 655
Met Gln Lys Asp Thr Pro Gln Glu Met Glu Gln Thr Arg Ser Ala Val
                660                 665                 670
Asp Glu Asp Arg Lys Met Tyr Leu Gln Ala Ala Ile Val Arg Ile Met
        675                 680                 685
Lys Ala Arg Lys Val Leu Arg His Asn Ala Leu Ile Gln Glu Val Ile
        690                 695                 700
```

-continued

Ser Gln Ser Arg Ala Arg Phe Asn Pro Ser Ile Ser Met Ile Lys Lys
705                 710                 715                 720

Cys Ile Glu Val Leu Ile Asp Lys Gln Tyr Ile Glu Arg Ser Gln Ala
                725                 730                 735

Ser Ala Asp Glu Tyr Ser Tyr Val Ala
                740                 745

<210> SEQ ID NO 26
<211> LENGTH: 301
<212> TYPE: PRT
<213> ORGANISM: Saccharomyces cerevisiae

<400> SEQUENCE: 26

Lys Lys Ala Thr Lys Pro Glu Val Ala Ser Asp Met Ser Asp Glu Asp
1               5                   10                  15

Ile Ile Thr Ile Phe Lys Tyr Leu Thr Asp Lys Asp Ala Phe Glu Thr
            20                  25                  30

His Tyr Arg Arg Leu Phe Ala Lys Arg Leu Ile His Gly Thr Ser Thr
        35                  40                  45

Ser Ala Glu Asp Glu Glu Asn Ile Ile Gln Arg Leu Gln Ala Ala Asn
    50                  55                  60

Ser Met Glu Tyr Thr Gly Lys Ile Thr Lys Met Phe Gln Asp Ile Arg
65                  70                  75                  80

Leu Ser Lys Ile Leu Glu Asp Asp Phe Ala Val Ala Leu Lys Asn Glu
                85                  90                  95

Pro Asp Tyr Ser Lys Ala Lys Tyr Pro Asp Leu Gln Pro Phe Val Leu
            100                 105                 110

Ala Glu Asn Met Trp Pro Phe Ser Tyr Gln Glu Val Glu Phe Lys Leu
        115                 120                 125

Pro Lys Glu Leu Val Pro Ser His Glu Lys Leu Lys Glu Ser Tyr Ser
130                 135                 140

Gln Lys His Asn Gly Arg Ile Leu Lys Trp Leu Trp Pro Leu Cys Arg
145                 150                 155                 160

Gly Glu Leu Lys Ala Asp Ile Gly Lys Pro Gly Arg Met Pro Phe Asn
                165                 170                 175

Phe Thr Val Thr Leu Phe Gln Met Ala Ile Leu Leu Leu Tyr Asn Asp
            180                 185                 190

Ala Asp Val Leu Thr Leu Glu Asn Ile Gln Glu Gly Thr Ser Leu Thr
        195                 200                 205

Ile Gln His Ile Ala Ala Ala Met Val Pro Phe Ile Lys Phe Lys Leu
    210                 215                 220

Ile Gln Gln Val Pro Pro Gly Leu Asp Ala Leu Val Lys Pro Glu Thr
225                 230                 235                 240

Gln Phe Lys Leu Ser Arg Pro Tyr Lys Ala Leu Lys Thr Asn Ile Asn
                245                 250                 255

Phe Ala Ser Gly Val Lys Asn Asp Ile Leu Gln Ser Leu Ser Gly Gly
            260                 265                 270

Gly His Asp Asn His Gly Asn Lys Leu Gly Asn Lys Arg Leu Thr Glu
        275                 280                 285

Asp Glu Arg Ile Glu Lys Glu Leu Asn Thr Glu Arg Gln
    290                 295                 300

<210> SEQ ID NO 27
<211> LENGTH: 272
<212> TYPE: PRT
<213> ORGANISM: Saccharomyces cerevisiae

```
<400> SEQUENCE: 27

Asp Asp Leu Glu Ala Thr Trp Asn Phe Ile Glu Pro Gly Ile Asn Gln
  1               5                  10                  15

Ile Leu Gly Asn Glu Lys Asn Gln Ala Ser Thr Ser Lys Arg Val Tyr
             20                  25                  30

Lys Ile Leu Ser Pro Thr Met Tyr Met Glu Val Tyr Thr Ala Ile Tyr
         35                  40                  45

Asn Tyr Cys Val Asn Lys Ser Arg Ser Ser Gly His Phe Ser Thr Asp
     50                  55                  60

Ser Arg Thr Gly Gln Ser Thr Ile Leu Val Gly Ser Glu Ile Tyr Glu
 65                  70                  75                  80

Lys Leu Lys Asn Tyr Leu Lys Asn Tyr Ile Leu Asn Phe Lys Gln Ser
                 85                  90                  95

Asn Ser Glu Thr Phe Leu Gln Phe Tyr Val Lys Arg Trp Lys Arg Phe
            100                 105                 110

Thr Ile Gly Ala Ile Phe Leu Asn His Ala Phe Asp Tyr Met Asn Arg
        115                 120                 125

Tyr Trp Val Gln Lys Glu Arg Ser Asp Gly Lys Arg His Ile Phe Asp
    130                 135                 140

Val Asn Thr Leu Cys Leu Met Thr Trp Lys Glu Val Met Phe Asp Pro
145                 150                 155                 160

Ser Lys Asp Val Leu Ile Asn Glu Leu Leu Asp Gln Val Thr Leu Gly
                165                 170                 175

Arg Glu Gly Gln Ile Ile Gln Arg Ser Asn Ile Ser Thr Ala Ile Lys
            180                 185                 190

Ser Leu Val Ala Leu Gly Ile Asp Pro Gln Asp Leu Lys Lys Leu Asn
        195                 200                 205

Leu Asn Val Tyr Ile Gln Val Phe Glu Lys Pro Phe Leu Lys Lys Thr
    210                 215                 220

Gln Glu Tyr Tyr Thr Gln Tyr Thr Asn Asp Tyr Leu Glu Lys His Ser
225                 230                 235                 240

Val Thr Glu Tyr Ile Phe Glu Ala His Glu Ile Ile Lys Arg Glu Glu
                245                 250                 255

Lys Ala Met Thr Ile Tyr Trp Asp Asp His Thr Lys Lys Pro Leu Ser
            260                 265                 270

<210> SEQ ID NO 28
<211> LENGTH: 194
<212> TYPE: PRT
<213> ORGANISM: Saccharomyces cerevisiae

<400> SEQUENCE: 28

Met Val Thr Ser Asn Val Val Leu Val Ser Gly Glu Gly Glu Arg Phe
  1               5                  10                  15

Thr Val Asp Lys Lys Ile Ala Glu Arg Ser Leu Leu Leu Lys Asn Tyr
             20                  25                  30

Leu Asn Asp Met His Asp Ser Asn Leu Gln Asn Asn Ser Asp Ser Asp
         35                  40                  45

Ser Asp Ser Asp Ser Glu Thr Asn His Lys Ser Lys Asp Asn Asn Asn
     50                  55                  60

Gly Asp Asp Asp Asp Glu Asp Asp Glu Ile Val Met Pro Val Pro
 65                  70                  75                  80

Asn Val Arg Ser Ser Val Leu Gln Lys Val Ile Glu Trp Ala Glu His
                 85                  90                  95
```

-continued

His Arg Asp Ser Asn Phe Pro Asp Glu Asp Asp Asp Ser Arg Lys
            100                 105                 110

Ser Ala Pro Val Asp Ser Trp Asp Arg Glu Phe Leu Lys Val Asp Gln
        115                 120                 125

Glu Met Leu Tyr Glu Ile Ile Leu Ala Ala Asn Tyr Leu Asn Ile Lys
        130                 135                 140

Pro Leu Leu Asp Ala Gly Cys Lys Val Val Ala Glu Met Ile Arg Gly
145                 150                 155                 160

Arg Ser Pro Glu Glu Ile Arg Arg Thr Phe Asn Ile Val Asn Asp Phe
                165                 170                 175

Thr Pro Glu Glu Glu Ala Ala Ile Arg Arg Glu Asn Glu Trp Ala Glu
                180                 185                 190

Asp Arg

<210> SEQ ID NO 29
<211> LENGTH: 779
<212> TYPE: PRT
<213> ORGANISM: Saccharomyces cerevisiae

<400> SEQUENCE: 29

Met Gly Ser Phe Pro Leu Ala Glu Phe Pro Leu Arg Asp Ile Pro Val
 1               5                  10                  15

Pro Tyr Ser Tyr Arg Val Ser Gly Gly Ile Ala Ser Ser Gly Ser Val
                20                  25                  30

Thr Ala Leu Val Thr Ala Ala Gly Thr His Arg Asn Ser Ser Thr Ala
            35                  40                  45

Lys Thr Val Glu Thr Glu Asp Gly Glu Asp Ile Asp Glu Tyr Gln
        50                  55                  60

Arg Lys Arg Ala Ala Gly Ser Gly Glu Ser Thr Pro Glu Arg Ser Asp
 65                  70                  75                  80

Phe Lys Arg Val Lys His Asp Asn His Lys Thr Leu His Pro Val Asn
                85                  90                  95

Leu Gln Asn Thr Gly Ala Ala Ser Val Asp Asn Asp Gly Leu His Asn
            100                 105                 110

Leu Thr Asp Ile Ser Asn Asp Ala Glu Lys Leu Leu Met Ser Val Asp
        115                 120                 125

Asp Gly Ser Ala Ala Pro Ser Thr Leu Ser Val Asn Met Gly Val Ala
        130                 135                 140

Ser His Asn Val Ala Ala Pro Thr Thr Val Asn Ala Ala Thr Ile Thr
145                 150                 155                 160

Gly Ser Asp Val Ser Asn Asn Val Asn Ser Ala Thr Ile Asn Asn Pro
                165                 170                 175

Met Glu Glu Gly Ala Leu Pro Leu Ser Pro Thr Ala Ser Ser Pro Gly
                180                 185                 190

Thr Thr Thr Pro Leu Ala Lys Thr Thr Lys Thr Ile Asn Asn Asn Asn
            195                 200                 205

Asn Ile Ala Asp Leu Ile Glu Ser Lys Asp Ser Ile Ile Ser Pro Glu
        210                 215                 220

Tyr Leu Ser Asp Glu Ile Phe Ser Ala Ile Asn Asn Leu Pro His
225                 230                 235                 240

Ala Tyr Phe Lys Asn Leu Leu Phe Arg Leu Val Ala Asn Met Asp Arg
                245                 250                 255

Ser Glu Leu Ser Asp Leu Gly Thr Leu Ile Lys Asp Asn Leu Lys Arg
                260                 265                 270

-continued

```
Asp Leu Ile Thr Ser Leu Pro Phe Glu Ile Ser Leu Lys Ile Phe Asn
            275                 280                 285

Tyr Leu Gln Phe Glu Asp Ile Ile Asn Ser Leu Gly Val Ser Gln Asn
        290                 295                 300

Trp Asn Lys Ile Ile Arg Lys Ser Thr Ser Leu Trp Lys Lys Leu Leu
305                 310                 315                 320

Ile Ser Glu Asn Phe Val Ser Pro Lys Gly Phe Asn Ser Leu Asn Leu
                325                 330                 335

Lys Leu Ser Gln Lys Tyr Pro Lys Leu Ser Gln Gln Asp Arg Leu Arg
            340                 345                 350

Leu Ser Phe Leu Glu Asn Ile Phe Ile Leu Lys Asn Trp Tyr Asn Pro
        355                 360                 365

Lys Phe Val Pro Gln Arg Thr Thr Leu Arg Gly His Met Thr Ser Val
    370                 375                 380

Ile Thr Cys Leu Gln Phe Glu Asp Asn Tyr Val Ile Thr Gly Ala Asp
385                 390                 395                 400

Asp Lys Met Ile Arg Val Tyr Asp Ser Ile Asn Lys Lys Phe Leu Leu
                405                 410                 415

Gln Leu Ser Gly His Asp Gly Gly Val Trp Ala Leu Lys Tyr Ala His
            420                 425                 430

Gly Gly Ile Leu Val Ser Gly Ser Thr Asp Arg Thr Val Arg Val Trp
        435                 440                 445

Asp Ile Lys Lys Gly Cys Cys Thr His Val Phe Lys Gly His Asn Ser
    450                 455                 460

Thr Val Arg Cys Leu Asp Ile Val Glu Tyr Lys Asn Ile Lys Tyr Ile
465                 470                 475                 480

Val Thr Gly Ser Arg Asp Asn Thr Leu His Val Trp Lys Leu Pro Lys
                485                 490                 495

Glu Ser Ser Val Pro Asp His Gly Glu Glu His Asp Tyr Pro Leu Val
            500                 505                 510

Phe His Thr Pro Glu Glu Asn Pro Tyr Phe Val Gly Val Leu Arg Gly
        515                 520                 525

His Met Ala Ser Val Arg Thr Val Ser Gly His Gly Asn Ile Val Val
    530                 535                 540

Ser Gly Ser Tyr Asp Asn Thr Leu Ile Val Trp Asp Val Ala Gln Met
545                 550                 555                 560

Lys Cys Leu Tyr Ile Leu Ser Gly His Thr Asp Arg Ile Tyr Ser Thr
                565                 570                 575

Ile Tyr Asp His Glu Arg Lys Arg Cys Ile Ser Ala Ser Met Asp Thr
            580                 585                 590

Thr Ile Arg Ile Trp Asp Leu Glu Asn Ile Trp Asn Asn Gly Glu Cys
        595                 600                 605

Ser Tyr Ala Thr Asn Ser Ala Ser Pro Cys Ala Lys Ile Leu Gly Ala
    610                 615                 620

Met Tyr Thr Leu Gln Gly His Thr Ala Leu Val Gly Leu Leu Arg Leu
625                 630                 635                 640

Ser Asp Lys Phe Leu Val Ser Ala Ala Asp Gly Ser Ile Arg Gly
                645                 650                 655

Trp Asp Ala Asn Asp Tyr Ser Arg Lys Phe Ser Tyr His His Thr Asn
            660                 665                 670

Leu Ser Ala Ile Thr Thr Phe Tyr Val Ser Asp Asn Ile Leu Val Ser
        675                 680                 685

Gly Ser Glu Asn Gln Phe Asn Ile Tyr Asn Leu Arg Ser Gly Lys Leu
```

```
                690                   695                   700
Val His Ala Asn Ile Leu Lys Asp Ala Asp Gln Ile Trp Ser Val Asn
705                 710                   715                   720

Phe Lys Gly Lys Thr Leu Val Ala Val Glu Lys Asp Gly Gln Ser
                725                   730                   735

Phe Leu Glu Ile Leu Asp Phe Ser Lys Ala Ser Lys Ile Asn Tyr Val
                740                   745                   750

Ser Asn Pro Val Asn Ser Ser Ser Ser Leu Glu Ser Ile Ser Thr
                755                   760                   765

Ser Leu Gly Leu Thr Arg Thr Thr Ile Ile Pro
                770                   775
```

<210> SEQ ID NO 30
<211> LENGTH: 640
<212> TYPE: PRT
<213> ORGANISM: Saccharomyces cerevisiae

<400> SEQUENCE: 30

```
Met Arg Arg Glu Arg Gln Arg Met Met Ser Phe Glu Asp Lys Asp Lys
  1               5                  10                  15

Asp Asp Leu Asp Asn Ser Asn Ser Asn Asn Ser Ser Glu Met Thr Asp
                 20                  25                  30

Thr Ala Met Met Pro Pro Leu Lys Arg Leu Leu Ile Thr Gly Ser Ser
             35                  40                  45

Asp Asp Leu Ala Gln Gly Ser Ser Gly Lys Lys Lys Met Thr Met Ala
         50                  55                  60

Thr Arg Ser Pro Ser Ser Pro Asp Leu Ala Thr Asn Asp Ser Gly
 65                  70                  75                  80

Thr Arg Val Gln Pro Leu Pro Glu Tyr Asn Phe Thr Lys Phe Cys Tyr
                 85                  90                  95

Arg His Asn Pro Asp Ile Gln Phe Ser Pro Thr His Thr Ala Cys Tyr
                100                 105                 110

Lys Gln Asp Leu Lys Arg Thr Gln Glu Ile Asn Ala Asn Ile Ala Lys
            115                 120                 125

Leu Pro Leu Gln Glu Gln Ser Asp Ile His His Ile Ile Ser Lys Tyr
        130                 135                 140

Ser Asn Ser Asn Asp Lys Ile Arg Lys Leu Ile Leu Asp Gly Ile Leu
145                 150                 155                 160

Ser Thr Ser Cys Phe Pro Gln Leu Ser Tyr Ile Ser Ser Leu Val Thr
                165                 170                 175

His Met Ile Lys Ile Asp Phe Ile Ser Ile Leu Pro Gln Glu Leu Ser
            180                 185                 190

Leu Lys Ile Leu Ser Tyr Leu Asp Cys Gln Ser Leu Cys Asn Ala Thr
        195                 200                 205

Arg Val Cys Arg Lys Trp Gln Lys Leu Ala Asp Asp Arg Val Trp
    210                 215                 220

Tyr His Met Cys Glu Gln His Ile Asp Arg Lys Cys Pro Asn Cys Gly
225                 230                 235                 240

Trp Gly Leu Pro Leu Leu His Met Lys Arg Ala Arg Ile Gln Gln Asn
                245                 250                 255

Ser Thr Gly Ser Ser Asn Ala Asp Ile Gln Thr Gln Thr Thr Arg
            260                 265                 270

Pro Trp Lys Val Ile Tyr Arg Glu Arg Phe Lys Val Glu Ser Asn Trp
        275                 280                 285
```

-continued

```
Arg Lys Gly His Cys Arg Ile Gln Glu Phe Lys Gly His Met Asp Gly
        290                 295                 300

Val Leu Thr Leu Gln Phe Asn Tyr Arg Leu Leu Phe Thr Gly Ser Tyr
305                 310                 315                 320

Asp Ser Thr Ile Gly Ile Trp Asp Leu Phe Thr Gly Lys Leu Ile Arg
                325                 330                 335

Arg Leu Ser Gly His Ser Asp Gly Val Lys Thr Leu Tyr Phe Asp Asp
            340                 345                 350

Arg Lys Leu Ile Thr Gly Ser Leu Asp Lys Thr Ile Arg Val Trp Asn
        355                 360                 365

Tyr Ile Thr Gly Glu Cys Ile Ser Thr Tyr Arg Gly His Ser Asp Ser
370                 375                 380

Val Leu Ser Val Asp Ser Tyr Gln Lys Val Ile Val Ser Gly Ser Ala
385                 390                 395                 400

Asp Lys Thr Val Lys Val Trp His Val Glu Ser Arg Thr Cys Tyr Thr
                405                 410                 415

Leu Arg Gly His Thr Glu Trp Val Asn Cys Val Lys Leu His Pro Lys
            420                 425                 430

Ser Phe Ser Cys Phe Ser Cys Ser Asp Asp Thr Thr Ile Arg Met Trp
        435                 440                 445

Asp Ile Arg Thr Asn Ser Cys Leu Lys Val Phe Arg Gly His Val Gly
450                 455                 460

Gln Val Gln Lys Ile Ile Pro Leu Thr Ile Lys Asp Val Glu Asn Leu
465                 470                 475                 480

Ala Thr Asp Asn Thr Ser Asp Gly Ser Ser Pro Gln Asp Asp Pro Thr
                485                 490                 495

Met Thr Asp Gly Ala Asp Glu Ser Asp Thr Pro Ser Asn Glu Gln Glu
            500                 505                 510

Thr Val Leu Asp Glu Asn Ile Pro Tyr Pro Thr His Leu Leu Ser Cys
        515                 520                 525

Gly Leu Asp Asn Thr Ile Lys Leu Trp Asp Val Lys Thr Gly Lys Cys
530                 535                 540

Ile Arg Thr Gln Phe Gly His Val Glu Gly Val Trp Asp Ile Ala Ala
545                 550                 555                 560

Asp Asn Phe Arg Ile Ile Ser Gly Ser His Asp Gly Ser Ile Lys Val
                565                 570                 575

Trp Asp Leu Gln Ser Gly Lys Cys Met His Thr Phe Asn Gly Arg Arg
            580                 585                 590

Leu Gln Arg Glu Thr Gln His Thr Gln Thr Gln Ser Leu Gly Asp Lys
        595                 600                 605

Val Ala Pro Ile Ala Cys Val Cys Ile Gly Asp Ser Glu Cys Phe Ser
610                 615                 620

Gly Asp Glu Phe Gly Cys Val Lys Met Tyr Lys Phe Asp Leu Asn Asp
625                 630                 635                 640
```

<210> SEQ ID NO 31
<211> LENGTH: 1151
<212> TYPE: PRT
<213> ORGANISM: Saccharomyces cerevisiae

<400> SEQUENCE: 31

```
Met Asp Gln Asp Asn Asn Asn His Asn Asp Ser Asn Arg Leu His Pro
 1               5                  10                  15

Pro Asp Ile His Pro Asn Leu Gly Pro Gln Leu Trp Leu Asn Ser Ser
            20                  25                  30
```

-continued

```
Gly Asp Phe Asp Asp Asn Asn Asn Asn Asn Asn Asn Asn
         35                  40                  45

Asn Ser Thr Arg Pro Gln Met Pro Ser Arg Thr Arg Glu Thr Ala Thr
     50                  55                  60

Ser Glu Arg Asn Ala Ser Glu Val Arg Asp Ala Thr Leu Asn Asn Ile
 65                  70                  75                  80

Phe Arg Phe Asp Ser Ile Gln Arg Glu Thr Leu Leu Pro Thr Asn Asn
                 85                  90                  95

Gly Gln Pro Leu Asn Gln Asn Phe Ser Leu Thr Phe Gln Pro Gln Gln
             100                 105                 110

Gln Thr Asn Ala Leu Asn Gly Ile Asp Ile Asn Thr Val Asn Thr Asn
         115                 120                 125

Leu Met Asn Gly Val Asn Val Gln Ile Asp Gln Leu Asn Arg Leu Leu
 130                 135                 140

Pro Asn Leu Pro Glu Glu Arg Lys Gln Ile His Glu Phe Lys Leu
145                 150                 155                 160

Ile Val Gly Lys Lys Ile Gln Glu Phe Leu Val Val Ile Glu Lys Arg
                 165                 170                 175

Arg Lys Lys Ile Leu Asn Glu Ile Glu Leu Asp Asn Leu Lys Leu Lys
             180                 185                 190

Glu Leu Arg Ile Asp Asn Ser Pro Gln Ala Ile Ser Tyr Leu His Lys
         195                 200                 205

Leu Gln Arg Met Arg Leu Arg Ala Leu Glu Thr Glu Asn Met Glu Ile
 210                 215                 220

Arg Asn Leu Arg Leu Lys Ile Leu Thr Ile Ile Glu Glu Tyr Lys Lys
225                 230                 235                 240

Ser Leu Tyr Ala Tyr Cys His Ser Lys Leu Arg Gly Gln Gln Val Glu
                 245                 250                 255

Asn Pro Thr Asp Asn Phe Ile Ile Trp Ile Asn Ser Ile Asp Thr Thr
             260                 265                 270

Glu Ser Ser Asp Leu Lys Glu Gly Leu Gln Asp Leu Ser Arg Tyr Ser
         275                 280                 285

Arg Gln Phe Ile Asn Asn Val Leu Ser Asn Pro Ser Asn Gln Asn Ile
 290                 295                 300

Cys Thr Ser Val Thr Arg Arg Ser Pro Val Phe Ala Leu Asn Met Leu
305                 310                 315                 320

Pro Ser Glu Ile Leu His Leu Ile Leu Asp Lys Leu Asn Gln Lys Tyr
                 325                 330                 335

Asp Ile Val Lys Phe Leu Thr Val Ser Lys Leu Trp Ala Glu Ile Ile
             340                 345                 350

Val Lys Ile Leu Tyr Tyr Arg Pro His Ile Asn Lys Lys Ser Gln Leu
         355                 360                 365

Asp Leu Phe Leu Arg Thr Met Lys Leu Thr Ser Glu Glu Thr Val Phe
 370                 375                 380

Asn Tyr Arg Leu Met Ile Lys Arg Leu Asn Phe Ser Phe Val Gly Asp
385                 390                 395                 400

Tyr Met His Asp Thr Glu Leu Asn Tyr Phe Val Gly Cys Lys Asn Leu
                 405                 410                 415

Glu Arg Leu Thr Leu Val Phe Cys Lys His Ile Thr Ser Val Pro Ile
             420                 425                 430

Ser Ala Val Leu Arg Gly Cys Lys Phe Leu Gln Ser Val Asp Ile Thr
         435                 440                 445
```

-continued

```
Gly Ile Arg Asp Val Ser Asp Val Phe Asp Thr Leu Ala Thr Tyr
    450                 455                 460
Cys Pro Arg Val Gln Gly Phe Tyr Val Pro Gln Ala Arg Asn Val Thr
465                 470                 475                 480
Phe Asp Ser Leu Arg Asn Phe Ile Val His Ser Pro Met Leu Lys Arg
                485                 490                 495
Ile Lys Ile Thr Ala Asn Asn Met Asn Asp Glu Leu Val Glu Leu
            500                 505                 510
Leu Ala Asn Lys Cys Pro Leu Leu Val Glu Val Asp Ile Thr Leu Ser
            515                 520                 525
Pro Asn Val Thr Asp Ser Ser Leu Leu Lys Leu Leu Thr Arg Leu Val
        530                 535                 540
Gln Leu Arg Glu Phe Arg Ile Thr His Asn Thr Asn Ile Thr Asp Asn
545                 550                 555                 560
Leu Phe Gln Glu Leu Ser Lys Val Val Asp Asp Met Pro Ser Leu Arg
                565                 570                 575
Leu Ile Asp Leu Ser Gly Cys Glu Asn Ile Thr Asp Lys Thr Ile Glu
            580                 585                 590
Ser Ile Val Asn Leu Ala Pro Lys Leu Arg Asn Val Phe Leu Gly Lys
        595                 600                 605
Cys Ser Arg Ile Thr Asp Ala Ser Leu Phe Gln Leu Ser Lys Leu Gly
610                 615                 620
Lys Asn Leu Gln Thr Val His Phe Gly His Cys Phe Asn Ile Thr Asp
625                 630                 635                 640
Asn Gly Val Arg Ala Leu Phe His Ser Cys Thr Arg Ile Gln Tyr Val
                645                 650                 655
Asp Phe Ala Cys Cys Thr Asn Leu Thr Asn Arg Thr Leu Tyr Glu Leu
            660                 665                 670
Ala Asp Leu Pro Lys Leu Lys Arg Ile Gly Leu Val Lys Cys Thr Gln
        675                 680                 685
Met Thr Asp Glu Gly Leu Leu Asn Met Val Ser Leu Arg Gly Arg Asn
690                 695                 700
Asp Thr Leu Glu Arg Val His Leu Ser Tyr Cys Ser Asn Leu Thr Ile
705                 710                 715                 720
Tyr Pro Ile Tyr Glu Leu Leu Met Ser Cys Pro Arg Leu Ser His Leu
                725                 730                 735
Ser Leu Thr Ala Val Pro Ser Phe Leu Arg Pro Asp Ile Thr Met Tyr
            740                 745                 750
Cys Arg Pro Ala Pro Ser Asp Phe Ser Glu Asn Gln Arg Gln Ile Phe
        755                 760                 765
Cys Val Phe Ser Gly Lys Gly Val His Lys Leu Arg His Tyr Leu Val
770                 775                 780
Asn Leu Thr Ser Pro Ala Phe Gly Pro His Val Asp Val Asn Asp Val
785                 790                 795                 800
Leu Thr Lys Tyr Ile Arg Ser Lys Asn Leu Ile Phe Asn Gly Glu Thr
                805                 810                 815
Leu Glu Asp Ala Leu Arg Arg Ile Ile Thr Asp Leu Asn Gln Asp Ser
            820                 825                 830
Ala Ala Ile Ile Ala Ala Thr Gly Leu Asn Gln Ile Asn Gly Leu Asn
        835                 840                 845
Asn Asp Phe Leu Phe Gln Asn Ile Asn Phe Glu Arg Ile Asp Glu Val
850                 855                 860
Phe Ser Trp Tyr Leu Asn Thr Phe Asp Gly Ile Arg Met Ser Ser Glu
```

```
                865                 870                 875                 880
Glu Val Asn Ser Leu Leu Gln Val Asn Lys Thr Phe Cys Glu Asp
                    885                 890                 895
Pro Phe Ser Asp Val Asp Asp Gln Asp Tyr Val Val Ala Pro Gly
            900                 905                 910
Val Asn Arg Glu Ile Asn Ser Glu Met Cys His Ile Val Arg Lys Phe
        915                 920                 925
His Glu Leu Asn Asp His Ile Asp Asp Phe Glu Val Asn Val Ala Ser
    930                 935                 940
Leu Val Arg Val Gln Phe Gln Phe Thr Gly Phe Leu Leu His Glu Met
945                 950                 955                 960
Thr Gln Thr Tyr Met Gln Met Ile Glu Leu Asn Arg Gln Ile Cys Leu
                965                 970                 975
Val Gln Lys Thr Val Gln Glu Ser Gly Asn Ile Asp Tyr Gln Lys Gly
            980                 985                 990
Leu Leu Ile Trp Arg Leu Leu Phe Ile Asp Lys Phe Ile Met Val Val
        995                 1000                1005
Gln Lys Tyr Lys Leu Ser Thr Val Val Leu Arg Leu Tyr Leu Lys Asp
    1010                1015                1020
Asn Ile Thr Leu Leu Thr Arg Gln Arg Glu Leu Leu Ile Ala His Gln
1025                1030                1035                1040
Arg Ser Ala Trp Asn Asn Asn Asp Asn Asp Ala Asn Arg Asn Ala
                1045                1050                1055
Asn Asn Ile Val Asn Ile Val Ser Asp Ala Gly Ala Asn Asp Thr Ser
            1060                1065                1070
Asn Asn Glu Thr Asn Asn Gly Asn Asp Asp Asn Glu Thr Glu Asn Pro
        1075                1080                1085
Asn Phe Trp Arg Gln Phe Gly Asn Arg Met Gln Ile Ser Pro Asp Gln
    1090                1095                1100
Met Arg Asn Leu Gln Met Gly Leu Arg Asn Gln Asn Met Val Arg Asn
1105                1110                1115                1120
Asn Asn Asn Asn Thr Ile Asp Glu Ser Met Pro Asp Thr Ala Ile Asp
                1125                1130                1135
Ser Gln Met Asp Glu Ala Ser Gly Thr Pro Asp Glu Asp Met Leu
            1140                1145                1150

<210> SEQ ID NO 32
<211> LENGTH: 22
<212> TYPE: PRT
<213> ORGANISM: Saccharomyces cerevisiae

<400> SEQUENCE: 32

Ile Leu Ser Pro Thr Met Tyr Met Glu Val Tyr Thr Ala Ile Tyr Asn
  1               5                   10                  15

Tyr Cys Val Asn Lys Ser
                20

<210> SEQ ID NO 33
<211> LENGTH: 22
<212> TYPE: PRT
<213> ORGANISM: Saccharomyces cerevisiae

<400> SEQUENCE: 33

Asn Met Ala Pro Lys Asp Tyr Met Thr Leu Tyr Thr Ser Val Tyr Asp
  1               5                   10                  15

Tyr Cys Thr Ser Ile Thr
```

20

<210> SEQ ID NO 34
<211> LENGTH: 22
<212> TYPE: PRT
<213> ORGANISM: Saccharomyces cerevisiae

<400> SEQUENCE: 34

His Met Ser Lys Lys Tyr Tyr Met Met Leu Tyr Asp Ala Val Tyr Asn
 1               5                  10                  15

Ile Cys Thr Thr Thr Thr
            20

<210> SEQ ID NO 35
<211> LENGTH: 22
<212> TYPE: PRT
<213> ORGANISM: Saccharomyces cerevisiae

<400> SEQUENCE: 35

Ser Leu Thr Arg Ser Gln Tyr Met Arg Phe Tyr Thr His Val Tyr Asp
 1               5                  10                  15

Tyr Cys Thr Ser Val Ser
            20

<210> SEQ ID NO 36
<211> LENGTH: 22
<212> TYPE: PRT
<213> ORGANISM: Saccharomyces cerevisiae

<400> SEQUENCE: 36

Ser Met Ala Lys Ser Arg Tyr Met Glu Leu Tyr Thr His Val Tyr Asn
 1               5                  10                  15

Tyr Cys Thr Ser Val His
            20

<210> SEQ ID NO 37
<211> LENGTH: 22
<212> TYPE: PRT
<213> ORGANISM: Saccharomyces cerevisiae

<400> SEQUENCE: 37

Ala Phe Asp Ser Glu Gln Tyr Met Met Leu Tyr Thr Thr Ile Tyr Asn
 1               5                  10                  15

Met Cys Thr Gln Lys Pro
            20

<210> SEQ ID NO 38
<211> LENGTH: 22
<212> TYPE: PRT
<213> ORGANISM: Saccharomyces cerevisiae

<400> SEQUENCE: 38

Gly Met Thr Ile Thr Lys Tyr Met Glu Leu Tyr Thr Ala Ile His Asn
 1               5                  10                  15

Tyr Cys Ala Asp Ala Ser
            20

<210> SEQ ID NO 39
<211> LENGTH: 22
<212> TYPE: PRT
<213> ORGANISM: Saccharomyces cerevisiae

<400> SEQUENCE: 39

```
Leu Gly Leu Lys Thr Gly Tyr Gln Glu Leu Tyr Ser Gly Val Glu Asn
 1               5                  10                  15

Leu Thr Arg Ala Asp Gln
            20

<210> SEQ ID NO 40
<211> LENGTH: 22
<212> TYPE: PRT
<213> ORGANISM: Saccharomyces cerevisiae

<400> SEQUENCE: 40

Pro Ile Thr Asn Val Gln Trp His His Lys Phe Ser Asp Val Tyr Asp
 1               5                  10                  15

Ile Cys Val Ser Ile Pro
            20

<210> SEQ ID NO 41
<211> LENGTH: 22
<212> TYPE: PRT
<213> ORGANISM: Saccharomyces cerevisiae

<400> SEQUENCE: 41

Tyr Val Glu Arg Ala Thr Trp Asn Asp Arg Phe Ser Asp Ile Tyr Ala
 1               5                  10                  15

Leu Cys Val Ala Tyr Pro
            20

<210> SEQ ID NO 42
<211> LENGTH: 22
<212> TYPE: PRT
<213> ORGANISM: Saccharomyces cerevisiae

<400> SEQUENCE: 42

Gln Tyr Val Thr Gln Thr Trp Glu Leu Leu Lys Arg Ala Ile Gln Glu
 1               5                  10                  15

Ile Gln Arg Lys Asn Asn
            20

<210> SEQ ID NO 43
<211> LENGTH: 22
<212> TYPE: PRT
<213> ORGANISM: Saccharomyces cerevisiae

<400> SEQUENCE: 43

Gly Ser Val Gly Arg Asp Trp Ala Val Leu Ser Asp Asn Val Phe Ala
 1               5                  10                  15

Ile Leu Glu Asp Arg Lys
            20

<210> SEQ ID NO 44
<211> LENGTH: 22
<212> TYPE: PRT
<213> ORGANISM: Saccharomyces cerevisiae

<400> SEQUENCE: 44

Ser Val Thr Pro Ala Ala Trp Gln Asp Leu Phe Tyr His Val Tyr Lys
 1               5                  10                  15

Ile Thr Ser Trp Val Asp
            20

<210> SEQ ID NO 45
```

```
<211> LENGTH: 22
<212> TYPE: PRT
<213> ORGANISM: Saccharomyces cerevisiae

<400> SEQUENCE: 45

Ser Val Thr Lys Gln Gln Trp Phe Asp Leu Phe Ser Asp Val His Ala
 1               5                  10                  15

Val Cys Leu Trp Asp Asp
            20

<210> SEQ ID NO 46
<211> LENGTH: 21
<212> TYPE: PRT
<213> ORGANISM: Saccharomyces cerevisiae

<400> SEQUENCE: 46

Thr Ser Gln Leu Ser Phe Glu Glu Leu Tyr Arg Asn Ala Tyr Ile Leu
 1               5                  10                  15

Val Leu His Lys Tyr
            20

<210> SEQ ID NO 47
<211> LENGTH: 21
<212> TYPE: PRT
<213> ORGANISM: Saccharomyces cerevisiae

<400> SEQUENCE: 47

Met Ala Asp Leu Ser Phe Glu Gln Val Tyr Lys Thr Ile Tyr Thr Ile
 1               5                  10                  15

Val Leu Asn Lys Lys
            20

<210> SEQ ID NO 48
<211> LENGTH: 14
<212> TYPE: PRT
<213> ORGANISM: Saccharomyces cerevisiae
<220> FEATURE:
<221> NAME/KEY: UNSURE
<222> LOCATION: (1)
<223> OTHER INFORMATION: Xaa = one to ten amino acids
<221> NAME/KEY: UNSURE
<222> LOCATION: (4)
<223> OTHER INFORMATION: Xaa = Met, Arg, Thr or Glu
<221> NAME/KEY: UNSURE
<222> LOCATION: (5)
<223> OTHER INFORMATION: Xaa = Leu, Phe or Val
<221> NAME/KEY: UNSURE
<222> LOCATION: (7)
<223> OTHER INFORMATION: Xaa = Asp or Thr
<221> NAME/KEY: UNSURE
<222> LOCATION: (8)
<223> OTHER INFORMATION: Xaa = Ala, Ser, His or Thr
<221> NAME/KEY: UNSURE
<222> LOCATION: (9)
<223> OTHER INFORMATION: Xaa = Ile or Val
<221> NAME/KEY: UNSURE
<222> LOCATION: (11)
<223> OTHER INFORMATION: Xaa = Asn or Asp
<221> NAME/KEY: UNSURE
<222> LOCATION: (12)
<223> OTHER INFORMATION: Xaa = Tyr, Ile or Met
<221> NAME/KEY: UNSURE
<222> LOCATION: (14)
<223> OTHER INFORMATION: Xaa = Thr, Val or Ala

<400> SEQUENCE: 48

Xaa Tyr Met Xaa Xaa Tyr Xaa Xaa Xaa Tyr Xaa Xaa Cys Xaa
 1               5                  10
```

```
<210> SEQ ID NO 49
<211> LENGTH: 19
<212> TYPE: PRT
<213> ORGANISM: Saccharomyces cerevisiae
<220> FEATURE:
<221> NAME/KEY: UNSURE
<222> LOCATION: (1)
<223> OTHER INFORMATION: Xaa = Ile, Asn, His, Ser or Ala
<221> NAME/KEY: UNSURE
<222> LOCATION: (2)
<223> OTHER INFORMATION: Xaa = Leu, Met or Phe
<221> NAME/KEY: UNSURE
<222> LOCATION: (3)
<223> OTHER INFORMATION: Xaa = Ser, Ala, Thr or Asp
<221> NAME/KEY: UNSURE
<222> LOCATION: (4)
<223> OTHER INFORMATION: Xaa = Pro, Lys, Arg or Ser
<221> NAME/KEY: UNSURE
<222> LOCATION: (5)
<223> OTHER INFORMATION: Xaa = Thr, Lys, Ser or Glu
<221> NAME/KEY: UNSURE
<222> LOCATION: (6)
<223> OTHER INFORMATION: Xaa = Met, Asp, Tyr, Gln or Arg
<221> NAME/KEY: UNSURE
<222> LOCATION: (9)
<223> OTHER INFORMATION: Xaa = Met, Arg, Thr or Glu
<221> NAME/KEY: UNSURE
<222> LOCATION: (10)
<223> OTHER INFORMATION: Xaa = Leu, Phe or Val
<221> NAME/KEY: UNSURE
<222> LOCATION: (12)
<223> OTHER INFORMATION: Xaa = Asp or Thr
<221> NAME/KEY: UNSURE
<222> LOCATION: (13)
<223> OTHER INFORMATION: Xaa = Ala, Ser, His or Thr
<221> NAME/KEY: UNSURE
<222> LOCATION: (14)
<223> OTHER INFORMATION: Xaa = Ile or Val
<221> NAME/KEY: UNSURE
<222> LOCATION: (16)
<223> OTHER INFORMATION: Xaa = Asn or Asp
<221> NAME/KEY: UNSURE
<222> LOCATION: (17)
<223> OTHER INFORMATION: Xaa = Tyr, Ile or Met
<221> NAME/KEY: UNSURE
<222> LOCATION: (19)
<223> OTHER INFORMATION: Xaa = Thr, Val or Ala

<400> SEQUENCE: 49

Xaa Xaa Xaa Xaa Xaa Xaa Tyr Met Xaa Xaa Tyr Xaa Xaa Xaa Tyr Xaa
 1               5                  10                  15

Xaa Cys Xaa

<210> SEQ ID NO 50
<211> LENGTH: 9
<212> TYPE: PRT
<213> ORGANISM: Saccharomyces cerevisiae
<220> FEATURE:
<221> NAME/KEY: UNSURE
<222> LOCATION: (3)
<223> OTHER INFORMATION: Xaa = Met Arg Thr or Glu
<221> NAME/KEY: UNSURE
<222> LOCATION: (4)
<223> OTHER INFORMATION: Xaa = Leu Phe or Val
<221> NAME/KEY: UNSURE
<222> LOCATION: (6)
<223> OTHER INFORMATION: Xaa = Asp or Thr
<221> NAME/KEY: UNSURE
```

```
<222> LOCATION: (7)
<223> OTHER INFORMATION: Xaa = Ala Ser His or Thr
<221> NAME/KEY: UNSURE
<222> LOCATION: (8)
<223> OTHER INFORMATION: Xaa = Ile or Val

<400> SEQUENCE: 50

Tyr Met Xaa Xaa Tyr Xaa Xaa Xaa Tyr
 1               5
```

US 6,426,205 B1

METHODS AND COMPOSITIONS FOR MODULATING UBIQUITIN DEPENDENT PROTEOLYSIS

This application claims the benefit of U.S. Provisional application No. 60/063,254 filed Oct. 24, 1997 and U.S. Provisional application No. 60/092,443 filed Jul. 10, 1998.

FIELD OF THE INVENTION

The invention relates to methods and compositions for modulating ubiquitin dependent proteolysis.

BACKGROUND OF THE INVENTION

Ubiquitin-dependent proteolysis is a key regulatory mechanism that controls diverse cellular processes (reviewed in Hochstrasser 1996). In this pathway, ubiquitin is transferred via transthioesterification along a cascade of carrier enzymes, E1→E2→E3, and ultimately conjugated in an isopeptide linkage to a lysine residue of a substrate protein. Reiteration of the ubiquitin transferase reaction results in formation of a polyubiquitin chain on the substrate, which is then recognized by the 26S proteasome, and rapidly degraded. Specificity in protein ubiquitination derives from E3 enzymes, also known as ubiquitin-ligases (Hershko et al. 1983). In some cases, an E3 facilitates recognition of the target protein by an E2, while in others an E3 accepts a ubiquitin thioester from an E2 and directly transfers ubiquitin to the substrate (Scheffner et al. 1995). Although substrate recognition is a key aspect of ubiquitin dependent proteolysis, the identification of E3 enzymes has been problematic because the few known E3 families bear no sequence relationship to each other.

Ubiquitin-dependent proteolysis is essential for two major cell cycle transitions, the G1 to S phase transition and the metaphase to anaphase transition (reviewed in King et al. 1996). These transitions mediate alteration between states of high and low cyclin-dependent kinase (Cdk) activity, which in turn ensures that DNA replication origins fire only once per cell cycle and that chromosome segregation follows DNA replication (reviewed in Nasmyth 1996). Key targets of the ubiquitin proteolytic pathway at these transitions include positive regulators of Cdks, the cyclins, and negative regulators of Cdks, the Cdk inhibitors. In budding yeast, a single Cdk, Cdc28 (or Cdk1) is activated in G1 phase by the G1 cyclins Cln1–Cln3, and in S through M phase by the mitotic cyclins, Clb1–Clb6 (reviewed in Nasmyth, 1996). A motif called the destruction box targets mitotic cyclins and other proteins to a cell cycle-regulated E3 ubiquitin-ligase called the Anaphase Promoting Complex (APC) or cyclosome (reviewed in King et al. 1996). In contrast, phosphorylation targets G1 cyclins and Cdk inhibitors for degradation via a constitutive ubiquitination pathway (reviewed in Deshaies, 1997). Genetic analysis in budding yeast has revealed several components of this pathway: Cdc4, a WD40 repeat protein (Yochem and Byers, 1987), Cdc34, an E2 ubiquitin conjugating enzyme (Goebl et al. 1988), Cdc53 a protein that forms a tight complex with phosphorylated Clns (Willems et al. 1996), Grr1, a leucine rich repeat protein (Flick and Johnston, 1981), and Skp1, a protein that binds to a motif called the F-box (Bai et al. 1996). The F-box motif occurs in Cdc4, Grr1 and several other yeast and mammalian proteins (Bai et al. 1996). Cells lacking functional Cdc4, Cdc34, Cdc53 or Skp1 arrest in G1 because the Cdk inhibitor Sic1 is not degraded, which prevents the onset of Clb-Cdc28 activity and initiation of DNA replication (Nugroho and Mendenhall 1994; Schwob et al. 1994; Bai et al. 1996). In late G1 phase, Sic1 is phosphorylated by the Cln-Cdc28 kinases and thus targeted for ubiquitin dependent proteolysis (Schwob et al. 1994; Schneider et al. 1996; Tyers 1996). Recently, a requirement for Cdc4, Cdc34 and Cln2-Cdc28 activity in Sic1 ubiquitination has been demonstrated in an in vitro yeast extract system (Verma et al. 1997). Cdc34, Cdc53 and Skp1 are also required for Cln degradation (reviewed in Deshaies 1997), as is Grr1 (Barral at al. 1995), although this protein was originally identified because of its role in glucose repression (Flick and Johnston 1991).

Other important regulatory proteins are degraded via the Cdc34 pathway, including the Cln-Cdc28 inhibitor Far1 (McKinney et al. 1993; Henchoz et al. 1997), the replication protein Cdc6 (Piatti et al. 1996), and the transcription factor Gcn4 (Kornitzer et al. 1994). Aside from its G1 function, Skp1 also plays a role in G2 because certain conditional alleles of SKP1 arrest cells in G2, and because Skp1 is a component of the Cbf3 kinetochore complex (Bai et al. 1996; Connelly and Hieter 1996; Stemmann and Lechner 1996).

Genetic and biochemical evidence indicates that Cdc53 interacts with Cdc4 and Cdc34 (Willems et al. 1996; Mathias et al. 1996), and that the F-box of Cdc4 binds Skp1 (Bai et al. 1996). These interactions, and the fact that Cdc53 physically associates with phosphorylated forms of Cln2, suggest that Cdc4, Cdc34, Cdc53 and Skp1 may participate in an E2/E3 ubiquitination complex that recognizes and ubiquitinates phosphorylated substrates (Bai et al. 1996; Willems et al. 1996). Divergence of the Sic1 and Cln degradation pathways apparently occurs at the level of the two F-box proteins. Cdc4 is required for degradation of Sic1 (Schwob et al. 1994), whereas Grr1 is required for Cln1/2 degradation (Barral et al. 1995). It was therefore hypothesized that distinct F-box proteins recruit specific substrates to an E3 ubiquitin-ligase complex that contains Skp1 (Bai et al. 1996). The existence of a complex in vivo containing F-box proteins and Cdc34, Cdc53 and Skp1 has yet to be demonstrated.

SUMMARY OF THE INVENTION

Through analysis of Cdc53-interacting proteins the present inventors determined that Cdc53 forms complexes with Skp1, Cdc34, and each of the F-box proteins Cdc4, Grr1 and Met30 in vivo. Each F-box protein confers functional specificity on a core Cdc34-Cdc53-Skp1 complex for Sic1 degradation, Cln degradation and methionine biosynthesis gene regulation, respectively. The present inventors showed that Cdc53 is a scaffold that tethers Skp1/F-box proteins to Cdc34 within an E2/E3 ubiquintination complex. The present inventors have also identified a specific region on Cdc53 that binds to Skp1.

Broadly stated the present invention relates to (a) a complex comprising an E2 ubiquitin conjugating enzyme, a protein of the Cullin family, an F-box binding protein, and optionally a protein containing an F-box motif; and (b) a complex comprising a protein of the Cullin family and a protein containing an F-box motif. The invention is also directed to (a) a peptide derived from the binding domain of an E2 ubiquitin conjugating enzyme that interacts with a protein of the Cullin family; (b) a peptide derived from the binding domain of a protein of the Cullin family that interacts with an E2 ubiquitin conjugating enzyme; (c) a peptide derived from the binding domain of a protein of the Cullin family that interacts with an F-box binding protein; preferably a peptide of the formula I or Ia or (d) a peptide derived from the binding domain of an F-box binding protein that interacts with a protein of the Cullin family. The invention also contemplates antibodies specific for the complexes and peptides of the invention.

The present invention also provides a method of modulating ubiquitin dependent proteolysis comprising administering an effective amount of one or more of the following: (a) a complex comprising an E2 ubiquitin conjugating enzyme, a protein of the Cullin family, an F-box binding protein, and optionally a protein containing an F-box motif; (b) a complex comprising a protein of the Cullin family and a protein containing an F-box motif; (c) a peptide derived from the binding domain of an E2 ubiquitin conjugating enzyme that interacts with a protein of the Cullin family; (d) a peptide derived from the binding domain of a protein of the Cullin family that interacts with an E2 ubiquitin conjugating enzyme; (d) a peptide derived from the binding domain of a protein of the Cullin family that interacts with an F-box binding protein; preferably a peptide of the formula I or Ia (e) a peptide derived from the binding domain of an F-box binding protein that interacts with a protein of the Cullin family; or (f) enhancers or inhibitors of the interaction of an E2 ubiquitin conjugating enzyme or an F-box binding protein, with a protein of the Cullin family.

In a preferred embodiment of the invention a method is provided for modulating ubiquitin dependent proteolysis comprising administering an effective amount of one or more of the following: (a) a complex comprising Cdc34-Cdc53-Skp1; (b) a complex comprising Cdc34-Cdc53-Ckp1-protein containing an F-box motif; (c) a complex comprising Cdc53-protein containing an F-box motif; (d) a peptide comprising the binding domain of Cdc34 that interacts with Cdc53 or the binding domain of Cdc53 that interacts with Cdc34; (e) a peptide comprising the binding domain of Cdc53 that interacts with Skp1 or the binding domain of Skp1 that interacts with Cdc53; or, (f) inhibitors or enhancers of the interaction of Cdc34 or Skp1, with Cdc53.

The invention still further provides a method for identifying a substance that binds to a complex comprising an E2 ubiquitin conjugating enzyme and a protein of the Cullin family, a complex comprising an E2 ubiquitin conjugating enzyme, a protein of the Cullin family, an F-box binding protein, and optionally a protein containing an F-box motif, or a complex comprising a protein of the Cullin family and an F-box binding protein, comprising: (a) reacting the complex with at least one substance which potentially can bind with the interacting molecules in the complex, under conditions which permit the formation of conjugates between the substance and complex and (b) assaying for conjugates, for free substance, or for non-conjugated complexes. The invention also contemplates methods for identifying substances that bind to other intracellular proteins that interact with the complexes of the invention.

Still further the invention provides a method for evaluating a compound for its ability to modulate ubiquitin dependent proteolysis. For example a substance which inhibits or enhances the interaction of the molecules in a complex of the invention, or a substance which binds to the molecules in a complex of the invention may be evaluated. In an embodiment, the method comprises providing a known concentration of a complex of the invention, with a substance which binds to the complex, and a test compound under conditions which permit the formation of conjugates between the substance and complex, and removing and/or detecting conjugates.

The present invention also contemplates a peptide of the formula I which interferes with the interaction of Cdc53 and Skp1.

$X^1$-Tyr-Met-$X^2$-$X^3$-Tyr-$X^4$-$X^5$-$X^6$-Ty-$X^7$-$X^8$-Cys-$X^9$ (SEQ ID NO: 48)

wherein $X^1$ represents one to ten amino acids, $X^2$ represents Met, Arg, Thr, or Glu, $X^3$ represents Leu, Phe, or Val, $X^4$ represents Asp or Thr, $X^5$ represents Ala, Ser, His, or Thr, $X^6$ represents Ile or Val, $X^7$ represents Asn or Asp, $X^8$ represents Tyr, Ile, or Met, and $X^9$ represents Thr, Val, or Ala.

In an embodiment of the present invention a peptide of the formula Ia which interferes with the interaction of Cdc53 and Skp1 is provided:

$X^1$-$X^2$-$X^3$-$X^4$-$X^5$-$X^6$-Tyr-Met-$X^7$-$X^8$-Tyr-$X^9$$X^{10}$-$X^{11}$-Tyr-$X^{12}$-$X^{13}$-Cys-$X^{14}$ (SEQ ID NO: 49)

wherein $X^1$ represents Ile, Asn, His, Ser, or Ala, $X^2$ represents Leu, Met or Phe, $X^3$ represents Ser, Ala, Thr, or Asp, $X^4$ represents Pro, Lys, Arg, or Ser, $X^5$ represents Thr, Lys, Ser, or Glu, $X^6$ represents Met, Asp, Tyr, Gln, or Arg, $X^7$ represents Met, Arg, Thr, or Glu, $X^8$ represents Leu, Phe, or Val, and $X^9$ represents Asp or Thr, $X^{10}$ represents Ala, Ser, His, or Thr, $X^{11}$ represents Ile or Val, $X^{12}$ represents Asn or Asp, $X^{13}$ represents Tyr, Ile, or Met, and $X^{14}$ represents Thr, Val or Ala.

The invention also relates to truncations and analogs of the peptides of the invention. The invention also relates to the use of a peptide of the formula I or Ia to interfere with the interaction of a protein of the Cullin family preferably Cdc53 and an F-box binding protein preferably Skp1; and, pharmaceutical compositions for inhibiting the interaction of a protein of the Cullin family preferably Cdc53 and an F-box binding protein preferably Skp1.

Further, the invention relates to a method of modulating the interaction of Cdc53 and Skp1 comprising changing the amino acid Tyr at position 48 and/or Met at position 49 in Cdc53.

The peptides and antibodies of the invention, and substances and compounds identified using the methods of the invention may be used to modulate ubiquitin dependent proteolysis, and they may be used to modulate cellular processes of cells (such as proliferation, growth, and/or differentiation, in particular glucose and methionine biosynthesis, gene expression, cell division, and transcription) in which the compounds or substances are introduced.

Accordingly, the antibodies, peptides, substances and compounds may be formulated into compositions for administration to individuals suffering from a proliferative or differentiative condition. Therefore, the present invention also relates to a composition comprising one or more of a peptide or antibody of the invention, or a substance or compound identified using the methods of the invention, and a pharmaceutically acceptable carrier, excipient or diluent. A method for modulating proliferation, growth, and/or differentiation of cells is also provided comprising introducing into the cells a peptide or antibody of the invention, a compound or substance identified using the methods of the invention or a composition containing same. Methods for treating proliferative and/or differentiative disorders using the compositions of the invention are also provided.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 7 shows the amino acid sequence of a Cdc34 protein (SEQ ID NOS: 22 and 23).

FIG. 8 shows the amino acid sequences of a Cdc53 protein (SEQ. ID NO: 24) and a Cul-2 protein (SEQ ID NO: 25).

FIG. 9 shows the amino acid sequence of a Skp1 protein (SEQ ID NO: 28).

FIG. 10 shows the amino acid sequences of a Cdc4 protein (SEQ ID NO: 29), a Met30 protein (SEQ ID NO: 30), and a Grr1 protein (SEQ ID NO: 31).

FIG. 11 shows that amino acids Y48 and M49 in Cdc53 are required for binding to Skp1. Wild type and Y48W, M49E mutants of Cdc53$^{MYC}$6 were immunoprecipitated and (A) western blotted for Cdc53$^{MYC6}$, Cdc53, and Skp1, and (B) silver stained. On the silver-stained gel, bands that exist in the wild type but not the mutant Cdc53 IP are marked with an open triangle (SEQ ID NOS: 32–47).

DETAILED DESCRIPTION OF THE INVENTION

Definitions

Figure 1A:
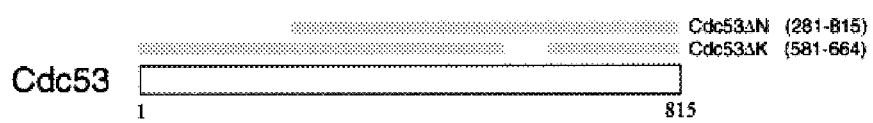
FIG. 1. Cdc53 two hybrid interactions. (A) Cdc53 two hybrid screens were carried out with three Cdc53 fusion proteins: Gal4$^{DBD}$-Cdc53, Gal4$^{DBD}$-Cdc53$^{\Delta N}$, and Gal4$^{DBD}$-Cdc53$^{\Delta K}$. (B) Interaction of isolates with Gal4$^{DBD}$-Cdc53 and Gal4$^{DBD}$-Cdc53$^{\Delta K}$ in a β-galactosidase filter assay. (C) Schematic of Cdc53 interacting proteins. (D) Two hybrid interactions of LexA$^{DBD}$-Met30 derivatives with VP16$^{AD}$-Skp1 Interactions quantitated by liquid β-galactosidase assay in Miller units.

Unless otherwise indicated, all terms used herein have the same meaning as they would to one skilled in the art of the present invention. Practitioners are particularly directed to Current Protocols in Molecular Biology (Ansubel) for definitions and terms of the art.

Abbreviations for amino acid residues are the standard 3-letter and/or 1-letter codes used in the art to refer to one of the 20 common L-amino acids. Likewise abbreviations for nucleic acids are the standard codes used in the art. "E2 ubiquitin conjugating enzyme" refers to one of the components involved in ubiquitin transfer reactions to form ubiquitin-protein conjugates which are recognized by the 26S proteasome. An example of an E2 ubiquitin conjugating enzyme is Cdc34, and homologs or portions thereof. (See FIG. 7 for a Cdc34 amino acid sequence.)

"Protein of the Cullin family" refers to the family of proteins involved in the regulation of cell division. The archetypal member of the family is Cdc53. The family also includes, homologs and portions of Cdc53, including the proteins regulating cell division in C. elegans and mammalian cells such as Cul-1, Cul-2, and the metazoan Cdc53 homologs described in Kipreos et al., 1996. (See FIG. 8 for sequences for Cdc53 and Cul-2).

"F-box binding protein" refers to proteins that bind to proteins containing an F-box motif. Examples of F-box binding proteins are Skp1 and Scon C and homologs, and portions, thereof. (See FIG. 9 for a Skp1 sequence.)

"Proteins containing an F-box motif" refers to proteins have a characteristic structural motif called the F-box as described in Bai et al, 1996. Examples of the proteins include Cdc4, Grr1, pop1, Met30, Scon2/Scon3, and several other yeast and mammalian proteins (Bai et al, 1996), and homologs or portions thereof. (See FIG. 10 for a Cdc4 sequence, a Met30 sequence, and a Grr1 sequence.)

A "binding domain" is that portion of the molecule in a complex of the invention (i.e. E2 ubiquitin conjugating enzyme, protein of the Cullin family, F-box binding protein, or protein containing an F-box motif) which interacts directly or indirectly with another molecule in a complex of the invention. The binding domain may be a sequential portion of the molecule i.e. a contiguous sequence of amino acids, or it may be conformational i.e. a combination of non-contiguous sequences of amino acids which when the molecule is in its native state forms a structure that interacts with another molecule in a complex of the invention.

By being "derived from" a binding domain is meant any molecular entity which is identical or substantially equivalent to the native binding domain of a molecule in a complex of the invention (i.e. E2 ubiquitin conjugating enzyme, protein of the Cullin family, F-box binding protein; or protein containing an F-box motif). A peptide derived from a specific binding domain may encompass the amino acid sequence of a naturally occurring, binding site, any portion of that binding site, or other molecular entity that functions to bind to an associated molecule. A peptide derived from such a binding domain will interact directly or indirectly with an associated molecule in such a way as to mimic the native binding domain. Such peptides may include competitive inhibitors, peptide mimetics, and the like.

The term "interacting" refers to a stable association between two molecules due to, for example, electrostatic, hydrophobic, ionic and/or hydrogen-bond interactions under physiological conditions. Certain interacting molecules interact only after one or more of them has been stimulated. For example, a protein containing an F-box motif may only bind to a substrate if the substrate is phosphorylated (eg. phosphorylated Sic1).

An enhancer or inhibitor of the interaction of an E2 ubiquitin conjugating enzyme or a F-box binding protein, and a protein of the Cullin family is intended to include a peptide or peptide fragment derived from the binding domain of an E2 ubiquitin conjugating enzyme, an F-box binding protein, or a protein of the Cullin family. The enhancer or inhibitor will not include the full length sequence of the wild-type molecule. Peptide mimetics, synthetic molecules with physical structures designed to mimic structural features of particular peptides, may serve as inhibitors or enhancers. Inhibitors or enhancers affect ubiquitin-dependent proteolysis. The enhancement or inhibition may be direct, or indirect, or by a competitive or non-competitive mechanism.

"Peptide mimetics" are structures which serve as substitutes for peptides in interactions between molecules (See Morgan et al (1989), Ann. Reports Med. Chem. 24:243–252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide, or enhancer or inhibitor of the invention.

Sequences are "homologous" or considered "homologs" when at least about 70% (preferably at least about 80 to 90%, and most preferably at least 95%) of the nucleotides or amino acids match over a defined length of the molecule. Substantially homologous also includes sequences showing identity to the specified sequence. Preferably, the amino acid or nucleic acid sequences have an alignment score of greater than 5 (in standard deviation units) using the program ALIGN with the mutation gap matrix and a gap penalty of 6 or greater (Dayhoff).

Peptides of the Invention

The invention provides peptide molecules which bind to and inhibit the interactions of the molecules in the complexes of the invention. The molecules are derived from the binding domain of an E2 ubiquitin conjugating enzyme, a protein of the Cullin family, an F-box binding protein; or a protein containing an F-box motif. For example, peptides of the invention include the following amino acids of Cdc53 (see FIG. 8): amino acids 448 to 748 (comprising the binding domain for Cdc34) (SEQ ID NO: 26) and amino acids 9 to 280 (comprising the binding domain for Skp1) (SEQ ID NO: 27), or portions thereof that bind to Cdc34 and Skp1. Other proteins containing these binding domain sequences may be identified with a protein homology search, for example by searching available databases such as. GenBank or SwissProt and various search algorithms and/or programs may be used including. FASTA, BLAST (available as a part of the GCG sequence analysis package, University of Wisconsin, Madison, Wis.), or ENTREZ (National Center for Biotechnology Information, National Library of Medicine, National Institutes of Health, Bethesda, Md.).

In accordance with an embodiment of the invention;-specific peptides are contemplated that mediate the binding of a protein of the Cullin family preferably Cdc53, and an F-box binding protein preferably Skp1.

Therefore, the invention relates to a peptide of the formula I which interferes with the interaction of Cdc53 and Skp1

$X^1$-Tyr-Met-$X^2$-$X^3$-Tyr-$X^4$-$X^5$-$X^6$-Tyr-$X^7$-$X^8$-Cys-$X^9$ (SEQ ID NO: 48)

wherein $X^1$ represents one to ten amino acids, $X^2$ represents Met, Arg, Thr, or Glu, $X^3$ represents Leu, Phe, or Val, $X^4$ represents Asp or Thr, $X^5$ represents Ala, Ser, His, or Thr, $X^6$ represents Ile or Val, $X^7$ represents Asn or Asp, $X^8$ represents Tyr, Ile, or Met, and $X^9$ represents Thr, Val, or Ala.

In an embodiment of the present invention a peptide of the formula Ia which interferes with the interaction of Cdc53 and Skp1 is provided:

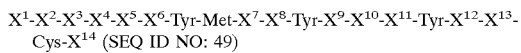
Cys-$X^{14}$ (SEQ ID NO: 49)

wherein $X^1$ represents Ile, Asn, His, Ser, or Ala, $X^2$ represents Leu, Met or Phe, $X^3$ represents Ser, Ala, Thr, or Asp, $X^4$ represents Pro, Lys, Arg, or Ser, $X^5$ represents Thr, Lys, Ser, or Glu, $X^6$ represents Met, Asp, Tyr, Gln, or Arg, $X^7$ represents Met, Arg, Thr, or Glu, $X^8$ represents Leu, Phe, or Val, and $X^9$ represents Asp or Thr, $X^{10}$ represents Ala, Ser, His, or Thr, $X^{11}$ represents Ile or Val, $X^{12}$ represents Asn or Asp, $X^{13}$ represents Tyr, Ile, or Met, and $X^{14}$ represents Thr, Val or Ala.

All of the peptides of the invention, as well as molecules substantially homologous, complementary or otherwise functionally or structurally equivalent to these peptides may be used for purposes of the present invention. In addition to full-length peptides of the invention, truncations of the peptides are contemplated in the present invention. Truncated peptides may comprise peptides on about 7 to 10 amino acid residues The truncated peptides may have an amino group (—NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated peptides may have a carboxyl group, an amido group, a T-butyloxycarbonyl group, or a macromolecule including but not limited to lipid-fatty acid conjugates, polyethylene glycol, or carbohydrates at the carboxy terminal end.

The peptides of the invention may also include analogs of a peptide of the invention, and/or truncations of the peptide, which may include, but are not limited to the peptide of the invention containing one or more amino acid insertions, additions, or deletions, or both. Analogs of the peptide of the invention exhibit the activity characteristic of the peptide e.g. interference with the interaction of Cdc53 with Skp1, and may further possess additional advantageous features such as increased bioavailability, stability, or reduced host immune recognition.

One or more amino acid insertions may be introduced into a peptide of the invention. Amino acid insertions may consist of a single amino acid residue or sequential amino acids.

One or more amino acids, preferably one to five amino acids, may be added to the right or left termini of a peptide of the invention. Deletions may consist of the removal of one or more amino acids, or discrete portions from the peptide sequence. The deleted amino acids may or may not be contiguous. The lower limit length of the resulting analog with a deletion mutation is about 7 amino acids.

It is anticipated that if amino acids are inserted or deleted in sequences outside the Tyr-Met-$X^1$-$X^3$-$X^4$-$X^5$-Tyr sequence (SEQ. ID. NO: 50) that the resulting analog of the peptide will exhibit the activity of a peptide of the invention.

Preferred peptides of the invention include the following: MEVTAIYNYCV (SEQ ID NO: 1), YMEVTAIYNY-CVNKS (SEQ ID NO: 2), ILSPTMYMEVYTAIYNY-CVNKS (SEQ ID NO: 3), YMTLYTSVYDYCT (SEQ ID NO: 4), YMTLYTSVYDYCTSIT (SEQ ID NO: 5), MAP-KDYMTLYTSVYDYCTSIT (SEQ ID NO: 6), YMMLY-DAVYNICT (SEQ ID NO: 7), YMMLYDAVYNICTTTT (SEQ ID NO: 8), HMSKKYYMMLYDAVYNICTTT (SEQ ID NO: 9), YMRFYTHVYDYCT (SEQ ID NO: 10), YMR-FYTHVYDYCTSVS (SEQ ID NO: 11), SLTRSQYMR-FYTHVYDYCTSVS (SEQ ID NO: 12), YMELYTH-VYNYCT (SEQ ID NO: 13), YMELYTHVYNYCTSVH (SEQ ID NO: 14), SMAKSRYMELYTHVYNYCTSVH (SEQ ID NO: 15), YMMLYTTIYNMCT (SEQ ID NO: 16), YMMLYTTIYNMCTQKP (SEQ ID NO: 17), AFDSE-QYMMLYTTIYNMCTQKP (SEQ ID NO: 18), YMELYTAIHNTCA (SEQ ID NO: 19), YMELYTAIHNTCADAS (SEQ ID NO: 20), and GMIT-FYMELYTAHTCADAS (SEQ ID NO: 21).

The invention also includes a peptide conjugated with a selected protein, or a selectable marker (see below) to produce fusion proteins.

The peptides of the invention may be prepared using recombinant DNA methods. Accordingly, nucleic acid molecules which encode a peptide of the invention may be incorporated in a known manner into an appropriate expression vector which ensures good expression of the peptide. Possible expression vectors include but are not limited to cosmids, plasmids, or modified viruses so long as the vector is compatible with the host cell used. The expression vectors contain a nucleic acid molecule encoding a peptide of the invention and the necessary regulatory sequences for the transcription and translation of the inserted protein-sequence. Suitable regulatory sequences may be obtained from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Other sequences, such as an origin of replication, additional DNA restriction sites, enhancers, and sequences conferring inducibility of transcription may also be incorporated into the expression vector.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

The recombinant expression vectors may also contain genes which encode a fusion portion which provides increased expression of the recombinant peptide; increased solubility of the recombinant peptide; and/or aid in the purification of the recombinant peptide by acting as a ligand in affinity purification. For example, a proteolytic cleavage site may be inserted in the recombinant peptide to allow separation of the recombinant peptide from the fusion portion after purification of the fusion protein. Examples of fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST, maltose E binding protein, or protein A, respectively, to the recombinant protein.

Recombinant expression vectors may be introduced into host cells to produce a transformant host cell. Transformant host cells include prokaryotic and eukaryotic cells which have been transformed or transfected with a recombinant expression vector of the invention. The terms "transformed with", "transfected with", "transformation" and "transfection" are intended to include the introduction of nucleic acid (e.g. a vector) into a cell by one of many techniques known in the art. For example, prokaryotic cells can be transformed with nucleic acid by electroporation or calcium-chloride mediated transformation. Nucleic acid can be introduced into mammalian cells using conventional techniques such as calcium phosphate or calcium chloride co-precipitation, DEAE-dextran-mediated transfection, lipofectin, electroporation or microinjection., Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the peptides of the invention may be expressed in bacterial cells such as E. coli, insect cells (using baculovirus), yeast cells or mammalian cells. Other suitable host cells can be found in Goeddel, Gene Expression Technology: Methods in Enzymology 185, Academic Press, San Diego, Calif. (1991).

The peptides of the invention may be tyrosine phosphorylated using the method described in Reedijk et al. (The EMBO Journal 11(4):1365, 1992). For example, tyrosine phosphorylation may be induced by infecting bacteria harbouring a plasmid containing a nucleotide sequence encoding a peptide of the invention, with a λgt11 bacteriophage encoding the cytoplasmic domain of the Elk tyrosine kinase as a LacZ-Elk fusion. Bacteria containing the plasmid and bacteriophage as a lysogen are isolated. Following induction of the lysogen, the expressed peptide becomes phosphorylated by the Elk tyrosine kinase.

The peptides of the invention may be synthesized by conventional techniques. For example, the peptides may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3–254 for solid phase synthesis techniques; and M Bodansky, Principles fo Peptide Synthesis, Springer-Verlag, Berlin 1984, and E. Gross and J. Meienhofer, Eds., The Peptides: Analysis, Synthesis, Biologu, suprs, Vol 1, for classical solution synthesis.) By way of example, the peptides may be synthesized using 9-fluorenyl methoxycarbonyl (Fmoc) solid phase chemistry with direct incorporation of phosphotyrosine as the N-fluorenylmethoxy-carbonyl-O-dimethyl phosphono-L-tyrosine derivative.

N-terminal or C-terminal fusion proteins comprising a peptide of the invention conjugated with other molecules may be prepared by fusing; through recombinant techniques, the N-terminal or C-terminal of the peptide, and the sequence of a selected protein or selectable marker with a desired biological function. The resultant fusion proteins contain the peptide fused to the selected protein or marker protein as described herein. Examples of proteins which may be used to prepare fusion proteins include immunoglobulins, glutathione-S-transferase (GST), hemagglutinin (HA), and truncated myc.

Cyclic derivatives of the peptides of the invention are also part of the present invention. Cyclization may allow the peptide to assume a more favorable conformation for association with molecules in complexes of the invention. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466–8467. The side chains of Tyr and Asn may be linked to form cyclic peptides. The components that form the bonds may be side chains of amino acids, non-amino acid components or a combination of the two. In an embodiment of the invention, cyclic peptides are contemplated that have a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amiino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides that interact with an E2 ubiquitin conjugating enzyme, a protein of the Cullin family, an F-box binding protein; or a protein containing an F-box motif may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

Peptides of the invention may be used to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds which can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison may be used to design compounds expected to possess desired activities.

The peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

The peptides of the invention may be used to prepare monoclonal or polyclonal antibodies. Conventional methods can be used to prepare the antibodies. As to the details relating to the preparation of monoclonal antibodies reference can be made to Goding, J. W., Monoclonal Antibodies: Principles and Practice, 2nd Ed., Academic Press, London, 1986. As discussed below. the antibodies may be used to identify proteins binding sites for Skp1.

The peptides and antibodies specific for the peptides of the invention may be labelled using conventional methods with various enzymes, fluorescent materials, luminescent materials and radioactive materials. Suitable enzymes, fluorescent materials, luminescent materials, and radioactive material are well known to the skilled artisan. Labeled antibodies specific for the peptides of the invention may be used to screen for proteins with Skp1 binding sites, and labeled peptides of the invention may be used to screen for Skp1 binding site containing proteins such as Cdc53.

Computer modelling techniques known in the art may also be used to observe the interaction of a peptide of the invention, and truncations and analogs thereof with a molecule in a complex of the invention e.g. Skp1 (for example, Homology Insight II and Discovery available from BioSym/ Molecular Simulations, San Diego, Calif., U.S.A.). If computer modelling indicates a strong interaction, the peptide can be synthesized and tested for its ability to interfere with the binding of Cdc53 and Skp1 as discussed above.

Complexes of the Invention

The complexes of the invention include the following: (a) a complex comprising an E2 ubiquitin conjugating enzyme, a protein of the Cullin family, and a F-box binding protein, and optionally a protein containing an F-box motif; and (b) a complex comprising a protein of the Cullin family and a protein containing an F-box motif. Complexes also containing molecules that bind to a protein containing an F-box motif (eg. Sic1, Cln, Met 4 or activated forms thereof) are also contemplated. It will be appreciated that the complexes may comprise only the binding domains of the interacting molecules and such other flanking sequences as are necessary to maintain the activity of the complexes.

The invention also contemplates antibodies specific for complexes of the invention. The antibodies may be intact monoclonal or polyclonal antibodies, and immunologically active fragments (e.g. a Fab or (Fab)$_2$ fragment), an antibody heavy chain, and antibody light chain, a genetically engineered single chain $F_V$ molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

Antibodies specific for the complexes of the invention may be used to detect the complexes in tissues and to determine their tissue distribution. In vitro and in situ detection methods using the antibodies of the invention may be used to assist in the prognostic and/or diagnostic evaluation of proliferative and/or differentiative disorders. Antibodies specific for the complexes of the invention may also be used therapeutically to decrease the degradation of proteins that interact with F-box containing proteins such as Sic1, Cln, and Met4.

The complexes of the invention play a central role in ubiquitin-dependent proteolysis and some genetic diseases may include mutations at the binding domain regions of the interacting molecules in the complexes of the invention. Therefore, if a complex of the invention is implicated in a genetic disorder, it may be possible to use PCR to amplify DNA from the binding domains to quickly check if a mutation is contained within one of the domains. Primers can be made corresponding to the flanking regions of the domains and standard sequencing methods can be employed to determine whether a mutation is present. This method does not require prior chromosome mapping of the affected gene and can save time by obviating sequencing the entire gene encoding a defective protein.

Methods for Identifying or Evaluating Substances/ Compounds

The methods described herein are designed to identify substances that modulate the activity of a complex of the invention thus affecting ubquitin dependent proteolysis. Novel substances are therefore contemplated that bind to molecules in the complexes, or bind to other proteins that interact with the molecules, to compounds that interfere with, or enhance the interaction of the molecules in a complex, or other proteins that interact with the molecules.

The substances and compounds identified using the methods of the invention include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], and small organic or inorganic molecules. The substance or compound may be an endogenous physiological compound or it may be a natural or synthetic compound.

Substances which modulate the activity of a complex of the invention can be identified based on their ability to bind to a molecule in the complex. Therefore, the invention also provides methods for identifying novel substances which bind molecules in the complex. Substances identified using the methods of the invention may be isolated, cloned and sequenced using conventional techniques.

Novel substances which can bind with a molecule in a complex of the invention may be identified by reacting one of the molecules with a test substance which potentially binds to the molecule, under conditions which permit the formation of substance-molecule conjugates and removing and/or detecting the conjugates. The conjugates can be detected by assaying for substance-molecule conjugates, for free substance, or for non-complexed molecules. Conditions which permit the formation of substance-molecule conjugates may be selected having regard to factors such as the nature and amounts of the substance and the molecule.

The substance-molecule conjugate, free substance or non-complexed molecules may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against the molecule or the substance, or labelled molecule, or a labelled substances may be utilized. The antibodies, proteins, or substances may be labelled with a detectable substance as described above.

A molecule, or complex of the invention, or the substance used in the method of the invention may be insolubilized. For example, a molecule, or substance may be bound to a suitable carrier such as agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized protein or substance may be prepared by reacting the material with a suitable insoluble carrier using known chemical or physical methods, for example, cyanogen bromide coupling.

The invention also contemplates a method for evaluating a compound for its ability to modulate the biological activity of a complex of the invention, by assaying for an agonist or antagonist (i.e. enhancer or inhibitor) of the binding of molecules in the complex. The basic method for evaluating if a compound is an agonist or antagonist of the binding of molecules in a complex of the invention, is to prepare a reaction mixture containing molecules and the substance under conditions which permit the formation of complexes, in the presence of a test compound. The test compound may be initially added to the mixture, or may be added subsequent to the addition of molecules. Control reaction mixtures without the test compound or with a placebo are also prepared. The formation of complexes is detected and the formation of complexes in the control reaction but not in the reaction mixture indicates that the test compound interferes with the interaction of the molecules. The reactions may be carried out in the liquid phase or the molecules, or test compound may be immobilized as described herein.

It will be understood that the agonists and antagonists i.e. inhibitors and enhancers that can be assayed using the methods of the invention may act on one or more of the binding sites on the interacting molecules in the complex including agonist binding sites, competitive antagonist binding sites, non-competitive antagonist binding sites or allosteric sites.

The invention also makes it possible to screen for antagonists that inhibit the effects of an agonist of the interaction of molecules in a complex of the invention. Thus, he invention may be used to assay for a compound that competes for the same binding ite of a molecule in a complex of the invention.

The invention also contemplates methods for identifying novel compounds that bind to proteins that interact with a molecule of a complex of the invention. Protein-protein interactions may be identified using conventional methods such as co-immunoprecipitation, crosslinking and co-purification through gradients or chromatographic columns. Methods may also be employed that result in the simultaneous identification of genes which encode proteins interacting with a molecule. These methods include probing expression libraries with labeled molecules. Additionally, x-ray crystallographic studies may be used as a means of evaluating interactions with substances and molecules. For example, purified recombinant molecules in a complex of the invention when crystallized in a suitable form are amenable to detection of intra-molecular interactions by x-ray crystallography. Spectroscopy may also be used to detect interactions and in particular, Q-TOF instrumentation may be used.

Two-hybrid systems may also be used to detect protein interactions in vivo. Generally, plasmids are constructed that encode two hybrid proteins. A first hybrid protein consists of the DNA-binding domain of a transcription activator protein fused to a molecule in a complex of the invention, and the second hybrid protein consists of the transcription activator protein's activator domain fused to an unknown protein encoded by a cDNA which has been recombined into the plasmid as part of a cDNA library. The plasmids are transformed into a strain of yeast (e.g,. *S. cerevisiae*) that contains a reporter gene (e.g. lacZ, luciferase, alkaline phosphatase, horseradish peroxidase) whose regulatory region contains the transcription activator's binding site. The hybrid proteins alone cannot activate the transcription of the reporter gene. However, interaction of the two hybrid proteins reconstitutes the functional activator protein and results in expression of the reporter gene, which is detected by an assay for the reporter gene product.

It will be appreciated that fusion proteins and recombinant fusion proteins may be used in the above-described methods. It will also be appreciated that the complexes of the invention may be reconstituted in vitro using recombinant molecules and the effect of a test substance may be evaluated in the reconstituted system.

The reagents suitable for applying the methods of the invention to evaluate substances and compounds that modulate ubiquitin dependent proteolysis may be packaged into convenient kits providing the necessary materials packaged into suitable containers. The kits may also include suitable supports useful in performing the methods of the invention.

Compositions and Treatments

The peptides of the invention, and substances and compounds identified using the methods of the invention may be used to modulate ubiquitin dependent proteolysis, and they may be used to modulate cellular processes such as proliferation, growth, and/or differentiation of cells in which the compounds or substances are introduced. Thus, the substances may be used for the treatment of proliferative disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, breast, ovarian, colon, hematopoietic cancers, head and neck cancers, and nervous system cancers, benign lesions such as papillomas, arthrosclerosis, angiogenesis, and viral infections, in particular HIV infections, psoriasis, bone diseases, fibroproliferative disorders such as involving connective tissue, atherosclerosis and other smooth muscle proliferative disorders, chronic inflammation, and arthropathies such as arthritis. In addition to proliferative disorders, the treatment of differentiative disorders which result from, for example, de-differentiation of tissue which may be accompanied by abnormal reentry into mitosis. Such degenerative disorders that may be treated using the peptides and compositions of the invention include neurodegenerative disorders such as chronic neurodegenerative diseases of the nervous system, including Alzheimer's disease, Parkinson's disease, Huntington's chorea, amylotrophic lateral sclerosis and the like, as well as spinocerebellar degeneration.

Accordingly, the peptides, substances, antibodies, and compounds may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions that may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances or compounds in association with one or more pharmaceutically acceptable vehicles or diluents, and contained in buffered solutions with a suitable pH and iso-osmotic with the physiological fluids.

The activity of the substances, compounds, antibodies, and compositions of the invention may be confirmed in animal experimental model systems.

The invention also provides methods for studying the function of a complex of the invention. Cells, tissues, and non-human animals lacking in the complexes or partially lacking in molecules in the complexes may be developed using recombinant expression vectors of the invention having specific deletion or insertion mutations in the molecules. A recombinant expression vector may be used to inactivate or alter the endogenous gene by homologous recombination, and thereby create complex deficient cells, tissues or animals. Null alleles may be generated in cells and may then be used to generate transgenic non-human animals.

The following non-limiting examples are illustrative of the present invention:

EXAMPLE 1

The following materials and methods were used in the investigations described in the example.

Methods

Plasmids

Plasmids were constructed using standard molecular cloning techniques (Table 1). For two hybrid screens, the CDC53 open reading frame was cloned into the BamHI site of pAS2 (provided by S. Elledge) to create a Gal4$^{DBD}$-Cdc53 fusion. Versions that lacked either the N-terminal 280 residues (Gal4$^{DBD}$-Cdc53$^{\Delta N}$) or internal residues 581–664 (Gal4$^{DBD}$-Cdc53$^{\Delta K}$) were created by digestion with NcoI or KpnI respectively and religating. Gal4$^{AD}$-Cdc4$^{\Delta 3WD}$ is derived from a truncated CDC4 PCR product (Skowyra et al., 1997) cloned into the BamHI site of pGAD424. To test the Skp1-Met30 interaction in the two hybrid system, a SKP1 fragment was cloned into the BamHI site of pVAD1, to create a VP16-Skp1 fusion. LexA-Met30 derivatives were based on pLEXM30-4 (Thomas et al. 1995). Met30 was tagged at the N-terminus with an HA epitope by insertion of a MET30 fragment encoding amino acids 7–640 from pLEXM30-4 into a pADH1-HA expression plasmid (Li and Johnston 1997). Cdc4 was tagged at the N-terminus with a FLAG epitope by site directed mutagenesis. A CDC53 deletion construct was made by replacing an internal BglII fragment of pGEM53-8 (Mathias et al. 1996) with an ADE2 fragment. To allow for negative selection of wild type CDC53 in the cdc53$^\Delta$ shuffle strain a 3.6 kbp EcoRI fragment of CDC53 was cloned into a <URA3 CEN>plasmid. Charged to alanine mutagenesis of Cdc53 was carried out in pMT843, as described previously (Willems et al. 1996). Although none of the mutations caused any obvious phenotype, restriction sites incorporated during mutagenesis were used to construct the deletions shown in FIG. 5. The version of Cdc53 in which all six cysteine residues are replaced by alanines (C59A, C157A, C412A, C606A, C754A, C774A) was created in a single site-directed mutagenesis reaction.

Yeast Strains and Culture

Yeast strains are listed in Table 2. All strains were isogenic with the W303 background. Standard methods were used for yeast culture and transformation (Kaiser et al. 1994). A cdc53$^\Delta$ shuffle strain was constructed by deleting one copy of CDC53 with pMT1514 in K699 a/α transforming with pMT951, sporulating and isolating a Ura$^+$ Ade$^+$ segregant. Complementation of the shuffle strain by various <CDC53$^M$ CEN>plasmids was tested by plating on 0.1% FOA medium. cdc53 skp1 double mutants were generated in crosses of MTY871 with Y553 and Y555 (Bai et al. 1996). The cln2::pGAL1-CLN2$^M$-LEU2 strain was created by integrating pMT1111 into K699a. The MET30-1 strain (CC786-1A) was created by crossing W303-1B with CM100-1A (Thomas et al. 1995). MET25 mRNA expression was assayed in cultures grown in B media supplemented with 0.1 mM sulfate as the sulfur source (Thomas et al. 1995). At a density of 0.5×10$^7$ cells/ml cultures were shifted to 37° C. for 2 hours, repressed with 1.0 mM methionine, and time points taken for RNA extraction. Cln2 halflife was determined in pGAL1-CLN2$^{HA}$ strains as described previously (Willems et al. 1996).

Two Hybrid Analysis

Strain Y187 expressing a Gal4$^{DBD}$ fusion was transformed with a yeast Gal4$^{AD}$-cDNA library (provided by S. Elledge) or a Gal4$^{AD}$ genomic DNA library (James et al. 1996) and screened as described (Durfee et al. 1993). With the cDNA library, Gal4$^{DBD}$-Cdc53 recovered 1 positive clone (A10) from 140,000 transformants, and Gal4$^{DBD}$-Cdc53$^{\Delta K}$ recovered 2 positive clones (C23 and C24) from 225,000 transformants. Gal4$^{DBD}$-Cdc53$^{\Delta N}$ recovered no positive clones from 427,000 transformants. With the genomic DNA library, Gal4$^{DBD}$-Cdc53 recovered 5 positive clones (F15, F19, F20, F23, F24) from 1 million transformants and Gal4$^{DBD}$-Cdc53$^{\Delta K}$ recovered 7 positive clones (H1, H6, H8. H9, H11, H13, H17) from 500,000 transformants. Some clones were isolated several independent times but all unique clones are represented in FIG. 1.

Protein and RNA Analysis

Preparation of yeast lysates and analysis of total RNA were carried out as described previously (Willems et al. 1996). Northern blots were probed with a 1.3 kbp MET25 fragment and a 0.6 kbp ACT1 fragment. mRNA abundance was quantitated on a Molecular Dynamics Storm PhosphorImager. Immunoblots were processed for ECL detection as described (Willems et al. 1996) and where indicated signals were quantitated by densitometry. Affinity purified anti-Cdc4, anti-Cdc34 and anti-Cdc53 antibodies (provided by M. Goebl), and anti-Cdc28 antibodies (Tyers et al. 1992) were used at dilutions between 1:100 to 1:1,000, depending on the particular antibody. Anti-Skp1 antibodies were used at 1:1,000 (Bai et al. 1996). Anti-Grr1 antibodies were adsorbed against polyacrylamide to eliminate background binding and used at 1:100 (Flick and Johnston 1991). Anti-Met30 antibodies were raised against recombinant Gst-Met30 (residues 297–640 encompassing the WD40 repeats), affinity purified and used at a dilution of 1:100. The 9E10 anti-MYC and 12CA5 anti-HA monoclonal antibodies were produced as ascites fluid and used at 1:10,000. Anti-FLAG M2 antibody conjugated to Sepharose beads was from Kodak. HRP-conjugated secondary antibodies (Amersham) were used at a dilution of 1:10,000.

Sequence Analysis

Regions of sequence conservation between Cdc53 homologs identified in database searches were determined by amino acid alignment with ClustalW (Thompson 1994). Conserved residues with a weight of 10 or higher were identified by analysis of 15 full length homologs with the Wisconsin Package program Pretty. Black lines in FIG. 5B indicate the central residue of an 11 residue window containing four or more such conserved residues.

Results

Interactions of Cdc53, Skp1, Cdc4 and Met30 in the Two Hybrid System

Figure 1B:
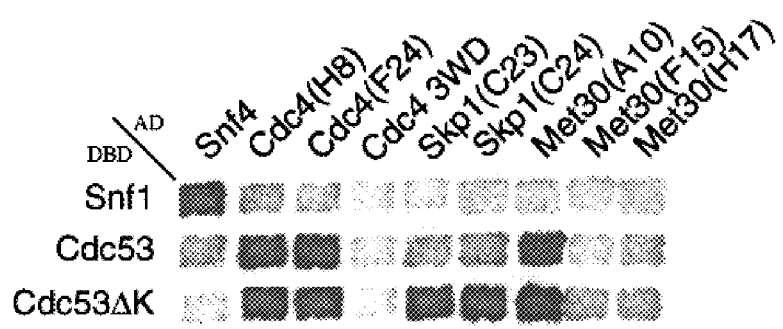
Figure 1C:
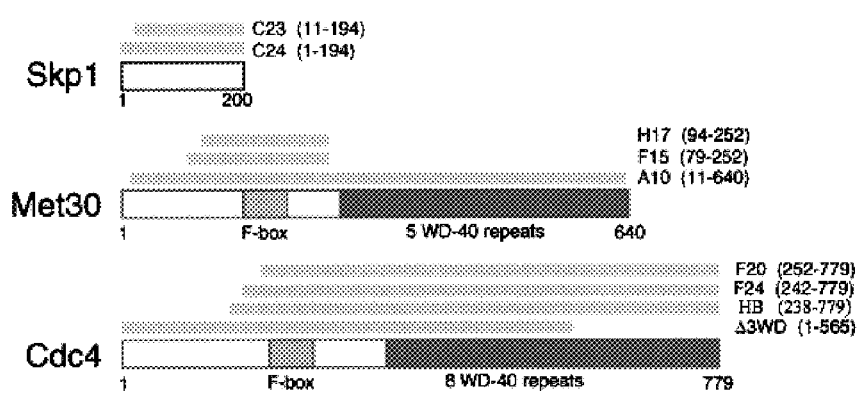
Figure 1D:
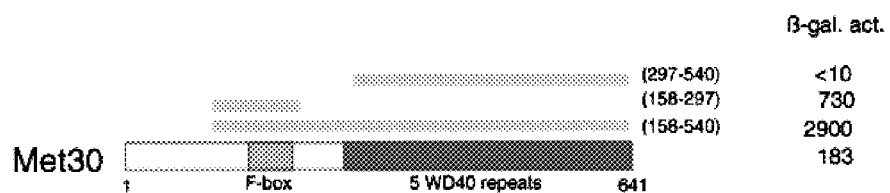

To identify proteins that interact with Cdc53, two hybrid screens were carried out with full length Cdc53 and two Cdc53 deletion mutants (FIG. 1A). Two Cdc53 fusion proteins, Gal4$^{DBD}$-Cdc53 and Gal4$^{DBD}$-Cdc53$^{\Delta K}$, recovered multiple independent isolates of Skp1, Cdc4 and Met30 from Gal4$^{AD}$ genomic and cDNA libraries (FIGS. 1B, 1C). None of the positive clones recovered interacted with Gal4$^{DBD}$-Cdc53$^{\Delta N}$, suggesting that the N-terminal region of Cdc53 was important for these interactions (see below). Met30 was originally isolated as a methionine-dependent repressor of methionine biosynthesis gene expression, and has a similar overall structure as Cdc4, with an N-terminal F-box and C-terminal WD40 repeats (Thomas et al. 1995; Bai et al. 1996). All of the Met30 and Cdc4 isolates that interacted with Cdc53 contained the F-box motif, suggesting the F-box may mediate interactions with Cdc53. In fact, two of three independent Met30 isolates contained just the F-box and a small amount of flanking region (FIG. 1C). Similarly, three independent Cdc4 isolates encompassed the F-box but lacked more N-terminal sequences. Cdc4 and Met30 isolates missing some or all of the WD40 repeats did however interact more weakly with Cdc53 than the full length proteins (FIGS. 1B, C), which may reflect an auxiliary role for the WD40 repeats. Since Cdc4 binds Skp1 via the F-box motif (Bai et al. 1996), a Met30-Skp1 interaction was directly tested for in the two hybrid system. The F-box of Met30 was both necessary and sufficient for interaction of Met30 with Skp1 (FIG. 1D). As for the Cdc53-Met30 interaction, the WD40 repeats of Met30 were required for maximal interaction with Skp1. In summary, two hybrid analysis revealed a Cdc53-Skp1 interaction and suggested the possibility that Cdc53-F-box protein interactions may be bridged by Skp1.

Cdc53 and Skp1 Interact Genetically

Figure 2A:
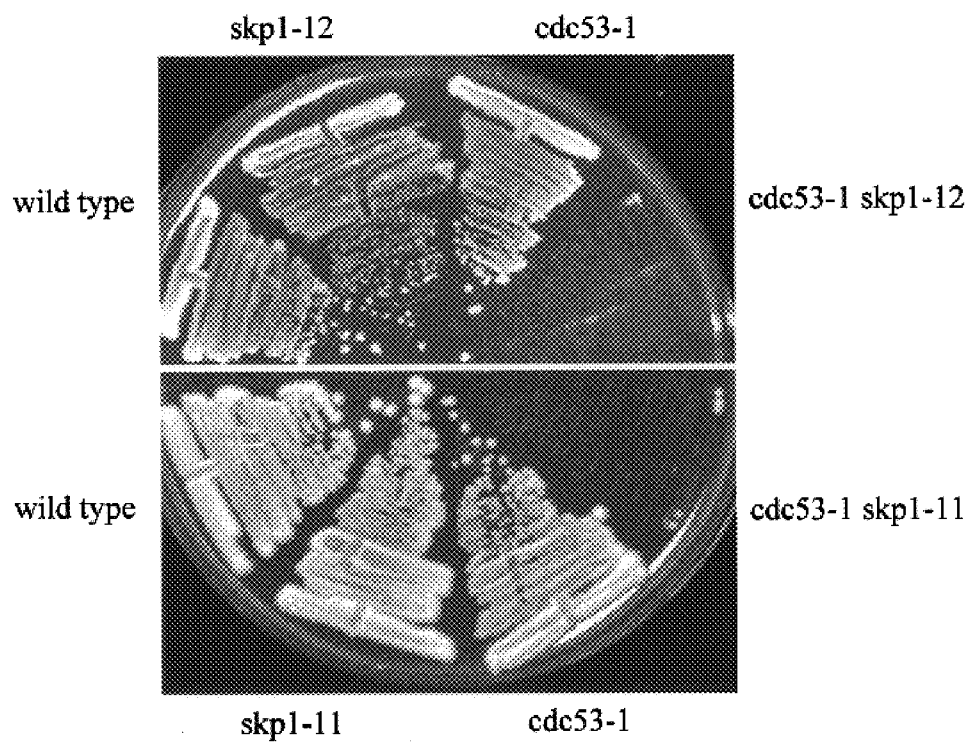
FIG. 2. Genetic interaction between CDC53 and SKP1. (A) cdc53 skp1 double mutants are inviable at the semi-permissive temperature. Spore clones of a representative tetratype tetrad were grown at 30° C. for two days. (B) Photomicrographs of cells from a representative cdc53-1 skp1-12 tetratype grown at 25° C.
Figure 2B:
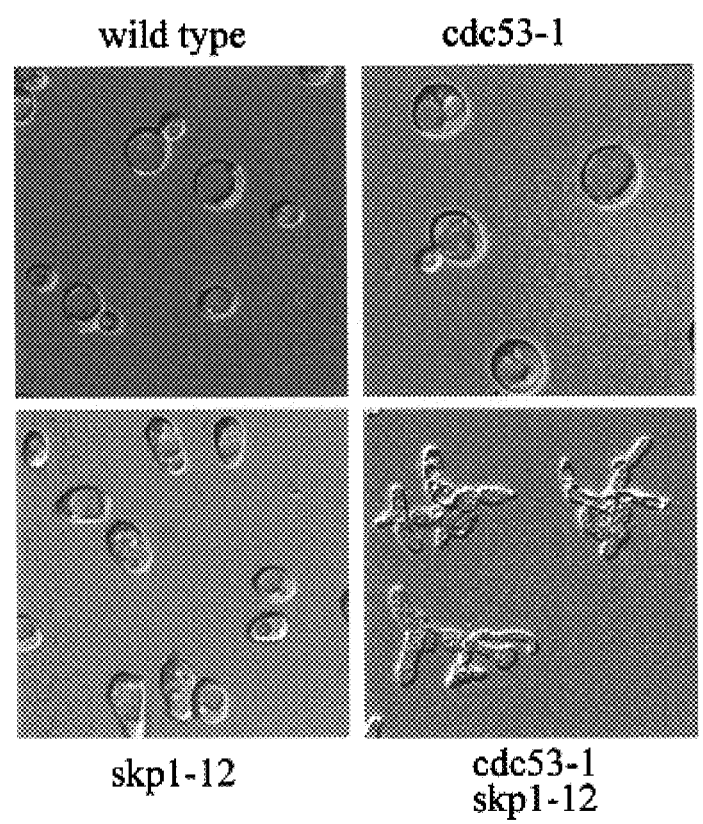

To assess the in vivo relevance of the Cdc53-Skp1 two hybrid interaction, genetic interactions were tested between CDC53 and SKP1. The cdc53-1 mutation was combined with the skp1-11 and skp1-12 mutations. At a semipermissive temperature of 30° C. both the cdc53-1 skp1-11 and cdc53-1 skp1-12 double mutants were inviable, whereas either single mutant grew as well as the wild type strain (FIG. 2A). Even at a permissive temperature of 25° C., cdc53-1 skp1-12 double mutants had a severe growth defect, and accumulated multiple hyperpolarized buds (FIG. 2B), akin to the arrest phenotype of single mutants in the Cdc34 pathway (Mathias et al. 1996). In addition, overproduction of CDC53 was found to rescue skp1 temperature sensitive strains (E. Patton, unpublished data), as reported elsewhere (Skowrya et al. 1997). This genetic evidence suggests that the Cdc53-Skp1 two hybrid interaction reflects a common function of Cdc53 and Skp1 in vivo.

Cdc53 Associates with Skp1 and Cdc4 in Yeast Lysates

Figure 3A:
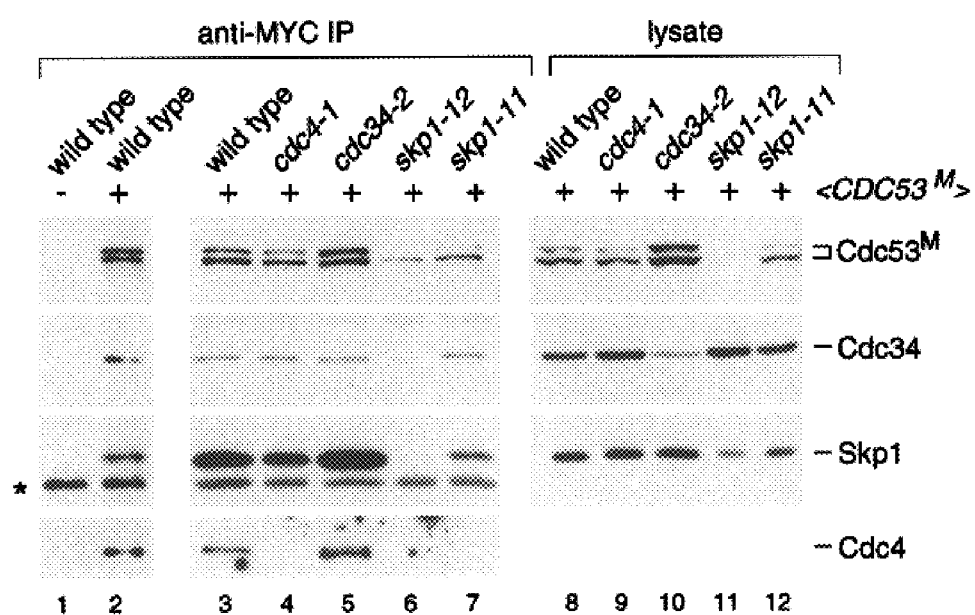
FIG. 3. Characterization of Cdc53 complexes in yeast lysates. (A) Effects of temperature sensitive mutations on the composition of Cdc53 immune complexes. The indicated strains containing <CDC53 CEN> or <CDC53$^M$ CEN> plasmids were arrested at 37° C. for 2 h. 9E10 anti-MYC immunoprecipitates from each strain were immunoblotted and sequentially probed with anti-Cdc4, anti-Cdc34, anti-Skp1 and anti-MYC antibodies. The anti-Cdc4 antibody did not reliably detect Cdc4 in lysates and so the panels were omitted (see part C, below). (B) Effects of temperature sensitive mutations on the composition of Skp1 immune complexes. Analysis was as above except that strains contained either vector or <SKP1$^{HA}$ CEN> plasmids. Anti-HA immunoprecipitates were probed with anti-Cdc4, anti-Cdc34, anti-Cdc53 and anti-HA antibodies. (C) Abundance of Cdc4 and Met30 in skp1 mutants. Wild type, skp1-11, skp1-12 strains containing either vector, <CDC4$^F$ CEN> or <pADH1-MET30$^{HA}$ 2 μm> plasmids, were analyzed as above. Anti-FLAG and anti-HA immunoprecipitates were probed with anti-Cdc4 polyclonal antibody and anti-HA antibody respectively.
Figure 3B:
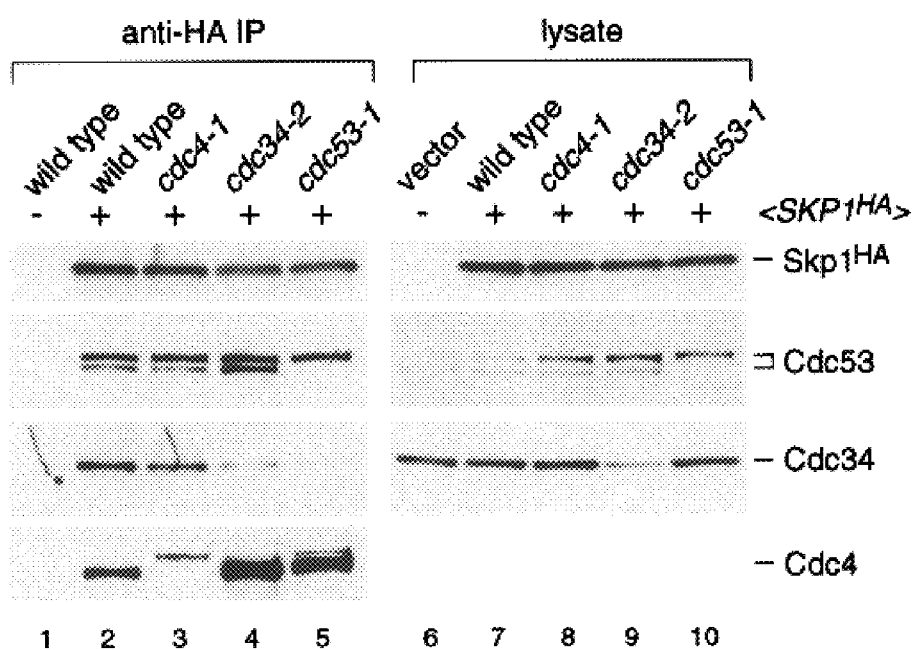

Next it was determined whether endogenous levels of Cdc53 and Skp1 form a complex in yeast lysates. To minimize possible disruption of complexes by antibodies, epitope-tagged versions of Cdc53 and Skp1 were used. Immunoprecipitation of MYC-tagged Cdc53, followed by immunoblotting with polyclonal antibodies directed against Skp1, revealed a specific association between Cdc53 and Skp1 (FIG. 3A, lane 2). Cdc4 and Cdc34 were also present in the Cdc53 complexes, consistent with the observation that Cdc4 and Cdc53 cofractionate with polyhistidine tagged Cdc34 (Mathias et al. 1996). In the reciprocal coimmunoprecipitation experiment, Cdc53 specifically associated with HA-tagged Skp1, as did Cdc4 and Cdc34 (FIG. 3B, lane 2). Taken together, these results indicate that Cdc53 likely forms a multiprotein complex in vivo with Skp1, Cdc4 and Cdc34.

To determine if any of these protein-protein interactions correlated with function in vivo, the composition of the Cdc53 complex was examined in various temperature sensitive strains. In one set of experiments, Cdc53 immune complexes were immunoblotted with anti-Cdc4, anti-Cdc34 and anti-Skp1 antibodies (FIG. 3A). In cdc4 and skp1-11 mutants, Cdc4 was not detected in Cdc53 immune complexes. Although this observation was consistent with a bridging role for Skp1, the absence of Cdc4 from the complexes was due at least in part to decreased Cdc4 abundance in the mutants (see FIG. 3C). The skp1-12 mutation severely decreased the abundance of Cdc4, Cdc53 and Skp1 itself, and so the absence of associated proteins in Cdc53 complexes from skp1-12 cells was not informative.

In another set of experiments, Skp1 immune complexes from temperature sensitive strains were immunoblotted with anti-Cdc4, anti-Cdc34 and anti-Cdc53 antibodies (FIG. 3B). In this configuration, the amount of Cdc4 in the complex was also reduced by the cdc4-1 mutation. In contrast, the amount of Cdc4 in the complex was increased by both the cdc34-2 and cdc53-1 mutations. Relative to the abundance of Cdc34 in lysates, the amount of Cdc34 in Skp1 complexes was severely compromised by the cdc53-1 mutation. Cdc53 may therefore bridge the Cdc34-Skp1 interaction (see below).

Figure 3C:
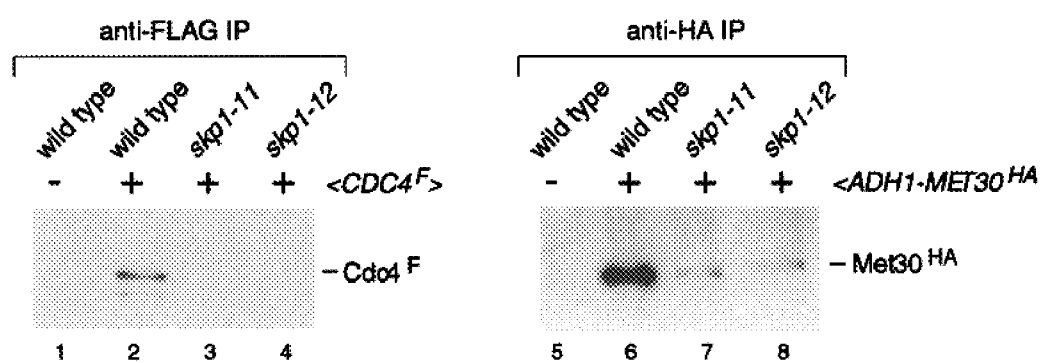

As the anti-Cdc4 antibodies used could not reliably detect Cdc4 in yeast lysates, it was not possible to determine directly if the skp1 mutations reduced the abundance of Cdc4. However, immunoprecipitation of a FLAG-tagged version of Cdc4 followed by immunoblotting with anti-Cdc4 polyclonal antibody revealed that Cdc4 abundance is greatly diminished in skp1-11 and skp1-12 strains (FIG. 3C). The abundance of another F-box protein, Met30, was similarly reduced by the skp1-11 and skp1-12 mutations (FIG. 3C). As noted above, the abundance of Cdc53 is also decreased by the skp1-12 mutation. Thus, Skp1 may function at least in part to stabilize both Cdc53 and F-box proteins. Overall, each of temperature sensitive mutations perturbs the mutual interactions, by altering the abundance of a given component in lysates and/or the immune complexes.

Cdc53 Interacts with Two Other F Box Proteins, Met30 and Grr1

Figure 4A:
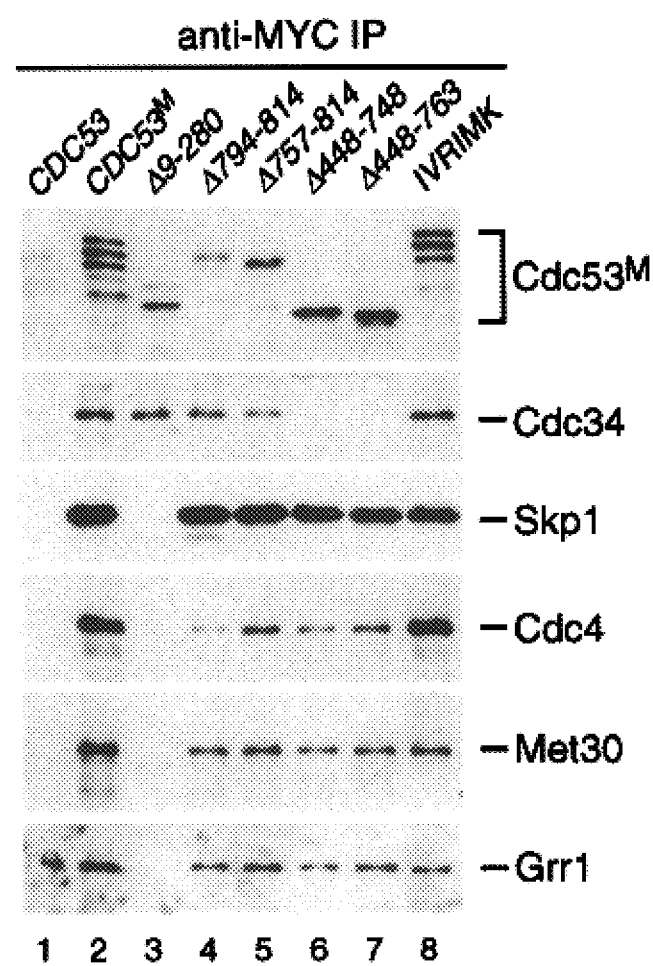
FIG. 4. Cdc53 interacts with multiple F-box proteins. (A) The indicated immunoprecipitates from wild type cells containing either vector, <CDC53$^M$ CEN>, <pADH1-MET30$^{HA}$ 2 μm>, <pADH1-GRR1$^{HA}$ 2 μm> and <CDC4$^F$ CEN> plasmids were probed with anti-Cdc53, anti-Skp1, anti-Cdc4 and anti-HA antibodies. IgG light chain is indicated by an asterisk. (B) Effects of MET30 or GRR1 overexpression. Strains of the indicated genotype containing an empty vector plasmid <pADH1-MET30$^{HA}$> (left panel), or <pADH1-GRR1$^{HA}$> (right panel) were grown at 30° C for 3 days and photographed.

To corroborate the Cdc53-Met30 and Skp1-Met30 two hybrid interactions, studies were carried out to determine if Met30 formed complexes with Cdc53 and Skp1 in yeast lysates. For this purpose an HA-tagged version of Met30 expressed from the constitutive ADH1 promoter was used. Immunoprecipitation of Met30 followed by immunoblotting against Cdc53 and Skp1 revealed the presence of both Cdc53 and Skp1 in Met30 immune complexes (FIG. 4A).

Because several lines of evidence suggest that Grr1 may function with Skp1 and Cdc53 to mediate Cln1/2 degradation (Barral et al. 1995; Bai et al. 1996; Willems et al. 1996), studies were carried out to test if Grr1 interacts with Cdc53. Indeed, both Cdc53 and Skp1 were specifically immunoprecipitated with an HA-tagged version of Grr1 (FIG. 4A). In a control experiment, FLAG-tagged Cdc4 immune complexes also contained Cdc53 and Skp1, thereby completing the set of pairwise coimmunoprecipitations between Cdc4, Cdc34, Cdc53 and Skp1 (FIGS. 3A, B; Mathias et al. 1996). It was not possible to reproducibly detect Cdc34 in the F-box protein immune complexes, perhaps because each of these complexes necessarily contains only a fraction of the total Cdc34, Cdc53 and Skp1. Within the limits of the antibodies it was not possible to detect Cdc4 in Met30 and Grr1 immune complexes, suggesting that F-box proteins form mutually exclusive complexes (data not shown). Thus, Skp1 and Cdc53 form independent complexes with at least three different F-box proteins in vivo.

Figure 4B:
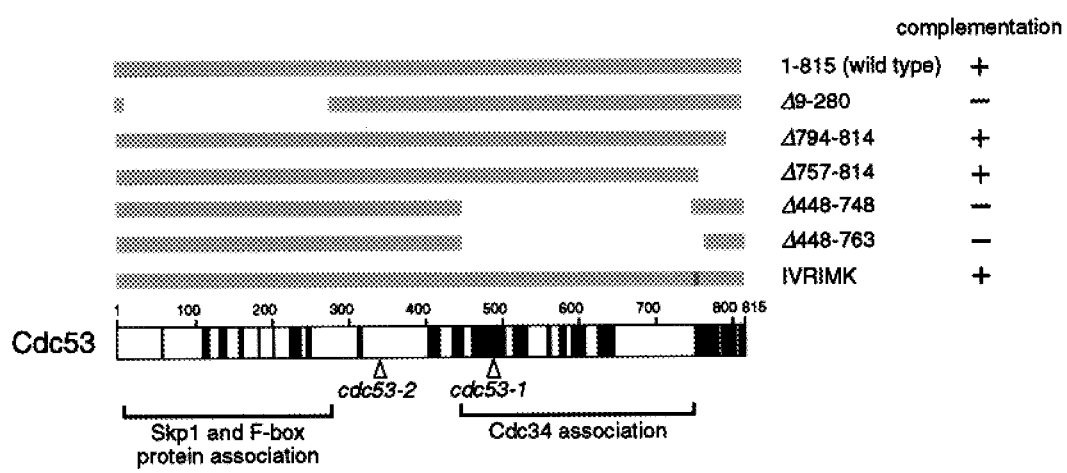
Figure 4C:
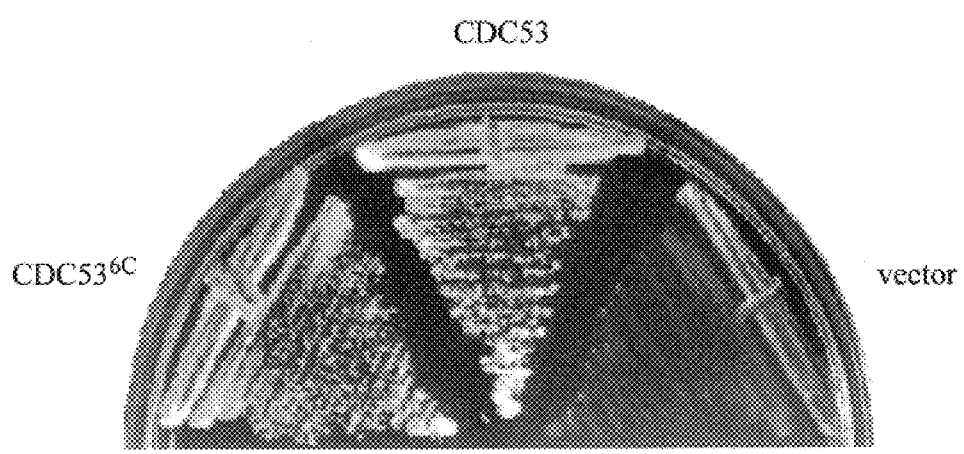

The ability of Cdc53 to interact with multiple F-box proteins raised the possibility that different F-box proteins may compete for binding to a Cdc34-Cdc53-Skp1 core complex. This possibility was tested by overexpressing MET30 or GRR1 in cdc4-1, cdc34-2 and cdc53-1 temperature sensitive strains. Overexpression of MET30 dramatically impaired growth of a cdc4-1 strain at 30° C., and caused a mild growth defect in cdc53 and cdc34 strains (FIG. 4B) but had no effect on either skp1-11 or skp1-12 strains (data not shown). Although overexpression of GRR1 did not affect growth of a cdc4-1 strain, the growth of cdc34-2 and cdc53-1 strains was retarded at 30° C. (FIG. 4B). It has been noted previously that high level expression of GRR1 is lethal in skp1-12 strains at 30° C. (Li and Johnston 1997), and high level expression of Cdc4 causes inviability of cdc34 and cdc53 strains at 23° C. (Mathias et al. 1996). Taken together, the above results suggest various F-box proteins may compete for binding to a core Cdc34-Cdc53-Skp1 complex in vivo, and that the relative stoichiometry of the various complexes is critical for viability.

Cdc53 is a Scaffold Protein for Cdc34 and Skp1-F-box Protein Complexes

Figure 5A:
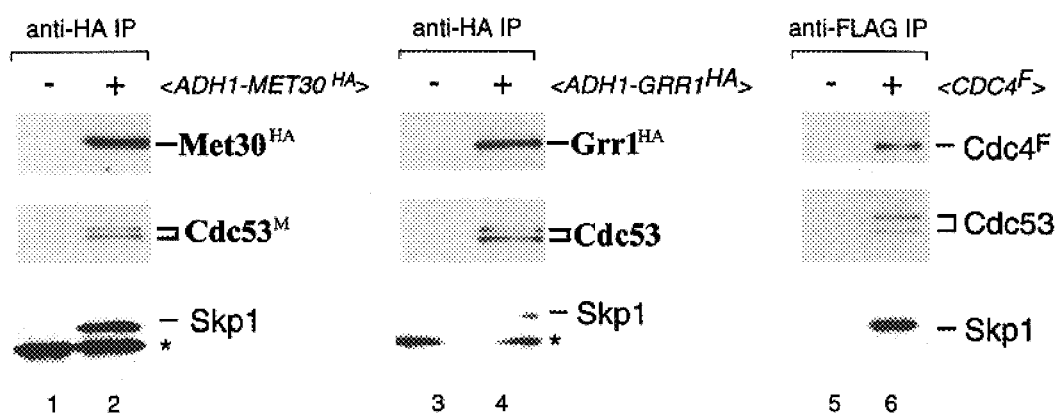
FIG. 5. Mutational analysis of CDC53. (A) Deletion analysis of Cdc53 protein-protein interaction domains. Cells were transformed with untagged (lane 1) or MYC-tagged (lane 2) CDC53 or MYC-tagged versions of the indicated CDC53 mutants (lanes 3–8) all expressed from the wild type promoter on CEN plasmids. Lysates from each strain were immunoprecipitated with 9E10 anti-MYC antibodies, immunoblotted and probed with 9E10 (top panel) and polyclonal antibodies specific to each of the indicated proteins (lower panels). (B) Schematic representation of Cdc53 mutant proteins and their ability to rescue a cdc53 deletion strain. Regions of amino acid sequence conservation in the Cdc53 family are indicated in black (see Methods). The positions of the cdc53-1 (R488C) and cdc53-2 (G340D) point mutations, and the regions required for binding to Skp1/F-box proteins and Cdc34 are also indicated. (C) Cdc53 does not contain essential cysteine residues. A cdc53 deletion strain containing a <CDC53$^{HA}$ URA3 CEN> plasmid was transformed with <CDC53$^{6C}$ TRP CEN>, <CDC53$^M$ TRP CEN>, or an empty vector plasmid, plated on 5-FOA medium to select for Ura$^-$ cells, and photographed after 2 days.

To identify potential protein-protein interaction domains of Cdc53, a series of Cdc53 deletion mutants were constructed using natural and engineered restriction sites (see Methods). Each of the mutant proteins was expressed to similar levels as wild type Cdc53 (FIG. 5A). The ability of each Cdc53 mutant protein to interact with Cdc34, Skp1 and the three F-box proteins Cdc4, Grr1, Met30 was assessed by immunoblot analysis of MYC-tagged Cdc53 immune complexes with specific polyclonal antibodies (FIG. 5A). In this experiment, each of the interactions detected involved approximately wild type levels of Cdc53 (which was expressed from a low copy plasmid) and endogenous levels of each of the associated proteins. Deletion of an N-terrninal region of Cdc53 (residues 9–280) completely disrupted Skp1 binding. In parallel, the binding of all three F-box proteins was specifically disrupted. Importantly, Cdc34 still interacted with Cdc53$^{\Delta 9-280}$, eliminating the possibility that the truncated protein was simply misfolded and entirely non-functional. Conversely, deletion of an internal region of Cdc53 (residues 448–748) abrogated Cdc34 binding but did not affect binding of Skp1 or any of the F-box proteins. The strict correlation between the Cdc53-Skp1 interaction and Cdc53-F-box protein interactions is most easily explained by a bridging function for Skp1. Furthermore, the independent non-overlapping binding regions in Cdc53 indicate that the protein-protein interactions within Cdc53 complexes occur in a modular fashion.

Figure 5B:
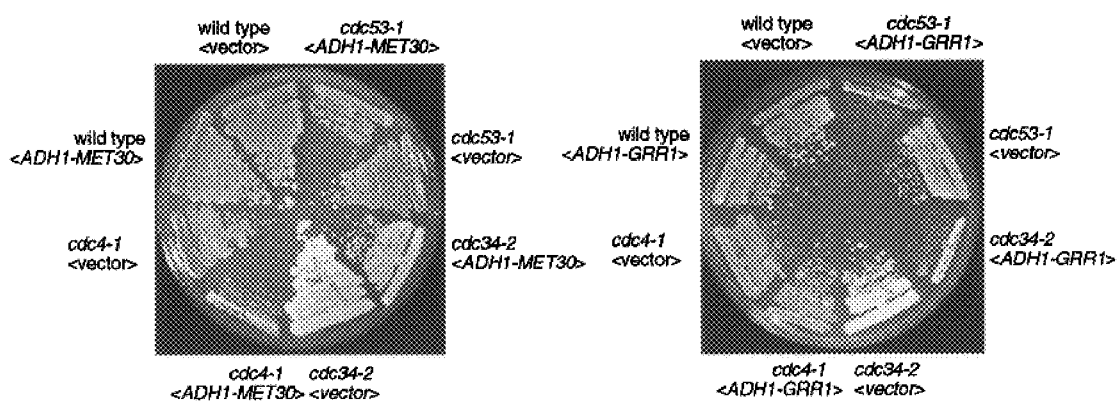

Importantly, Cdc53 mutants that were unable to bind either Skp1/F-box proteins or Cdc34 could not complement a cdc53 deletion strain, while mutants unaffected in protein-protein interactions could complement (FIG. 5B). In order to determine if the Skp1/F-box protein and Cdc34 binding domains of Cdc53 corresponded to conserved regions of Cdc53, 15 different members of the Cdc53 family were aligned (FIG. 5B, see Methods for details of the sequence alignment). Sequence similarity within the Cdc53 family is restricted to a broad internal region and a narrow region at the extreme C-terminus. Surprisingly, the latter region is not required for binding to Skp1/F-box proteins or Cdc34, nor for viability (FIGS. 5A, B). However, the internal conserved region overlaps with the Cdc34 binding site. There is relatively poor conservation in the N-terminus of Cdc53, despite the fact that this region contains the Skp1 binding site. The interaction with Skp1 may possibly be limited to a subset of the Cdc53 family.

Based on the sequence alignment many conserved charged residues in Cdc53 were mutated to alanines but none of the mutants had any overt phenotype. For instance, mutation of the most conserved stretch in the entire protein, IVRIMK (residues 755–760), to polyalanine did not cause an obvious defect in Cdc53 function or in binding to Skp1/F-box proteins or Cdc34 (FIGS. 5A, B). To further explore the structure/function relationship of Cdc53, the sequence of two temperature sensitive alleles of CDC53 were determined. The cdc53-1 mutation causes an R488C substitution while the cdc53-2 mutation causes a G340D substitution. Both mutations alter highly conserved residues, even though G340 does not lie within a window of conserved residues. Interestingly, the cdc53-1 mutation occurs within the Cdc34 binding region. In conjunction with the defective Skp1-Cdc34 interaction in cdc53-1 strains (FIG. 3B), this result strongly suggests that the cdc53-1 mutation specifically perturbs the Cdc34 binding site.

In addition to target protein recognition, some E3 ligases form ubiquitin thioester intermediates on catalytic cysteine residues (Scheffner et al. 1995). As Cdc53 is a component of an E3 ligase complex, studies were carried out to determine whether any of the cysteine residues in the Cdc53 sequence were required for function in vivo. Simultaneous mutation of all six cysteine residues in Cdc53 to alanine did not impair complementation of a cdc53 deletion strain (FIG. 5C). Although this mutational analysis does not rule out thioester formation on Cdc53, such reactions cannot be essential for viability. The primary function of Cdc53 is therefore to act as a scaffold protein for Skp1/F-box proteins and Cdc34.

Cdc34, Cdc53 and Skp1 are Mediators of Methionine Repression

Figure 6A:
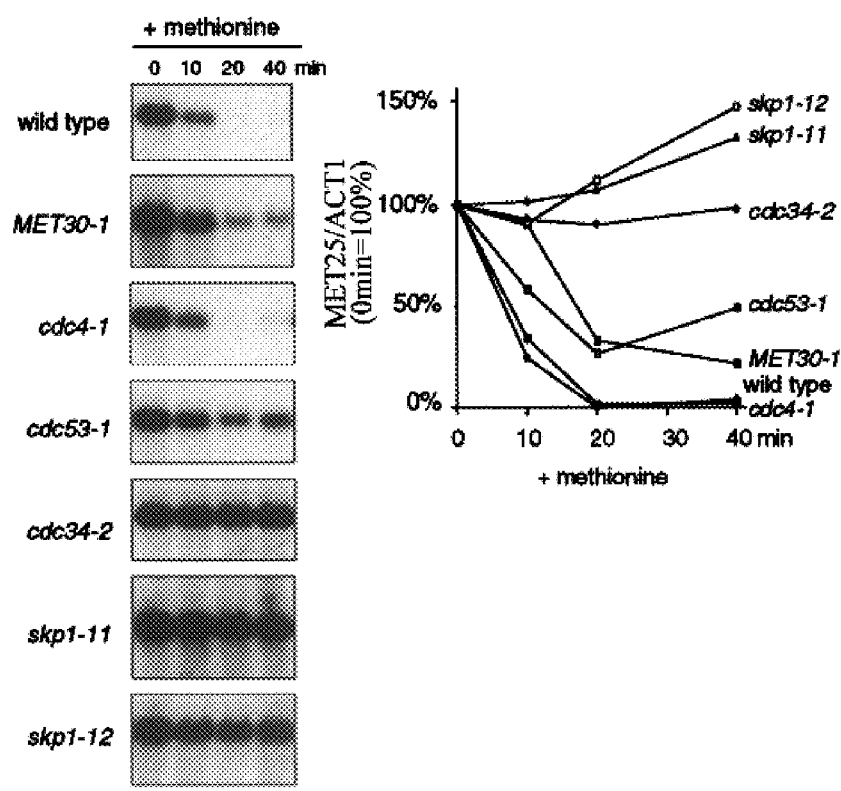
FIG. 6. Specificity of F-box protein function. (A) Methionine repression is mediated by Met30, Cdc34, Cdc53 and Skp1 but not Cdc4. The indicated strains were grown in methionine-free medium and repressed with 1.0 mM methionine for the indicated times. MET25 expression was determined by Northern analysis and normalized to ACT1 expression. (B) Grr1 specifically mediates Cln2 degradation. The indicated strains were incubated at 37° C. for two hours, at which time <pGAL1-CLN2$^{HA}$> was expressed by the addition of galactose for 1.5 hours, and then repressed with the addition of glucose for the indicated times. Cln2$^{HA}$ was detected by immunoblotting with 12CA5 monoclonal antibody. Exposures were adjusted to give equal Cln2$^{HA}$ signals at time zero. Cln2$^{HA}$ was quantitated and normalized to Cdc28 signals from the same blot probed with anti-Cdc28 antibody.

To assess the biological significance of the Cdc53-Met30 and Skp1-Met30 interactions, experiments were carried out to determined if Cdc34, Cdc53, or Skp1 were required for proper regulation of methionine biosynthesis genes. The regulation of MET25, which encodes homocysteine synthase and is representative of methionine regulated genes was examined. MET25 is activated by the Cbf1-Met4-Met28 transcriptional complex and repressed by Met30 (Thomas et al. 1995; Kuras et al. 1996). As expected, methionine repressed ME725 expression in wild type cells (FIG. 6A). As MET30 is an essential gene, an antimorphic allele called MET30-1 was used as a positive control for methionine derepression (Thomas et al. 1995). As shown previously, MET25 is incompletely repressed by methionine in MET30-1 cells. Strikingly, repression of MET25 by methionine was severely compromised in cdc53-1 cells and completely defective in cdc34-2, skp1-11 and skp1-12 cells (FIG. 6A). In contrast, ME125 was effectively repressed with wild type kinetics in cdc4-1 cells, thereby demonstrating the specificity of F-box protein function in methionine biosynthesis gene regulation. The derepression of MET25 observed in cdc34, cdc53 and skp1 mutants did not depend on G1 phase cell cycle arrest because derepression did not occur in cdc4-1 cells which arrest at the identical point in G1, and yet did occur in skp1-12 mutants which arrest in G2 phase.

Specificity of F-box Protein Function in Cln2 Degradation

Figure 6B:
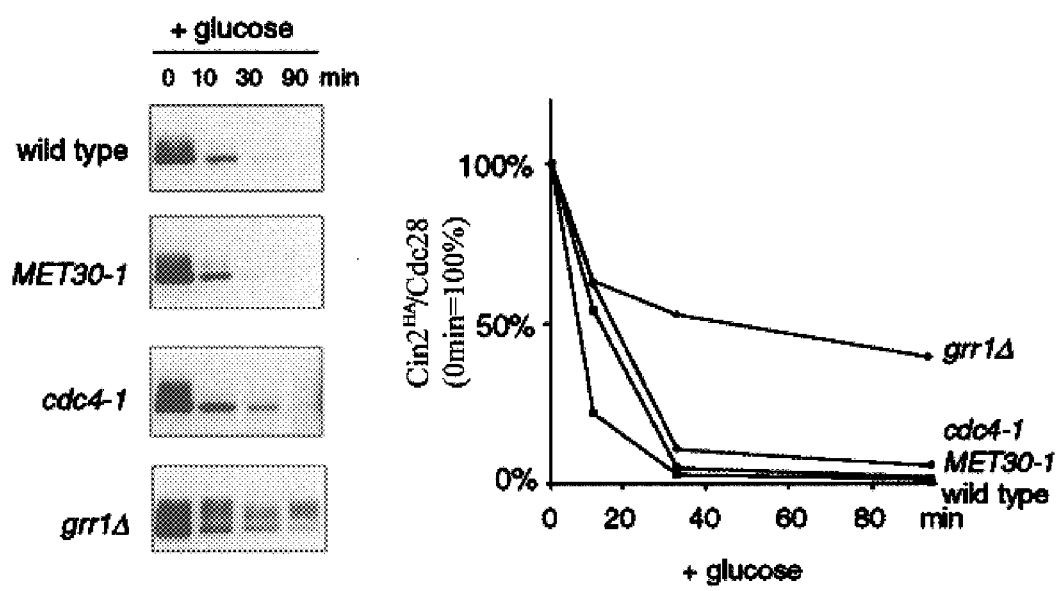

It has been shown previously that Cln2 is stabilized in grr1Δ, cdc34-2, cdc53-1 and skp1-12 strains (Barral et al. 1995; Deshaies et al. 1995; Bai et al. 1996; Willems et al. 1996). To directly assess the specificity of F-box protein function in Cln2 degradation, the halflife of Cln2 in cdc4-1, grr1Δ and MET30-1 strains was compared. We used glucose repression of a pGAL1-CLN2$^{HA}$ construct to measure Cln2 decay rates, as described previously (Willems et al. 1996). Cln2 was strongly stabilized in grr1Δ cells, slightly stabilized in cdc4-1 cells and not stabilized at all in MET30-1 cells (FIG. 6B). Thus Grr1 is the primary mediator of Cln2 degradation, at least under the conditions employed in these experiments. In contrast to Cln2 degradation, and consistent with previous results (Schwob et al. 1994; Bai et al. 1996), Sic1 degradation was found to require Cdc4, but not Grr1 or Met30 (E. Patton, unpublished data).

Discussion

Modular Protein-protein Interactions Allow Combinatorial Control of Skp1-Cdc53-F-box Protein (SCF) Complexes Cdc53 was shown to form a multiprotein complex in vivo with Cdc4, Cdc34 and Skp1. Furthermore, two other F-box proteins, Grr1 and Met30, form analogous complexes with Skp1 and Cdc53. Consistent with these in vivo observations, recombinant Cdc4 and Grr1 assemble into a complex with Cdc34, Cdc53 and Skp1 (Skowrya et al. 1997). To simplify description of the various F-box containing complexes, the generic term SCF, for Skp1-Cdc53-F-box protein complex has been adopted(Skowrya et al. 1997; Feldman et al. 1997).

The specific F-box complexes described above are thus designated SCF$^{CdC4}$, SCF$^{Grr1}$ and SCF$^{Met30}$. Formally, SCF complexes are E3 ubiquitin-ligases, as they interact with both substrates and an E2 enzyme, Cdc34 (Willems et al., 1996; Feldman et al. 1997; Skowrya et al. 1997). In another sense, the Cdc34Cdc53-Skp1 triad forms a core complex that adapts to various F-box proteins via Skp1; this complex is referred to as the E2/E3 core complex.

Substantial evidence indicates that Skp1 bridges F-box proteins to Cdc53. First, the F-box of Met30 is sufficient for interaction with Skp1 and Cdc53 in the two hybrid system. Second, analysis of Cdc53 complexes from skp1 and cdc4 strains shows that Cdc4 is dispensable for the Cdc53-Skp1 interaction. Third, deletion analysis of Cdc53 reveals that the interaction domain for Skp1 matches that of three different F-box proteins, Cdc4, Grr1 and Met30. Furthermore, like the Cdc4-Skp1 interaction, the Cdc53-Skp1 interaction occurs in the absence of other proteins in vitro (Skowrya et al. 1997). However, the interaction of Skp1 with Grr1 in the two hybrid system requires both the F-box and the leucine rich repeats of Grr1 (Li and Johnston 1997). Similarly, the WD40 repeats of Cdc4 and Met30 are required for maximal interaction with Skp1. Overall, it is certain that one function of Skp1 is to help recruit F-box proteins to Cdc53 complexes, perhaps in conjunction with other domains. As noted above, Skp1 may also be required for stabilization of F-box proteins and Cdc53 in vivo.

In addition to the Skp1-F-box interaction, protein-protein interactions within the E2/E3 core complex are of a modular nature. Skp1 binds to the N-terninal region of Cdc53, whereas Cdc34 binds a conserved internal region of Cdc53. The modular nature of these protein-protein interactions and the absence of cysteine-dependent functions in vivo indicates that Cdc53 is a scaffold protein that may anchor Cdc34, Skp1, F-box protein and substrate in the appropriate orientation for ubiquitin transfer.

F-box Proteins Confer Specificity on SCF Function

Despite identification of Cdc34, Cdc53 and Skp1 through defects in Sic1 degradation, it is now clear that SCF complexes also control Cln degradation, glucose repression and methionine repression. SCF$^{Cdc4}$ regulates the G1 to S phase transition through proteolysis of several key cell cycle regulators. The dramatic cell cycle arrest phenotype caused by loss of SCF$^{Cdc4}$ obscures the pleiotropic functions of the E2/E3 core complex, despite the fact that Met30 and Grr1 play crucial roles in cellular metabolism (Flick and Johnston 1991; Thomas et al. 1995). SCF$^{Grr1}$ has a role in both nutrient sensing and cell division, through regulation of glucose repression and Cln degradation, respectively (Flick and Johnston 1991; Barral et al. 1995; Li and Johnston 1997). The present inventors have discovered the existence of a third SCF complex, SCF$^{Met30}$, and demonstrated that in addition to Met30, each component of the E2/E3 core complex is required for regulation of methionine biosynthesis genes.

The specificity of each SCF complex for different cellular processes is demonstrated by a remarkable absence of cross-talk between some of the pathways. For instance, the cdc4-1 mutation does not affect MET25 repression and conversely, the MET30-1 mutation does not affect Cln2 degradation. Although Cdc4 appears not to mediate Cln2 degradation under the experimental conditions employed here, Cdc4 does interact weakly with Cln2 (Skowrya et al. 1997), so a role for Cdc4 in Cln degradation should not yet be excluded. The growth defects caused by high level expression of CDC4, GRR1 or MET30 in various SCF mutants suggests that different F-box proteins may be in equilibrium with a limiting amount of the E2/E3 core complex. If this is so, then F-box proteins may themselves be subject to stringent regulation. The decreased abundance of Cdc4 and Met30 in skp1 temperature sensitive strains is consistent with this possibility, as is the regulation of Grr1 abundance by glucose (Li and Johnston 1997).

It is likely that other SCF complexes regulate yet other processes in yeast. A possible G2 function is suggested by the G2 arrest phenotype of skp1-12 cells (Bai et al. 1996), and by interactions of Skp1 with the Cbf3 kinetochore complex (Connelly and Hieter 1996; Stemmann and Lechner 1996). Finally, because yeast contains two Cdc53 homologs and one Skp1 homolog, orthologous SCF pathways may also exist.

Substrates of SCF Complexes

To date, only Sic1 has been unequivocally identified as a direct target for ubiquitination by a SCF complex. Reconstitution of phosphorylation dependent Sic1 ubiquitination has been achieved in vitro, in both a yeast extract system and in a purified system with recombinant proteins (Verma et al. 1997, Skowyra et al. 1997; Feldman et al. 1997). Strong circumstantial evidence suggests that, in addition to Sic1, $SCF^{Cdc4}$ also targets Far1, Cdc6 and Gcn4 for degradation (Henchoz et al. 1997; McKinney and Cross 1994; Piatti et al. 1996; D. Kornitzer, personal communication). Although ubiquitination of Cln1/2 has not yet been reconstituted, $SCF^{Grr1}$ specifically binds to phosphorylated Cln1/2, consistent with Grr1-dependent degradation of Cln1/2 in vivo (Skowyra et al., 1997). Genetic analysis suggests that a negative regulator of glucose repressed genes called Rgt1 could be a possible target of the $SCF^{Grr1}$ complex (Erickson and Johnston 1994; Vallier et al. 1994). However, it is not known if Rgt1 physically interacts with Grr1, nor if Rgt1 is regulated by ubiquitin dependent proteolysis. The requirement for $SCF^{Met30}$ function in methionine repression implicates ubiquitin-dependent proteolysis. Because Met30 forms a complex with the transactivator Met4, it is possible that Met30 targets Met4 for degradation, although other components of the Met4 transcriptional complex, Cbf1 and Met28, are also candidate targets (Kuras et al. 1996). The mechanisms whereby SCF complex activity is regulated in response to glucose and methionine are unknown, but could involve phosphorylation, subcellular localization, F-box protein abundance and complex assembly (Li and Johnston 1997; Pause et al. 1997).

SCF Complexes in Other Species

SCF complexes have recently emerged as key regulators in other organisms. In *S. pombe*, a Cdc4 homolog, pop1, controls the initiation of S phase by targeting the Cdk inhibitor rum1 and the Cdc6 homolog cdc18 for ubiquitin-dependent proteolysis (Kominami and Toda 1997). In *C. elegans*, null mutants of a Cdc53 homolog called Cul-1 cause hyperplasia in all tissues, suggesting that it too may target activators of division for degradation (Kipreos et al. 1996). In human cells, Skp1 binds to cyclin A-Cdk2 through its associated F-box protein, Skp2, (Zhang et al. 1995) and also forms a specific complex with human Cul-1 (Y. Xiong, personal communication). Another human cullin, Cul-2, physically associates with the VHL tumour suppressor protein, and may thus also regulate cell proliferation (Pause et al. 1997). As in yeast, degradation of mammalian G1 cyclins and Cdk inhibitors is phosphorylation and ubiquitin dependent (Clurman et al. 1996; Won and Reed 1996; Diehl et al. 1997; Sheaff et al. 1997) and so it will be of prime importance to determine the role of SCF complexes in these pathways. The control of gene expression by proteolysis is now well documented in several systems (Pahl and Baeuerle 1996), and by analogy to glucose and methionine regulation in yeast, SCF complexes may prove to be general transcriptional regulators. Indeed, the Met30 homologs Scon2/SconB and the Skp1 homolog SconC regulate sulfur metabolism in other fungi (Natorff et al. 1993; Kumar and Paietta 1995), suggesting that control of methionine biosynthesis by SCF complexes may be conserved. As metazoans contain at least six Cdc53 homologs (Kipreos et al. 1996), and as SCF complexes control multiple processes in yeast, it is likely that analogous SCF complexes will have both cell cycle and non-cell cycle functions in higher species. The combinatorial control of SCF ubiquitin-ligase complexes provides an adaptable regulatory system that controls cell function through ubiquitin-dependent protein degradation.

EXAMPLE 2

Identification of a Skp1 Binding Region in the Cdc53 Protein of the Budding Yeast *Saccharomyces cerevisiae*

Figure 12A:
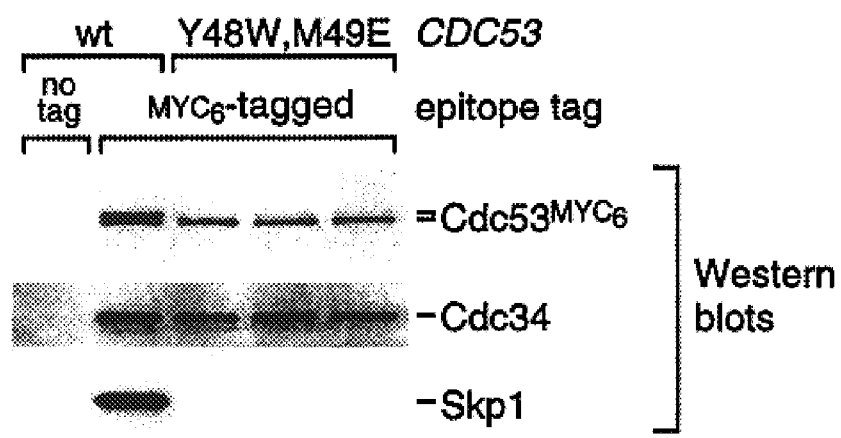
FIG. 12A Amino acids Y48 and M49 in Cdc53 are required for binding to Skp1. Wild type and Y48W, M49E mutants of Cdc53 were immunoprecipitated and western blotted for Cdc53$^{MYC6}$, Cdc34, and Skp1.
Figure 12B:
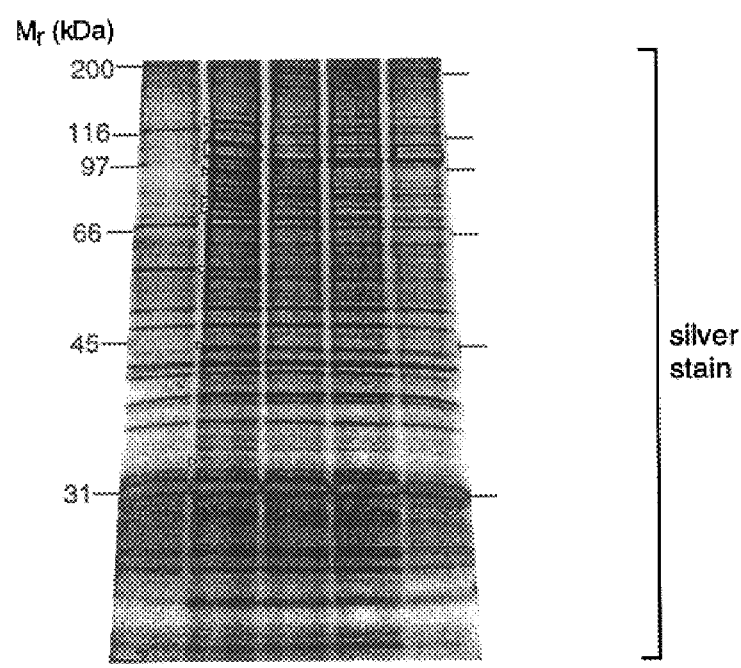
FIG. 12B Amino acids Y48 and M49 in Cdc53 are required for binding to Skp1. Wild type and Y48W, M49E mutants of Cdc53$^{MYC6}$ were immunoprecipitated and western blotted for Cdc53$^{MYC6}$, Cdc34, and Skp1, and (B) silver stained. On the silver-stained gel, bands that exist in the wild type but not the mutant Cdc53 IP are marked with an open triangle.

Amino acids 9–280 of the Cdc53 protein in *Saccharomyces cerevisiae* have been shown to be necessary for associate with Skp1 (Patton et al, 1998, Genes Dev. 12:692). FIG. 11 shows an alignment of amino acids 9 to 99 Cdc53 with other Cdc53 cullin homologues. The amino acids corresponding to tyrosine (Y) 48 methionine (M) 49 in Cdc53 were absolutely conserved in a subset of homologues more closely related to Cdc53 but not present in any of the other more distantly related homologues (with the exception of Y50 in C3A11.8 in *Schizosaccharomyces pombe*). These two amino acids in Cdc53 were mutated by Kunkel mutagenesis to tryptophan (W) and glutamic acid (E) respectively the momologous residues in *Caenorhabditus elegans* Cul-3. Five independent TRP1 plasmid isolates (pMT1939–1943) of this mutagenesis reactin, as well as a plasmid carrying a wild type CDC53 gene (pMT843), were transformed into a CDC53 "shuffle strain" (strain Mty1243, genotype ura3 trp1 leu2 his3 ade2 cdc53::ADE2<$CDC53^{HA3}$ URA3 CEN6 ARSH4>). These mutant and wild type CDC53 genes wre tagged with a $MYC_6$ epitope. These trains were grown on complete minimal medium agar plates containing 1 g/L of 5-fluoroorotic acid, which kills cells that produce Ura3, thus killing any cells that do not lose the <$CDC53^{HA3}$ URA3>plasmid. None of the five CDC53-Y48W,M49E$^{MYC6}$ mutants conferred viability on the shuffle strain, while the wild type $CDC53^{MYC6}$ did. Cells containing either the wild type $CDC53^{MYC6}$ or one of three isolates of the mutant $CDC53^{MYC6}$ were grown to late-log phase ($2 \times 10^7$ cells/ml), harvested, washed, resuspended in lysis buffer (50 mM Tris-Cl pH 7.5, 250 mM NaCl, 50 M NaF., 5 mM EDTA, 0.1% NP-40, 1 mM DTT) plus protease inhibitors, snap frozen in liquid nitrogen, and ground into a powder under liquid nitrogen. This powder was thawed, spun to remove cellular debris, and cleared by spinning in ultracentrifuge. Protein concentration in the lysate was adjusted to 24 mg/ml in a volume of 1.25 ml lysis buffer+10 mM N-ethyl maleimide, for a final mass of 30 mg protein for each strain. 25 µl of a 50% slurry in lysis buffer of protein-A beads (Pierce) cross-linked with dimethyl suberimidate to the anti-MYC monoclonal antibody 9E10 was added to each lysate, incubated with gentle rocking at 4° C. for several hours, washed several times with lysis buffer, aspirated, resuspended in protein sample buffer, and run on two 10% polyacrylamide gels. One gel was transferred to polyvinylidene fluoride membrane and western blotted with anti-MYC, anti-Cdc34, and anti-Skp1 antibodies (FIG. 12A). The mutant Cdc53 still binds to Cdc34 but not to Skp1. the second gel was silver stained (see W. Wray et al. 1981, Anal. Biochem. 118:197) (FIG. 12B). A number of bands that are present in the Cdc53$^{MYC6}$ immunoprecipitation disappear in the Cdc53-Y48W, M49E$^{MYC6}$ immunoprecipitation.

Having illustrated and described the principles of the invention in a preferred embodiment, it should be appreciated to those skilled in the art that the invention can be modified in arrangement and detail without departure from such principles. All modifications coming within the scope of the following claims are claimed.

All publications, patents and patent applications referred to herein are incorporated by reference in their entirety to the same extent as if each individual publication, patent or patent application was specifically and individually indicated to be incorporated by reference in its entirety.

TABLE 1

Plasmids used in this study

| Plasmid | Relevant characteristics | Source |
| --- | --- | --- |
| pMT634 | pGAL1-CLN2-HA LEU2 URA3 CEN | Willems et al. (1997) |
| pMT814 | CDC53-C-NotI TRP1 CEN | Willems et al. (1996) |
| pMT843 | CDC53$^M$ TRP1 CEN | Willems et al. (1996) |
| pMT915 | GALA$^{AD}$-CDC4$^{\Delta 3WD}$ LEU2 2 $\mu$m | This study |
| pMT918 | CDC53 in pAS1-CYH2 TRP1 2 $\mu$m | This study |
| pMT951 | CDC53$^{HA}$ URA3 CEN | This study |
| pMT954 | pGALA$^{DBD}$-CDC53 $\Delta$N TRP1 2 $\mu$m | This study |
| pMT955 | pGALA$^{DBD}$-CDC53 $\Delta$K TRP1 2 $\mu$m | This study |
| pMT1111 | pUC119 cln2::GAL-CLN2$^M$-LEU2 | B. Schneider |
| pMT1511 | SKP1$^{HA}$ LEU2 CEN | P. Heiter |
| pMT1514 | cdc53::ADE2 in pGEM3 | This study |
| pBF339 | pADH1$^{HA}$ TRP1 2 $\mu$m | Li and Johnston (1997) |
| pBF494 | pADH1$^{HA}$-GRR1$^{\Delta N}$ TRP1 2 $\mu$m | Li and Johnston (1997) |
| pMT1707 | pADH1$^{HA}$-MET30 TRP1 2 $\mu$m | This study |
| pMT1850 | CDC53$^{M\Delta 9-280}$ TRP1 CEN | This study |
| pMT1854 | CDC53$^{M\Delta 488-763,H767A}$ TRP1 CEN | This study |
| pMT1856 | CDC53$^{M\Delta 488-748}$ TRP1 CEN | This study |
| pMT1857 | CDC53$^{M\Delta 757-815}$ TRP1 CEN | This study |
| pMT1858 | CDC53$^{M\Delta 794-815}$ TRP1 CEN | This study |
| pMT1859 | CDC53$^{MIVRIMK}$ TRP1 CEN | This study |
| pMT1861 | CDC53$^{M6C}$ TRP1 CEN | This study |
| pLexM30-4 | pLEXA$^{DBD}$-MET30 TRP1 2 $\mu$m | This study |
| pLexM30-4(297-540) | pLEXA$^{DBD}$-MET30 $^{\Delta 297-540}$ TRP1 2 $\mu$m | This study |
| pLexM30-4(158-297) | pLEXA$^{DBD}$-MET30 $^{\Delta 158-297}$ TRP1 2 $\mu$m | This study |
| pLexM30-4(158-540) | pLEXA$^{DBD}$-MET30 $^{\Delta 158-540}$ TRP1 2 $\mu$m | This study |
| pVAD1-SKP1 | pVAD-SKP1 LEU2 2 $\mu$m | This study |
| pSE1111 | GALA$^{AD}$-SNF1 LEU2 2 $\mu$m | S. Elledge |
| pSe1112 | GALA$^{DBD}$-SNF4 TRP1 2 $\mu$m | S. Elledge |
| pRS314 | TRP1 CEN | Sikorski and Hieter (1989) |

TABLE 2

Yeast strains used in this study

| Strain | Relevant genotype | Source |
| --- | --- | --- |
| K699 | MATa ade2-1 can1-100 his3-1,15 leu2-3,112 trp1-1 ura3 | K. Nasmyth |
| K699 a/α | MATa/MATα ade2-1/ade2-1 can1-100/can1-100 his3-1,15/his3-1,15 leu2-3,112/leu2-3,112 trp1-1/trp1-1 ura3/ura3 | K. Nasmyth |
| MTY668 | MATa cdc4-1 | This study |
| MTY670 | MATa cdc34-2 | Willems at al. (1996) |
| MTY871 | MATa cdc53-1 | Willems at al. (1996) |
| MTY1243 | cdc53::ADE2, pMT951 plasmid | This study |
| MTY1293 | cdc53-1 skp1-11 | This study |
| MTY1294 | cdc53-1 skp1-12 | This study |
| MTY1295 | cln2::pGAL1-CLN2$^M$ LEU2 | This study |
| Y187 | MATa ade2-101 his3-Δ200 leu2-3,112 trp1-901 ura3-52 gal4Δ gal80Δ URA3::GAL-lacZ LYS2::GAL-HIS3 | S. Elledge |
| Y190 | as for Y187 but MATα | S. Elledge |
| Y553 | MATα skp1-11 | Bai et al. (1996) |
| Y555 | MATα skp1-12 | Bai et al. (1996) |
| WX131-2c | MATα cdc53-2 trp1-7 ura3-52 ade2 | M. Goebl |
| CC786-1A | ade2 his3 leu2 ura3 trp1 MET30-1 | This study |
| C170 | ade2 his3 leu2 trp1 met4::TRP1 ura3::lexAop-lacZ::URA3 | Kuras and Thomas (1995) |

References

Bai, C., P. Sen, K. Hofmann, L. Ma, M. Goebl, J. W. Harper, and S. J. Elledge. 1996. SKP1 connects cell cycle regulators to the ubiquitin proteolysis machinery through a novel motif, the F-box. *Cell* 86: 263–274.

Barral, Y., S. Jentsch, and C. Mann. 1995. G1 cyclin turnover and nutrient uptake are controlled by a common pathway in yeast. *Genes & Dev.* 9: 399–409.

Clurman, B. E., R. J. Sheaff, K. Thress, M. Groudine, and J. M. Roberts. 1996. Turnover of cyclin E by the ubiquitin-proteasome pathway is regulated by cdk2 binding and cyclin phosphorylation. *Genes & Dev.* 10: 1979–1990.

Connelly, C., and P. Hieter. 1996. Budding yeast SKP1 encodes an evolutionarily conserved kinetochore protein required for cell cycle progression. *Cell* 86: 275–285.

Deshaies, R. J. 1997. Phosphorylation and proteolysis: partners in the regulation of cell division in budding yeast. *Curr Opin Genet Dev* 7: 7–16.

Deshaies, R. J., V. Chau, and M. Kirschner. 1995. Ubiquitination of the G1 cyclin Cln2p by a Cdc34p-dependent pathway. *EMBO J.* 14: 303–312.

Diehl, J. A., F. Zindy, and C. J. Sherr. 1997. Inhibition of cyclin D1 phosphorylation on threonine-286 prevents its rapid degradation via the ubiquitin-proteasome pathway. *Genes & Dev.* 11: 957–972.

Durfee, T., K. Becherer, P.-L. Chen, S.-H. Yeh, Y. Yang, K. A. E., W. H. Lee, and S. J. Elledge. 1993. The retinoblastoma protein associates with the protein phosphatase type 1 catalytic subunit. *Genes & Dev.* 7: 555–569.

Erickson, J. R. and M. Johnston. 1994. Suppressors reveal two classes of glucose repression genes in the yeast *Saccharomyces cerevisiae*. *Genetics* 136: 1271–1278.

Flick, J. S. and M. Johnston. 1991. Grr1 of *Saccharomyces cerevisiae* is required for glucose repression and encodes a protein with leucine-rich repeats. *Mol. Cell. Biol.* 11: 5101–5112.

Goebl, M. G., J. Yochem, S. Jentsch, J. P. McGrath, A. Varshavsky, and B. Byers. 1988. The yeast cell cycle gene CDC34 encodes a ubiquitin-conjugating enzyme. *Science* 241: 1331–1335.

Hershko, A., H. Heller, S. Elias, and A. Ciechanover. 1983. Components of ubiquitin-protein ligase system. Resolution, affinity purification, and role in protein breakdown. *J. Biol. Chem.* 258: 8206–8214.

Hochstrasser, M. 1996. Ubiquitin-dependent protein degradation. *Annu. Rev. Genet.* 30: 405–439.

James, P., J. Halladay, and E. A. Craig. 1996. Genomic libraries and a host strain designed for highly efficient two-hybrid selection in yeast. *Genetics* 144: 1425–1436.

Kaiser, C., S. Michaelis, and A. Mitchell. 1994. *Methods in Yeast Genetics*. Cold Spring Harbor Laboratory Press, Cold Spring Harbor, N.Y.

King, R. W., R. J. Deshaies, J. M. Peters, and M. W. Kirschner. 1996. How proteolysis drives the cell cycle. *Science* 274: 1652–1659.

Kipreos, E. T., L. E. Lander, J. P. Wing, W. W. He, and E. M. Hedgecock. 1996. cul-1 is required for cell cycle exit in *C. elegans* and identifies a novel gene family. *Cell* 85: 829–839.

Kominami, K. and T. Toda. 1997. Fission yeast WD-repeat protein pop1 regulates genome ploidy through ubiquitin-proteasome-mediated degradation of the CDK inhibitor Rum1 and the S-phase initiator Cdc18. *Genes & Dev.* 11: 1548–1560.

Komitzer, D., B. Raboy, R. G. Kulka, and G. R. Fink. 1994. Regulated degradation of the transcription factor Gcn4. *EMBO J.* 13: 6021–6030.

Kumar, A. and J. V. Paietta. 1995. The sulfur controller-2 negative regulatory gene of *Neurospora crassa* encodes a protein with beta-transducin repeats. *Proc. Natll. Acad. Sci.* 92: 3343–3347.

Kuras, L., H. Cherest, K. Y. Surdin, and D. Thomas. 1996. A heteromeric complex containing the centromere binding factor 1 and two basic leucine zipper factors, Met4 and Met28, mediates the transcription activation of yeast sulfur metabolism. *EMBO J.* 15: 2519–2529.

Mathias, N., S. L. Johnson, M. Winey, A. E. Adams, L. Goetsch, J. R. Pringle, B. Byers., and M. Goebl. 1996. Cdc53p acts in concert with Cdc4p and Cdc34p to control the G1-to-S-phase transition and identifies a conserved family of proteins. *Mol. Cell. Biol.* 16: 6634–6643.

McKinney, J. D., F. Chang, N. Heintz, and F. R. Cross. 1993. Negative regulation of FAR1 at the Start of the yeast cell cycle. *Genes & Dev.* 7: 833–843.

Nasmyth, K. 1996. At the heart of the budding yeast cell cycle. *Trends. Genet.* 12: 405–412.

Natorff, R., M. Balinska, and A. Paszewski. 1993. At least four regulatory genes control sulphur metabolite repression in *Aspergillus nidulans*. *Mol. Gen. Genet.* 238: 185–192.

Nugroho, T. T. and M. D. Mendenhall. 1994. An inhibitor of yeast cyclin-dependent protein kinase plays an important role in ensuring the genomic integrity of daughter cells. *Mol. Cell. Biol.* 14: 3320–3328.

Pahl, H. L. and P. A. Baeuerle. 1996. Control of gene expression by proteolysis. *Curr. Opin. Cell Biol.* 8: 340–347.

Pause, A., S. Lee, R. A. Worrell, D. Y. Chen, W. H. Burgess, W. M. Linehan, and R. D. Klausner. 1997. The von Hippel-Lindau tumor-suppressor gene product forms a stable complex with human CUL-2, a member of the Cdc53 family of proteins. *Proc. Natl. Acad. Sci.* 94: 2156–2161.

Piatti, S., T. Bohm, J. H. Cocker, J. F. Diffley, and K. Nasmyth. 1996. Activation of S-phase-promoting CDKs in late G1 defines a "point of no return" after which Cdc6 synthesis cannot promote DNA replication in yeast. *Genes & Dev.* 10: 1516–1531.

Scheffner, M., U. Nuber, and J. M. Huibregtse. 1995. Protein ubiquitination involving an E1-E2-E3 enzyme ubiquitin thioester cascade. *Nature* 373: 81–83.

Schneider, B. L., Q.-H Yang, and A. B. Futcher. 1996. Linkage of replication to Start by the Cdk inhibitor Sic1. *Science* 272: 560–562.

Schwob, E., T. Bohm, M. D. Mendenhall, and K. Nasmyth. 1994. The B-type cyclin kinase inhibitor $p40^{SIC1}$ controls the G1 to S transition in *S. cerevisiae*. *Cell* 79: 233–244.

Sheaff, R. J., M. Groudine, M. Gordon, J. M. Roberts, and B. E. Clurman. 1997. Cyclin E-CDK2 is a regulator of p27Kip1. *Genes & Dev* 11: 1464–1478.

Skowrya, D., K. L. Craig, M. Tyers, S. J. Elledge, and J. W. Harper. 1997. F-box proteins are receptors that recruit phosphorylated substrates to the SCF ubiquitin-ligase complex. *Cell* 91:209–219, 1997.

Stemmann, O. and J. Lechner. 1996. The *Saccharomyces cerevisiae* kinetochore contains a cyclin-CDK complexing homologue, as identified by in vitro reconstitution. *EMBO J.* 15: 3611–3620.

Thomas, D., L. Kuras, R. Barbey, H. Cherest, P. L. Blaiseau, and Y. Surdin-Kerjan. 1995. Met30p, a yeast transcriptional inhibitor that responds to S-adenosylmethionine, is an essential protein with WD40 repeats. *Mol Cell Biol* 15: 6526–6534.

Thompson, J. D., Higgins, D. G. and Gibson, T. J. 1994. CLUSTAL W: improving the sensitivity of progressive multiple sequence alignment through sequence weighting position-specific gap penalties and weight matrix choice. *Nucleic Acids Research* 22: 4673–4680.

Tyers, M. 1996. The cyclin-dependent kinase inhibitor p40$^{SIC1}$ imposes the requirement for CLN G1 cyclin function at Start. *Proc. Natl. Acad. Sci.* 93: 7772–7776.

Tyers, M., G. Tokiwa, R. Nash, and B. Futcher. 1992. The Cln3-Cdc28 kinase complex of *S. cerevisiae* is regulated by proteolysis and phosphorylation. *EMBO J.* 11: 1773–1784.

Vallier, L. G., D. Coons, L. F. Bisson, and M. Carlson. 1994. Altered regulatory responses to glucose are associated with a glucose transport defect in grr1 mutants of *Saccharomyces cerevisiae*. *Genetics* 136: 1279–1285.

Verma, R., R. M. Feldman, and R. J. Deshaies. 1997. SIC1 is ubiquitinated in vitro by a pathway that requires CDC4, CDC34, and cyclin/CDK activities. *Mol. Biol. Cell.* 8: 1427–1437.

Willems, A. R., S. Lanker, E. E. Patton, K. L. Craig, T. F. Nason, N. Mathias., R. Kobayashi, C. Wittenburg, and M. Tyers. 1996. Cdc53 targets phosphorylated G1 cyclins for degradation by the ubiquitin proteolytic pathway. *Cell* 86: 453–463.

Won, K. A. and S. I. Reed. 1996. Activation of cyclin E/CDK2 is coupled to site-specific autophosphorylation and ubiquitin-dependent degradation of cyclin E. *EMBO J.* 15: 4182–4193.

Yochem, J., and B. Byers. 1987. Structural comparison of the yeast cell division cycle gene CDC4 and a related pseudogene. *J. Mol. Biol.* 195: 233–245.

Zhang, H., R. Kobayashi, K. Galaktionov, and D. Beach. 1995. p19Skp1 and p45Skp2 are essential elements of the cyclin A-CDK2 S phase kinase. *Cell* 82: 915–925.

We claim:

1. An isolated peptide of the formula I which interferes with the interaction of Cdc53 and Skp1

$Xaa^1$-Tyr-Met-$Xaa^2$-$Xaa^3$-Tyr-$Xaa^4$-$Xaa^5$-$Xaa^6$-Tyr-$Xaa^7$-$Xaa^8$-Cys-$Xaa^9$ (SEQ. ID. NO: 48)

wherein $Xaa^1$ represents one to ten amino acids, $Xaa^2$ represents Met, Arg, Thr, or Glu, $Xaa^3$ represents Leu, Phe, or Val, $Xaa^4$ represents Asp or Thr, $Xaa^5$ represents Ala, Ser, His, or Thr, $Xaa^6$ represents Ile or Val, $Xaa^7$ represents Asn or Asp, $Xaa^8$ represents Tyr, Ile, or Met, and $Xaa^9$ represents Thr, Val, or Ala.

2. An isolated peptide which interferes with the interaction of Cdc53 and Skp1 selected from the group consisting of:

ILSPTMYMEVYTAIYNYCVNKS (SEQ. ID. NO:3),
MAPKDYMTLYTSVYDYCTSIT (SEQ. ID. NO: 6),
HMSKKYYMMLYDAVYNICTTTT (SEQ. ID. NO: 9),
SLTRSQYMRFYTHVYDYCTSVS (SEQ. ID. NO: 12),
SMAKSRYMELYTHVYNYCTSVH (SEQ. ID. NO: 15), and
AFDSEQYMMLYTTIYNMCTQKP (SEQ. ID. NO: 18).

* * * * *